US009546377B2

(12) United States Patent
Andreuzza et al.

(10) Patent No.: US 9,546,377 B2
(45) Date of Patent: Jan. 17, 2017

(54) METHODS FOR THE IDENTIFICATION OF GENES INVOLVED IN ABIOTIC STRESS TOLERANCE IN PLANTS

(71) Applicant: E I DU PONT DE NEMOURS AND COMPANY, Wilmington, DE (US)

(72) Inventors: Bindu Andreuzza, Hyderabad (IN); Milo Aukerman, Newark, DE (US); Jason L. Brothers, Newark, DE (US); Norbert Brugiere, Johnston, IA (US); Mai Komatsu, Wilmington, DE (US); Ratna Kumria, Hyderabad (IN); Xiao-Yi Li, Wilmington, DE (US); Cheng Lu, Newark, DE (US); Amitabh Mohanty, Kowkur (IN); Hajime Sakai, Newark, DE (US); James J. Saylor, Newark, DE (US); Sobhana Sivasankar, Adel, IA (US); Graziana Taranino, Wilmington, DE (US); Robert Wayne Williams, Hockessin, DE (US)

(73) Assignees: E I DU PONT DE NEMOURS AND COMPANY, Wilmington, DE (US); PIONEER HI-BRED INTERNATIONAL, INC., Johnston, IA (US)

( * ) Notice: Subject to any disclaimer, the term of this patent is extended or adjusted under 35 U.S.C. 154(b) by 4 days.

(21) Appl. No.: 14/354,276

(22) PCT Filed: Oct. 29, 2012

(86) PCT No.: PCT/US2012/062374
§ 371 (c)(1),
(2) Date: Apr. 25, 2014

(87) PCT Pub. No.: WO2013/063555
PCT Pub. Date: May 2, 2013

(65) Prior Publication Data
US 2014/0304854 A1    Oct. 9, 2014

Related U.S. Application Data

(60) Provisional application No. 61/552,612, filed on Oct. 28, 2011.

(51) Int. Cl.
*A01H 1/04* (2006.01)
*C12N 15/29* (2006.01)
*C12N 15/82* (2006.01)

(52) U.S. Cl.
CPC ......... *C12N 15/8271* (2013.01); *C12N 15/821* (2013.01); *C12N 15/8273* (2013.01)

(58) Field of Classification Search
None
See application file for complete search history.

(56) References Cited

U.S. PATENT DOCUMENTS 5,464,769 A * 11/1995 Attree et al. .............. 800/319
6,281,412 B1 * 8/2001 Murata .................... 800/288
7,253,338 B2    8/2007 Verbruggen

FOREIGN PATENT DOCUMENTS

WO    2012/087903 A2    6/2012

OTHER PUBLICATIONS

Murashige et al. (Physiologia Plantarum, vol. 15 1962, 473-497).*
Atwell et al. (Plants in Action 17.1.3, 1999 (http://plantsinaction.science.uq.edu.au/edition1) retrieved Jul. 21, 2015).*
Kasuga et al. (Nature Biotechnology vol. 17 Mar. 1999, 287-291).*
Munns et al. (Journal of Experimental Botany, doi:10.1093/jxb/erq199, published Jul. 6, 2010, p. 1-9).*
Jose' M. Alonso et al., Genome-Wide Insertional Mutagenesis of *Arabidopsis thaliana*, Science, Aug. 1, 2003, pp. 653-657, vol. 301 and Erratum pp. 1-2.
J. S. Boyer, Plant Productivity and Environment, Science, Oct. 29, 1982, pp. 443-448, vol. 218.
Elizabeth A. Bray et al., Responses to Abiotic Stresses, Biochemistry & Molecular Biology of Plants, edited by Buchanan, Amer Soc Plant Physiologists, 2000, Chapter 22, pp. 1158-1203.
Nicholas Carpita et al., Determination of the Pore Size of Cell Was of Living Plant Cells. Science, Sep. 14, 1979, pp. 1144-1147, vol. 205.
Loren Castaings et al., The nodule inception-like protein 7 modulates nitrate sensing and metabolism in Arabidopsis, The Plant Journal, 2009, pp. 426-435, vol. 57.
M. M. Chaves et al., Mechanisms underlying plant resilience to water deficits: prospects for water-saving agriculture, Journal of Experimental Botany, Nov. 2004, pp. 2365-2384, vol. 55, No. 407.
Hui Chen et al., Osmotic adjustment and plant adaptation to environmental changes related to drought and salinity, Environ Rev, 2010, pp. 309-319, vol. 18.
Nigel M. Crawford et al., Nitrate: Nutrient and Signal for Plant Growth, The Plant Cell, Jul. 1995, pp. 859-868, vol. 7.
Shaoting Du et al., Regulation of nitrate reductase by nitric oxide in Chinese cabbage pakchoi (*Brassica chinensis* L.), Plant, Cell and Environment, 2008, pp. 195-204, vol. 31.
Wolfgang Frank et al., Physcomitrella patens is highly tolerant against drought, salt and osmotic stress, Planta, 2005, pp. 384-394, vol. 220.
Carlos S. Galvan-Ampudia et al., Salt stress signals shape the plant root, Current Opinion in Plant Biology, 2011, pp. 296-302, vol. 14.
Rüdiger Hell, et al., γ-Glutamylcysteine synthetase in higher plants: catalytic properties and subcellular localization, Planta, 1990, pp. 603-612, vol. 180.

(Continued)

*Primary Examiner* — Anne Kubelik
*Assistant Examiner* — Charles Logsdon
(74) *Attorney, Agent, or Firm* — Ei Du Pont De Nemours and Co.

(57) ABSTRACT

Methods are described for the identification of genes useful for conferring tolerance in plants to abiotic stress. Transgenic plants and seeds comprising the stress tolerant genes are also described. Methods to monitor the growth rate of the transgenic plants under stressed or non-stressed conditions are also described.

8 Claims, 28 Drawing Sheets

(56) References Cited

OTHER PUBLICATIONS

James W. Heyser et al., Growth, Water Content, and Solute Accumulation of Two Tobacco Cell Lines Cultured on Sodium Chloride, Dextran, and Polyethylene Glycol, Plant Physiol, 1981, pp. 1454-1459, vol. 68.

Jarmo K. Holopainen et al., Multiple stress factors and the emission of plant VOCs, Trends in Plant Sci, 2010, pp. 176-184, vol. 15(3).

M. Adelaide Iannelli et al., Tolerance to low temperature and paraquat-mediated oxidative stress in two maize genotypes, Journal of Experimental Botany, Apr. 1999, pp. 523-532, vol. 50, No. 333.

Hisashi Koiwa et al., Identification of plant stress-responsive determinants in arabidopsis by large-scale forward genetic screens, Journal of Experimental Botany, 2006, pp. 1119-1128, vol. 57, No. 5.

Maarten Koornneef et al., The genetic and molecular dissection of abscisic acid biosynthesis and signal transduction in Arabidopsis, Plant Physiol Biochem, 1998, pp. 83-89, vol. 36 (1-2).

J. V. Lagerwerff et al., Control of Osmotic Pressure of Culture Solutions with Polyethylene Glycol, Science, 1961, pp. 1486-1487, vol. 133.

Jeffrey Leung et al., Abscisic Acid Signal Transduction, Annu Rev Plant Physiol Plant Mol Biol. 1998, pp. 199-222, vol. 49.

Xia Li et al., Salt-avoidance tropism in Arabidopsis thaliana, Plant Signaling & Behavior, 2008, pp. 351-353, vol. 3.

Jorge Lozano-Juste et al., Enhanced Abscisic Acid-Mediated Responses in nia1nia2noa1-2 Triple Mutant Impaired in NIA/NR- and AtNOA1-Dependent Nitric Oxide Biosynthesis in Arabidopsis, Plant Physiology, Feb. 2010, pp. 891-903, vol. 152.

Arun Lahiri Majumder et al., Osmolyte Regulation in Abiotic Stress, Springer, 2010, pp. 349-370.

Mike J. May et al., Oxidative Stimulation of Glutathione Synthesis in *Arabidopsis thaliana* Suspension Cultures, Plant Physiol, 1993, pp. 621-627, vol. 103.

Ping-Hong Meng et al., Analysis of Natural Allelic Variation Controlling *Arabidopsis thaliana* Seed Germinability in Response to Cold and Dark: Identification of Three Major Quantitative Trait Loci, Molecular Plant, Jan. 2008, pp. 145-154, vol. 1, No. 1.

Ron Mittler, Oxidative stress, antioxidants and stress tolerance, Trends in Plant Sci, Sep. 2002, pp. 405-410, vol. 7, No. 9.

Nicholas P. Money, Osmotic Pressure of Aqueous Polyethylene Glycols, Plant Phyiol, 1989, pp. 766-769, vol. 91.

Patricia Nazoa et al., Regulation of the nitrate transporter gene AtNRT2.1 in *Arabidopsis thaliana*: responses to nitrate, amino acids and developmental stage, 2003, Plant Molecular Biology, pp. 689-703, vol. 52.

J. J. Oertli, The response of Plant Cells to Different Forms of Moisture stress, J. Plant Physiol, 1985, pp. 295-300, vol. 121.

Steven Penfield et al., Cold and Light Control Seed Germination through the bHLH Transcription Factor SPATULA, Current Biology, Nov. 22, 2005, pp. 1998-2006, vol. 15.

Marsha L. Pilgrim et al., Circadian and light-regulated expression of nitrate reductase in Arabidopsis, Plant Molecular Biology, 1993, pp. 349-364, vol. 23.

Mayra Rodriguez et al., Molecular aspects of abiotic stress in plants, Biotecnologia Aplicada, 2005, pp. 1-10, vol. 22.

Louai Salaita et al., Identification and characterization of mutants capable of rapid seed germination at 10 °C from activation-tagged lines of *Arabidopsis thaliana*, Journal of Experimental Botany, Aug. 2005, pp. 2059-2069, vol. 56, No. 418.

Leif Schauser et al., Evolution of NIN-Like Proteins in Arabidopsis, Rice and *Lotus japonicus*, J. Mol Evol, 2005, pp. 229-237, vol. 60.

Kazuo Shinozaki et al., Regulatory network of gene expression in the drought and cold stress responses, Current Opinion in Plant Biology, 2003, pp. 410-417, vol. 6.

Babu Valliyodan et al., Understanding regulatory networks and engineering for enhanced drought tolerance in plants, Current Opinion in Plant Biology, 2006, pp. 189-195, vol. 9.

Basia Vinocur et al., Recent advances in engineering plant tolerances to abiotic stress: achievements and limitations, Current Opinion in Biotechnology, 2005, pp. 123-132, vol. 16.

Paul E. Verslues et al., Methods and concepts in quantifying resistance to drought, salt and freezing, abiotic stresses that affect plant water status, The Plant Journal, 2006, pp. 423-539, vol. 45.

Wangxia Wang et al., Plant responses to drought, salinity and extreme temperatures: towards genetic engineering for stress tolerance, Planta, 2003, pp. 1-14, vol. 218.

Detlef Weigel et al., Activation Tagging in Arabidopsis, Plant Physiology, Apr. 2000, pp. 1003-1013, vol. 122.

Joanna E. Werner et al., Arabidopsis mutants with reduced response to NaCl and osmotic stress, Physiologia Plantarum, 1995, pp. 659-666, vol. 93.

Jack Q. Wilkinson et al., Identification and characterization of a chlorate-resistant mutant of *Arabidopsis thaliana* with mutations in both nitrate reductase structural genes NIA1 and NIA2, Mol Gen Genet, 1993, pp. 289-297, vol. 239.

Kazuko Yamaguchi-Shinozaki et al., Organization of cis-acting regulatory elements in osmotic- and cold-stress-responsive promoters, TRENDS In Plant Science, Feb. 2005, pp. 88-94, vol. 10, No. 2.

International Search Report and Written Opinion of the International Searching Authority—PCT/US2012/062374, mailed Feb. 1, 2013.

Wu et al. SOS1, a Genetic Locus Essential for Salt Tolerance and Potassium Acquisition. The Plant Cell. Apr. 1996. pp. 617-627. vol. 8.

Huazhong Shi et al. The *Arabidopsis thaliana* salt tolerance gene SOS1 encodes a putative Na1yH1 antiporter. PNAS. Jun. 6, 2000. pp. 6896-6901. vol. 97(12).

Manfre et al. Seed Dehydration and the Establishment of Desiccation Tolerance During Seed Maturation is Altered in the *Arabidopsis thaliana* Mutant atem6-1. Plant Cell Physiol. (2009). pp. 243-253 vol. 50(2).

Quesada et al. Genetic Analysis of Salt-Tolerant Mutants in *Arabidopsis thaliana*. Genetics. (Jan. 2000). vol. 154. pp. 421-436.

\* cited by examiner

FIG. 10

| MT | gro_comp | gro_area_p | slope_gro_comp | gro_slope_p | max_comp | max_p | decay_comp | decay_area_p | slope_dec_comp | decay_slope_p |
|----|----------|------------|----------------|-------------|----------|-------|------------|--------------|----------------|---------------|
| A  | +        | 0.066      | +              | 0.667       | +        | 0.902 | +          | 0.783        | -              | 0.652         |
| B  | +        | 0.224      | +              | 0.501       | +        | 0.146 | -          | 0.825        | -              | 0.272         |
| C  | -        | 0.824      | +              | 0.468       | +        | 0.153 | +          | 0.259        | -              | 0.830         |
| D  | +        | 0.000      | +              | 0.191       | +        | 0.000 | +          | 0.184        | -              | 0.069         |
| E  | -        | 0.020      | -              | 0.341       | -        | 0.048 | -          | 0.757        | +              | 0.091         |
| F  | -        | 0.014      | -              | 0.666       | -        | 0.145 | -          | 0.728        | +              | 0.380         |
| G  | +        | 0.841      | -              | 0.901       | -        | 0.787 | -          | 0.107        | -              | 0.327         |
| H  | -        | 0.027      |                | 0.539       |          | 0.204 |            | 0.743        | +              | 0.130         |

FIG. 11A

| gro_comp | gro_area_p | slope_gro comp | gro_slope_p | max_comp | max_p | decay_comp | decay_area_p | slope_dec comp | decay_slope_p |
|---|---|---|---|---|---|---|---|---|---|
| - | 0.291 | + | 0.329 | - | 0.985 | + | 0.041 | + | 0.021 |

FIG. 11B

| Gene | gro_comp | gro_area_p | slope_gro_comp | gro_slope_p | max_comp | max_p | decay_comp | decay_area_p | slope_dec_comp | decay_slope_p | Line ID |
|---|---|---|---|---|---|---|---|---|---|---|---|
| D1511 | - | 0.944 | - | 0.948 | - | 0.673 | + | 0.960 | + | 0.939 | 800153 |
| D1830 | + | 0.001 | + | 0.003 | + | 0.194 | - | 0.960 | - | 0.731 | 800153 |

25% K₂CO₃

60% K₂CO₃

100% K₂CO₃ ddH₂O

40% K₂CO₃

75% K₂CO₃

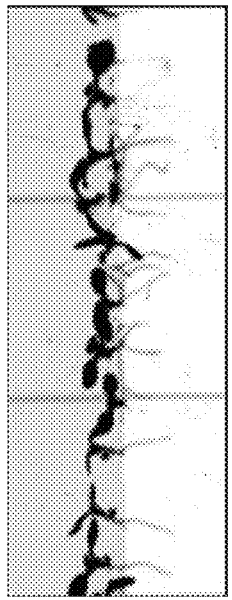
FIG. 17A
WT
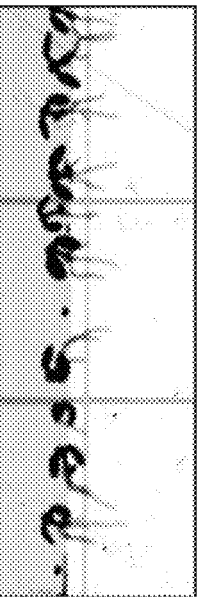
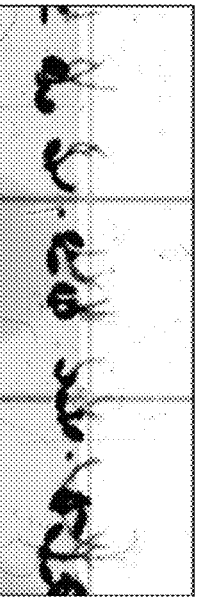
FIG. 17B
Miz1
(hypo)
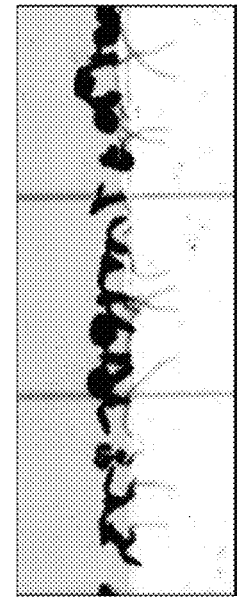
FIG. 17C
001B9
(hypo)
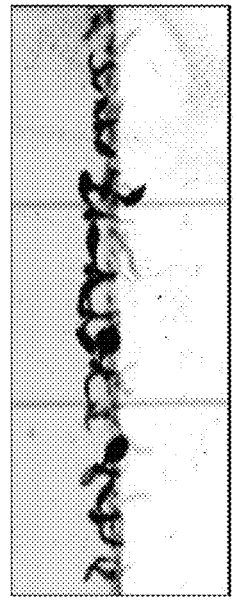
FIG. 17D
002A6
(hyper)
25% $K_2CO_3$
75% $K_2CO_3$

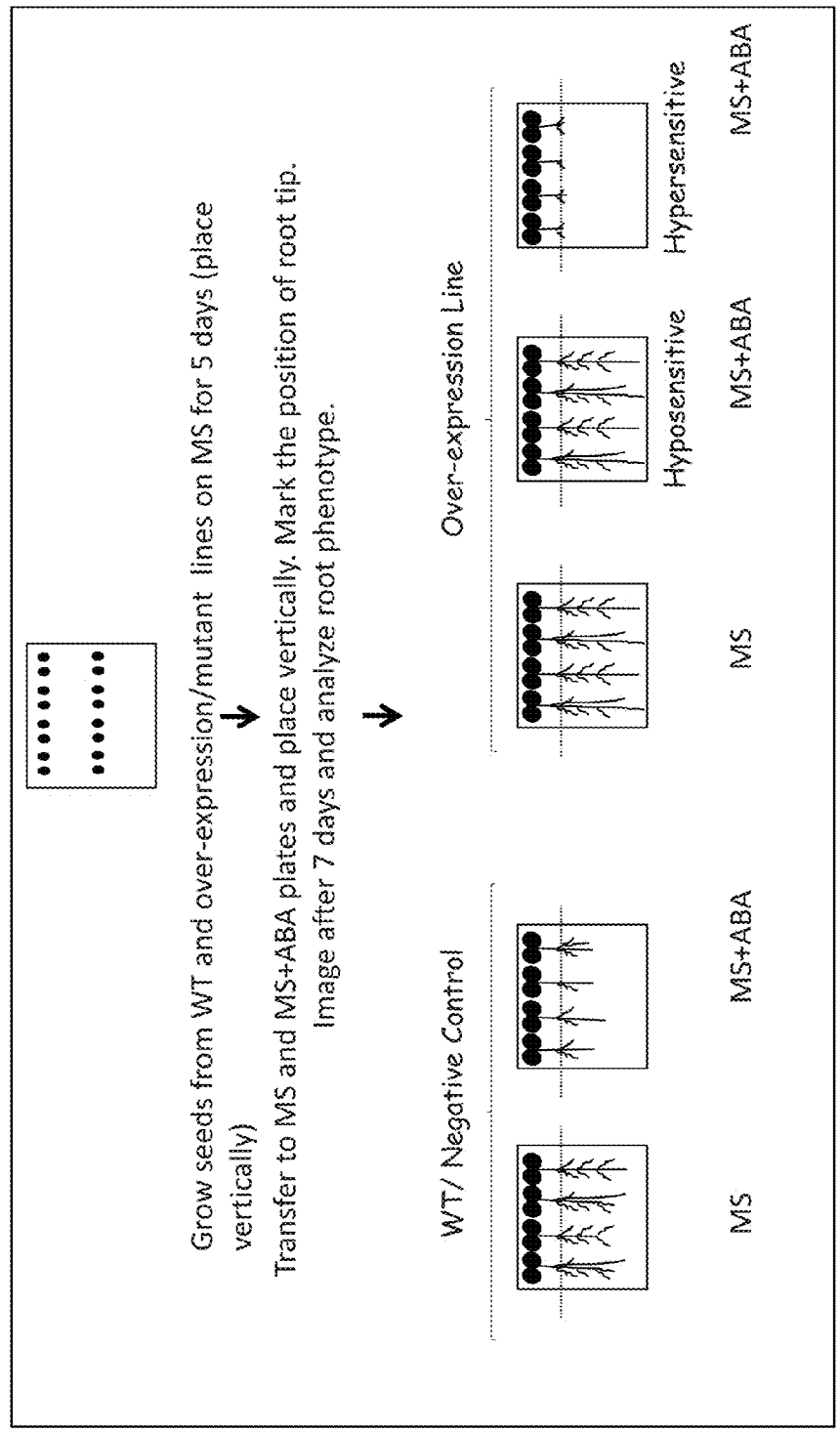

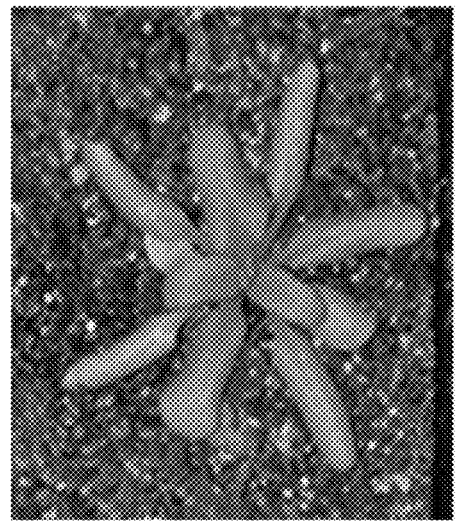
FIG. 23B nia1nia2
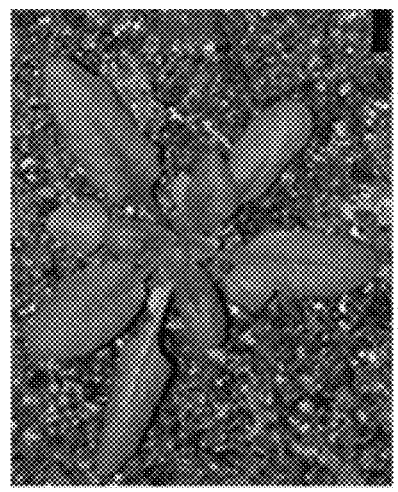
FIG. 23A Col-0

FIG. 24A wt
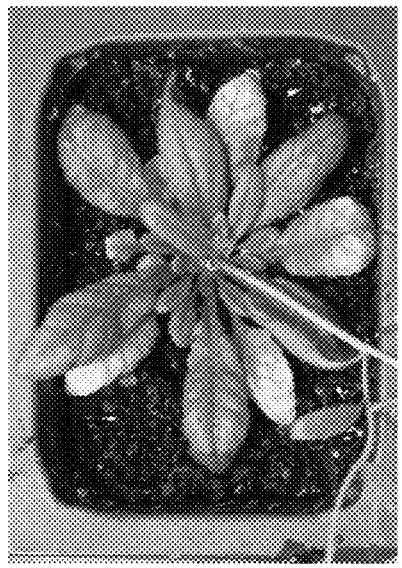
FIG. 24B antimyb

SEQUENCE LISTING

```
<160> NUMBER OF SEQ ID NOS: 17

<210> SEQ ID NO 1
<211> LENGTH: 22
<212> TYPE: DNA
<213> ORGANISM: Artificial Sequence
<220> FEATURE:
<223> OTHER INFORMATION: nlp7 KO fwd primer

<400> SEQUENCE: 1 cagttttct ttagaccgcc ac                                              22

<210> SEQ ID NO 2
<211> LENGTH: 22
<212> TYPE: DNA
<213> ORGANISM: Artificial Sequence
<220> FEATURE:
<223> OTHER INFORMATION: nlp7 KO mutant RP

<400> SEQUENCE: 2
agcagctgag aacacaacag ag                                             22
```

```
<210> SEQ ID NO 3
<211> LENGTH: 22
<212> TYPE: DNA
<213> ORGANISM: Artificial Sequence
<220> FEATURE:
<223> OTHER INFORMATION: nlp7 screen sequence

<400> SEQUENCE: 3
gcgtggaccg cttgctgcaa ct                                              22

<210> SEQ ID NO 4
<211> LENGTH: 26
<212> TYPE: DNA
<213> ORGANISM: Artificial Sequence
<220> FEATURE:
<223> OTHER INFORMATION: 5S4 primer sequence

<400> SEQUENCE: 4
cgtgatttgg gctatattac ggaccc                                          26

<210> SEQ ID NO 5
<211> LENGTH: 20
<212> TYPE: DNA
<213> ORGANISM: Artificial Sequence
<220> FEATURE:
<223> OTHER INFORMATION: 5S6 primer sequence

<400> SEQUENCE: 5
gagggatgca acacgaggac                                                 20

<210> SEQ ID NO 6
<211> LENGTH: 28
<212> TYPE: DNA
<213> ORGANISM: Artificial Sequence
<220> FEATURE:
<223> OTHER INFORMATION: probe sequence

<400> SEQUENCE: 6
tcccatcaga actccgcagt taagcgtt                                        28

<210> SEQ ID NO 7
<211> LENGTH: 497
<212> TYPE: DNA
<213> ORGANISM: Arabidopsis thaliana

<400> SEQUENCE: 7
cccaaatttt gacctttaag tacttttcg ggcattttcg tgatttgggc tatattacgg      60
acccaaaatt acttgttcaa gcattgtttt cgaattttt catgcatcaa agctcgttaa     120
gactagatgg gggatcccta catagcgggt gggacccacg gcgaatggtt catcaactct    180
tcaaaaaaga atatatacga ttgcattgca tatactaacg gatgcgatca taccagcact    240
aatgcaccgg atcccatcag aactccgcag ttaagcgttc ttgggcgaga gtagtactag    300
gatgggtgac ctcccgggaa gtcctcgtgt tgcatccctc tttatatgtt taaccttttt    360
ttttttggtt aaaactttat gactccataa cttttagacc gtgagccaaa cttggcatgt    420 gataccttt cggaaagccc aaagacagcc ctccgacgaa agaagcagga caacttttcc    480
attgactttt tgtcgac                                                   497

<210> SEQ ID NO 8
<211> LENGTH: 24
<212> TYPE: DNA
<213> ORGANISM: Artificial Sequence
<220> FEATURE:
```

-continued

<223> OTHER INFORMATION: primer for soil root mass assay

<400> SEQUENCE: 8
aagtcctcgt gttgcatccc tctt                                           24

<210> SEQ ID NO 9
<211> LENGTH: 24
<212> TYPE: DNA
<213> ORGANISM: Artificial Sequence
<220> FEATURE:
<223> OTHER INFORMATION: primer for soil root mass assay

<400> SEQUENCE: 9
agttgtcctg cttctttcgt cgga                                           24

<210> SEQ ID NO 10
<211> LENGTH: 26
<212> TYPE: DNA
<213> ORGANISM: Artificial Sequence
<220> FEATURE:
<223> OTHER INFORMATION: probe for soil root mass assay

<400> SEQUENCE: 10
accgtgagcc aaacttggca tgtgat                                         26

<210> SEQ ID NO 11
<211> LENGTH: 24
<212> TYPE: DNA
<213> ORGANISM: Artificial Sequence
<220> FEATURE:
<223> OTHER INFORMATION: primer3 for soil root mass assay

<400> SEQUENCE: 11
agttaagcgt tcttgggcga gagt                                           24

<210> SEQ ID NO 12
<211> LENGTH: 24
<212> TYPE: DNA
<213> ORGANISM: Artificial Sequence
<220> FEATURE:
<223> OTHER INFORMATION: primer3 for soil root mass assay

<400> SEQUENCE: 12
atcacatgcc aagtttggct cacg                                           24

<210> SEQ ID NO 13
<211> LENGTH: 26
<212> TYPE: DNA
<213> ORGANISM: Artificial Sequence
<220> FEATURE:
<223> OTHER INFORMATION: probe3 for soil root mass assay

<400> SEQUENCE: 13
gaagtcctcg tgttgcatcc ctcttt                                         26

<210> SEQ ID NO 14
<211> LENGTH: 21
<212> TYPE: DNA
<213> ORGANISM: Artificial Sequence
<220> FEATURE:
<223> OTHER INFORMATION: nia1 genotyping primer

<400> SEQUENCE: 14
tacgacgact cctcaagcga c                                              21

```
<210> SEQ ID NO 15
<211> LENGTH: 21
<212> TYPE: DNA
<213> ORGANISM: Artificial Sequence
<220> FEATURE:
<223> OTHER INFORMATION: nia1 genotyping primer

<400> SEQUENCE: 15
ggctatagat cccgcatcga c                                              21

<210> SEQ ID NO 16
<211> LENGTH: 21
<212> TYPE: DNA
<213> ORGANISM: Artificial Sequence
<220> FEATURE:
<223> OTHER INFORMATION: nia2 genotyping F

<400> SEQUENCE: 16
acggcgtggt tcgttcttac a                                              21

<210> SEQ ID NO 17
<211> LENGTH: 21
<212> TYPE: DNA
<213> ORGANISM: Artificial Sequence
<220> FEATURE:
<223> OTHER INFORMATION: nia2 genotyping R

<400> SEQUENCE: 17
accttcttcg tcggcgagtt c                                              21
```

METHODS FOR THE IDENTIFICATION OF GENES INVOLVED IN ABIOTIC STRESS TOLERANCE IN PLANTS

CROSS REFERENCE TO RELATED APPLICATIONS

This application is a 371 national stage entry of PCT International Application No. PCT/US12/62374, filed Oct. 29, 2012, which claims the benefit of U.S. Provisional Application No. 61/552,612, filed Oct. 28, 2011, now expired, the entire content of each is herein incorporated by reference.

REFERENCE TO SEQUENCE LISTING SUBMITTED ELECTRONICALLY

The official copy of the sequence listing is submitted electronically via EFS-Web as an ASCII formatted sequence listing with a file named "20140424_BB2024USPCT_SequenceListing" created on Apr. 24, 2014 and having a size of 5 kilobytes and is filed concurrently with the specification. The sequence listing contained in this ASCII formatted document is part of the specification and is herein incorporated by reference in its entirety.

FIELD OF THE INVENTION

The field of invention relates to plant molecular biology and biotechnology, and in particular relates to methods for identification of genes useful for conferring tolerance in plants to abiotic stress.

BACKGROUND OF THE INVENTION

Abiotic stress is the primary cause of crop loss worldwide, causing average yield losses of more than 50% for major crops (Boyer, J. S. (1982) Science 218:443-448; Bray, E. A. et al. (2000) In *Biochemistry and Molecular Biology of Plants*, Edited by Buchannan, B. B. et al., *Amer. Soc. Plant Biol.*, pp. 1158-1203). Among the various abiotic stresses, drought, salinity and extreme temperature are major adverse environmental factors that limit crop productivity worldwide. Water stress in its broadest sense encompasses both drought and salinity or osmotic stress. The abiotic stresses of drought, salinity and freezing are linked by the fact that they all decrease the availability of water to plant cells. This decreased availability of water is quantified as a decrease in water potential. Plants resist low water potential and related stresses by various mechanisms such as the following: by modifying water uptake and loss to avoid low water potential; by accumulating solutes and modifying the properties of cell walls to avoid the dehydration induced by low water potential; and by using protective proteins and mechanisms to tolerate reduced water content by preventing or repairing cell damage. Salt stress also alters plant ion homeostasis (Verslues P. E. et al., (2006) *Plant Journal*, 45, 523-539; Koiwa, H. et al. (2006) *J Exp Botany,* 57(5):1119-1128; Rodriguez, M. et al. (2005) *Biotecnologia Aplicada*, 22:1-10).

Drought and salt stress, together with low temperature, are major problems for agriculture because these adverse environmental factors prevent plants from realizing their full genetic potential. Abiotic stress leads to a series of morphological, physiological, biochemical and molecular changes that adversely affect plant growth and productivity. Reviews on the molecular mechanisms of abiotic stress responses and the genetic regulatory networks of drought stress tolerance have been published (Valliyodan, B., and Nguyen, H. T., (2006) *Curr. Opin. Plant Biol.* 9:189-195; Wang, W., et al. (2003) *Planta* 218:1-14; Vinocur, B., and Altman, A. (2005) *Curr. Opin. Biotechnol.* 16:123-132; Chaves, M. M., and Oliveira, M. M. (2004) *J. Exp. Bot.* 55:2365-2384; Shinozaki, K., et al. (2003) *Curr. Opin. Plant Biol.* 6:410-417; Yamaguchi-Shinozaki, K., and Shinozaki, K. (2005) *Trends Plant Sci.* 10:88-94).

The application of transgenic technology, through either over- or under-expression of the transgenes, is a powerful tool for the engineering of stress-tolerant crop plants. Enhancement of resistance against abiotic stresses may also be achieved via traditional breeding, molecular breeding, and transgenic approaches.

There is a need for methods to identify plants resistant to realistic and reproducible stress conditions and which can be applicable to analyzing large numbers of lines. Such methods are important in order to develop more efficient screening procedures for germplasm evaluation and improvement of stress tolerance. Preferably, rapid and reliable screening procedures are desirable. Moreover, under natural conditions, plants rarely experience single stress factors one by one, but are much more likely to be exposed to multiple stresses simultaneously. Few studies have attempted to investigate plant responses under multiple stresses, either in the laboratory or the field. The response of plants to multiple stress combinations cannot always be extrapolated from responses to individual stress factors (Holopainen, J. K. et al. (2010) *Trends Plant Sci.* 15(3):176-184).

SUMMARY OF THE INVENTION

In one embodiment, the present invention relates to methods and compositions for screening, identifying, selecting and isolating plants with increased osmotic stress tolerance. The methods and compositions disclosed in the present invention can be used for identifying and selecting transgenic plant lines and native plant varieties with improved abiotic stress tolerance.

An embodiment of the current invention is a method of selecting seeds or plants from at least one transgenic plant line with increased tolerance to abiotic stress, the method comprising the steps of: (a) obtaining seeds or plants from at least one transgenic plant line comprising at least one heterologous polynucleotide sequence; (b) subjecting the seeds or plants to at least one stress selected from the group consisting of osmotic stress, paraquat stress, triple stress, low temperature stress; low nitrogen stress, drought stress, AT-BSO and high light stress, and high light and low nitrogen stress; and (c) selecting seeds or plants that show an increased percentage seedling emergence or plant tolerance when compared to control seeds or control plants from a control plant line, wherein the control plant line does not comprise the at least one heterologous polynucleotide sequence, and wherein the control seeds or control plants from the control plant line are subjected to the same stress as the seeds or plants from the at least one transgenic plant line to be tested.

Another embodiment of the current invention is a method of selecting a transgenic plant line with increased tolerance to abiotic stress, the method comprising the steps of: (a) obtaining at least one transgenic plant line comprising at least one heterologous polynucleotide sequence; (b) subjecting the plant line to abiotic stress; and (c) selecting the plant line that shows at least one phenotype selected from the group consisting of increased tolerance to triple stress, altered root hydrotropism characteristics, increased percentage germination under cold conditions, increased biomass under cold conditions at grain-filling stage, increased nitrogen stress tolerance, increased paraquat tolerance, altered ABA response, increased tolerance to osmotic stress, increased tolerance to AT-BSO and high light stress, and increased tolerance to high light and low nitrogen stress, when compared to a control plant, wherein the control plant does not comprise the at least one heterologous polynucleotide sequence, and wherein the control plant is subjected to the same stress as the transgenic plant to be tested.

Another embodiment of the current invention is a method for identifying at least one plant with increased tolerance to abiotic stress, the method comprising the steps of: (a) obtaining a population of plants of a single species; (b) subjecting the plants to abiotic stress; (c) selecting the plants that show at least one phenotype selected from the group consisting of increased tolerance to triple stress, altered root hydrotropism characteristics, increased percentage germination under cold conditions, increased paraquat tolerance, altered ABA response and increased tolerance to osmotic stress, when compared to an average of the phenotype exhibited by the plants of step (b).

Another embodiment is a plant obtained by the method of any of the methods described herein, wherein the plants exhibit increased resistance to abiotic stress. The abiotic stress can be selected from a group consisting of osmotic stress, paraquat stress, triple stress, low temperature stress and drought stress. In one embodiment, the plants show at least one phenotype selected from the group consisting of increased tolerance to triple stress, altered root hydrotropism characteristics, increased percentage germination under cold conditions, increased paraquat tolerance, altered ABA response and increased tolerance to osmotic stress.

One embodiment of the current invention is a method of selecting a transgenic plant with an altered response to nitrogen stress, the method comprising the steps of: (a) obtaining an activation-tagged population of plants of a single species; (b) selecting a plant from step (a) that shows at least one phenotype selected from the group consisting of: suppression of an nlp7 knock-out mutant phenotype, suppression of negative regulation of an NRT2.1 promoter by high nitrogen, suppression of an nia1nia2 mutant phenotype, and suppression of an antimyb early senescence phenotype, when compared to a control plant, wherein the control plant does not comprise the activation tag. In one embodiment, the activation tag may comprise four multimerized enhancer elements derived from the Cauliflower Mosaic Virus 35S promoter. In one embodiment, the species of step (a) may be *Arabidopsis*, and the phenotype of step (b) may be selected from the group consisting of: suppression of an *Arabidopsis* nlp7 knock-out mutant phenotype, suppression of negative regulation of an *Arabidopsis* NRT2.1 promoter by high nitrogen, suppression of an *Arabidopsis* nia1nia2 mutant phenotype, and suppression of an *Arabidopsis* antimyb early senescence phenotype. The method may further comprise isolation of the polynucleotide sequence that is activation-tagged. The method may further comprise transformation of a plant with the isolated polynucleotide sequence into the appropriate background to confirm the phenotype.

One embodiment of the current invention is a method of identifying a polynucleotide sequence involved in nitrogen stress, the method comprising the steps of: (a) obtaining at least one transgenic plant comprising a promoter functional in a plant cell operably linked to an isolated polynucleotide sequence; (b) selecting a plant from step (a) that shows at least one phenotype selected from the group consisting of: suppression of an nlp7 knock-out mutant phenotype, suppression of negative regulation of an NRT2.1 promoter by high nitrogen, suppression of an nia1nia2 mutant phenotype, and suppression of an antimyb early senescence phenotype, when compared to a control plant, wherein the control plant does not comprise the at least one heterologous polynucleotide sequence. In one embodiment, the species of step (a) may be *Arabidopsis*, and the phenotype of step (b) may be selected from the group consisting of: suppression of an *Arabidopsis* nlp7 knock-out mutant phenotype, suppression of negative regulation of an *Arabidopsis* NRT2.1 promoter by high nitrogen, suppression of an *Arabidopsis* nia1nia2 mutant phenotype, and suppression of an *Arabidopsis* antimyb early senescence phenotype. In one embodiment, the promoter of step (a) may be a constitutive, a tissue-specific, or an inducible promoter or a combination of any of these. In one embodiment, the promoter may be a Cauliflower Mosaic Virus 35S promoter.

In one embodiment, the invention encompasses the plants obtained by the method of any of the above embodiments wherein the plants show increased growth rate under non-stressed conditions. The increased growth rate may be an increase in root growth rate. The increased root growth rate may be measured in the presence or absence of ABA.

In one embodiment, any of the assays described herein can be done in a high throughput manner. In additional embodiments, any of the assays described herein can be used for screening at least 20, 50, 100, 200, 300, 400, 500 or 1000 plants at one time.

In another embodiment, the invention encompasses the seeds, progeny plants and subsequent generations of plants identified using the methods and compositions disclosed herein.

BRIEF DESCRIPTION OF THE DRAWINGS

The invention can be more fully understood from the following detailed description and the accompanying drawings which form a part of this application.

FIG. 3A shows the germination curves for Line ID Nos. 18, 25, 28 and 74. FIG. 3B shows the germination curve for Line ID Nos. 56, 58, 61 and 64.

FIG. 10 shows a table for the triple stress assay.

FIG. 11A-FIG. 11B show tables for the triple stress assay.

FIG. 17A-FIG. 17D show results of the root hydrotropism screen.

FIG. 21 shows an overall schematic representation of ABA/Root assay.

FIG. 23A-FIG. 23B show a comparison between the wt Col-0 and nia1nia2 *Arabidopsis* plants.

FIG. 24A-FIG. 24B show a comparison between the wt Col-0 and antimyb *Arabidopsis* plants.

Figure 1:
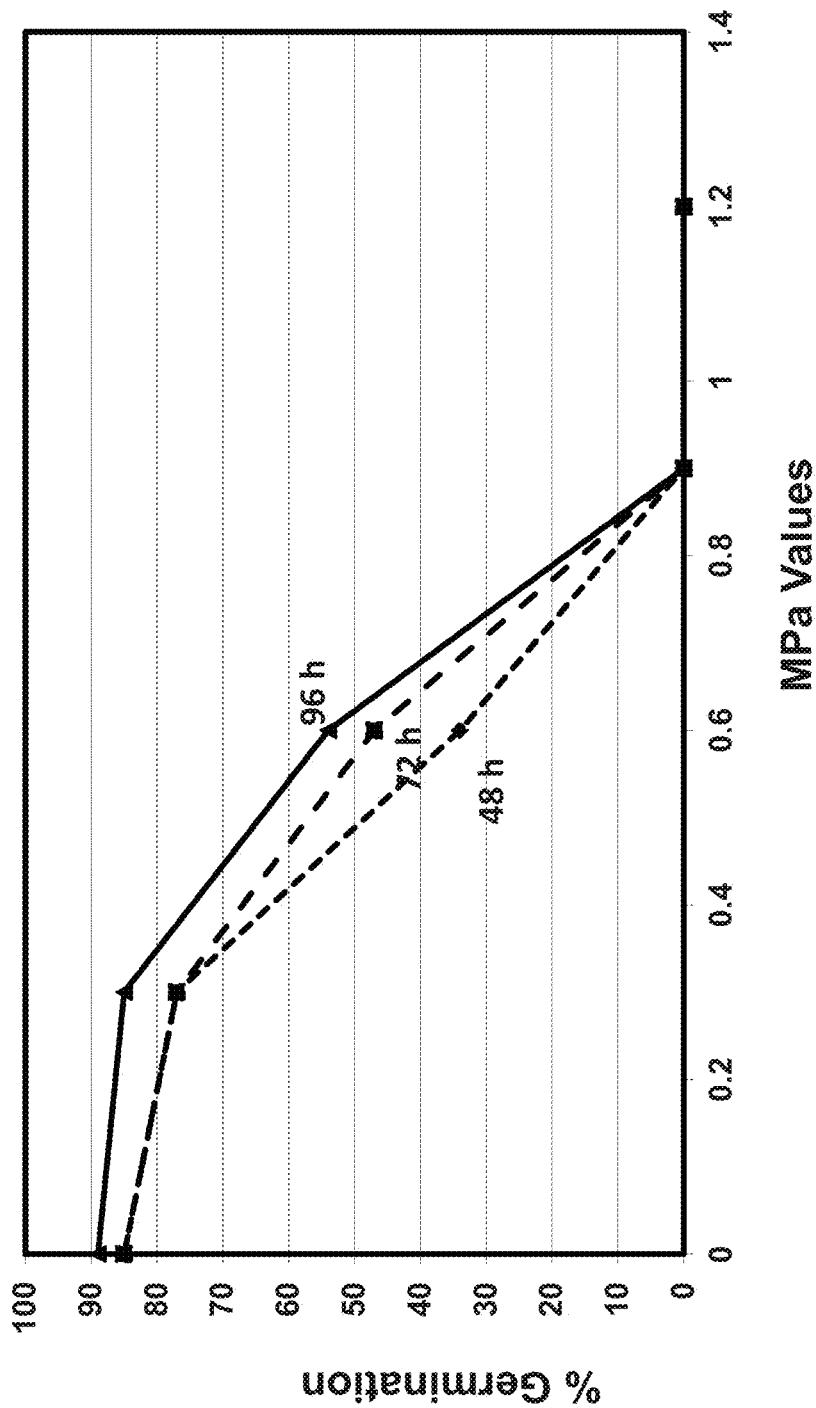
FIG. 1 is a graph showing the percentage germination curve for *Arabidopsis* wild type seeds at various quad concentrations at 48, 72 and 96 hours of seed inoculation. The quad stress used the following conditions: NaCl (62.5 mM), sorbitol (125 mM), mannitol (125 mM), and PEG (10%).

SEQ ID NOs:1, 2 and 3 are the primer sequences used for genotyping of the seedlings of the SALK_026134 line that contains a T-DNA insertion in the second exon of the At4g24020 gene.

SEQ ID NOs:4-6 are the primer and probe sequences used in the soil root mass assay.

SEQ ID NO:7 is the sequence of the 5S rRNA region used in the soil root mass assay.

SEQ ID NOs:8-13 are the sequences of additional primer and probe sequences that can be used for the soil root mass assay.

SEQ ID NOs:14 and 15 are the sequences of the primers used for genotyping the NIA1 gene (At1g77760) in the nia1nia2 knockout mutant line procured from the *Arabidopsis* Biological Resource Center, stock # CS2356.

SEQ ID NOs:16 and 17 are the sequences of the primers used for genotyping the NIA2 gene (At1g37130) in the nia1nia2 knockout mutant line procured from the *Arabidopsis* Biological Resource Center, stock # CS2356.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms and abbreviations are used. The following definitions are provided.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

"Coding region" refers to a polynucleotide sequence that when transcribed, processed, and/or translated results in the production of a polypeptide sequence.

An "Expressed Sequence Tag" ("EST") is a DNA sequence derived from a cDNA library and therefore is a sequence which has been transcribed. An EST is typically obtained by a single sequencing pass of a cDNA insert.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "full complement" and "full-length complement" are used interchangeably herein, and refer to a complement of a given nucleotide sequence, wherein the complement and the nucleotide sequence consist of the same number of nucleotides and are 100% complementary.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

The recombinant construct may comprise a gene fusion with a non-coding or regulatory region fused to another non-coding sequence, a non-coding sequence recombined to a protein-coding polynucleotide, or two coding regions recombined as to make a single continuous open-reading frame encoding a fusion protein.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "abiotic stress" as used in the present invention refers to any adverse effect on metabolism, growth or viability of the cell, tissue, seed, organ or whole plant which is produced by a non-living or non-biological environmental stressor.

Abiotic stress may be at least one condition selected from the group consisting of: osmotic stress, drought, water deprivation, flood, high light intensity, very high light intensity, high temperature, low temperature, salinity, etiolation, defoliation, heavy metal toxicity, anaerobiosis, nutrient deficiency, nutrient excess, UV irradiation, atmospheric pollution (e.g., ozone) and exposure to chemicals (e.g., paraquat) that induce production of reactive oxygen species (ROS). The nutrient may be nitrogen or phosphorus, for example.

Methods and compositions to identify genes that confer increased tolerance to adverse growing conditions or to the imposed stress conditions are described herein.

As used herein, the terms "stress tolerant", "stress resistant", "tolerant" or "resistant" are used interchangeably herein, and refer to a plant, that, when exposed to a stress condition, shows less of an effect, or no effect, in response to the condition as compared to a corresponding control (or reference) plant, wherein the control plant is exposed to the same stress condition as the test plant.

The terms "stress tolerance" or "stress resistance" as used herein refers to a measure of a plants ability to grow under stress conditions that would detrimentally affect the growth, vigor, yield, and size, of a "non-tolerant" plant of the same species. Stress tolerant plants grow better under conditions of stress than non-stress tolerant plants of the same species. For example, a plant with increased growth rate, compared to a plant of the same species and/or variety, when subjected to stress conditions that detrimentally affect the growth of another plant of the same species would be said to be stress tolerant. A plant with "increased stress tolerance" can exhibit increased tolerance to one or more different stress conditions.

"Increased stress tolerance" of a plant is measured relative to a reference or control plant, and is a trait of the plant to survive under stress conditions over prolonged periods of time, without exhibiting the same degree of physiological or physical deterioration relative to the reference or control plant grown under similar stress conditions. Typically, when a transgenic plant comprising a recombinant DNA construct or suppression DNA construct in its genome exhibits increased stress tolerance relative to a reference or control plant, the reference or control plant does not comprise in its genome the recombinant DNA construct or suppression DNA construct.

"Stress tolerance activity" of a polypeptide indicates that over-expression of the polypeptide in a transgenic plant confers increased stress tolerance to the transgenic plant relative to a reference or control plant. For examples, a polypeptide with "triple stress tolerance activity" indicates that over-expression of the polypeptide in a transgenic plant confers increased triple stress tolerance to the transgenic plant relative to a reference or control plant. A polypeptide with "paraquat stress tolerance activity" indicates that over-expression of the polypeptide in a transgenic plant confers increased paraquat stress tolerance to the transgenic plant relative to a reference or control plant.

All numbers used herein should be modified by the term "about". The term "about" means that the number can vary, in either direction, by up to 10 percent and still retain the same meaning. For example, a 1 M solution should include all solutions of that type less than, and including, 1.1 M and more than, and including, 0.9 M. For example, a percentage can also be modified, 10% is inclusive of all percentages from 9% to 11%. Terms defined by the adjective "exactly" are not defined by the term "about".

"Drought" refers to a decrease in water availability to a plant that, especially when prolonged, can cause damage to the plant or prevent its successful growth (e.g., limiting plant growth or seed yield).

The terms "drought", "drought stress", "low water availability", "water stress" and "reduced water availability" are used interchangeably herein, and refer to less water availability to the plant than what is required for optimal growth and productivity.

"Drought tolerance" is a trait of a plant to survive under drought conditions over prolonged periods of time without exhibiting substantial physiological or physical deterioration.

"Drought tolerance activity" of a polypeptide indicates that over-expression of the polypeptide in a transgenic plant confers increased drought tolerance to the transgenic plant relative to a reference or control plant.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct or suppression DNA construct in its genome exhibits increased drought tolerance relative to a reference or control plant, the reference or control plant does not comprise in its genome the recombinant DNA construct or suppression DNA construct.

"Triple stress" as used herein refers to the abiotic stress exerted on the plant by the combination of drought stress, high temperature stress and high light stress.

The terms "heat stress" and "temperature stress" are used interchangeably herein, and are defined as where ambient temperatures are hot enough for sufficient time that they cause damage to plant function or development, which might be reversible or irreversible in damage. "High temperature" can be either "high air temperature" or "high soil temperature", "high day temperature" or "high night temperature, or a combination of more than one of these.

In one embodiment of the invention, the ambient temperature can be in the range of 30° C. to 36° C. In one embodiment of the invention, the duration for the high temperature stress could be in the range of 1-16 hours.

"High light intensity" and "high irradiance" and "light stress" are used interchangeably herein, and refer to the stress exerted by subjecting plants to light intensities that are high enough for sufficient time that they cause photoinhibition damage to the plant.

In one embodiment of the invention, the high light intensity can be in the range of 250 µE to 450 µE. In one embodiment of the invention, the duration for the high light intensity stress could be in the range of 12-16 hours.

"Very high light intensity" and "very high irradiance" and "severe light stress" are used interchangeably herein and refer to the stress exerted by subjecting plants to light intensities that are higher than that exerted by high light intensity.

In one embodiment, the very high light intensity can be in the range of 450 µE-600 µE.

"Triple stress tolerance" is a trait of a plant to survive under the combined stress conditions of drought, high temperature and high light intensity over prolonged periods of time without exhibiting substantial physiological or physical deterioration.

"Paraquat" is an herbicide that exerts oxidative stress on the plants. Paraquat, a bipyridylium herbicide, acts by intercepting electrons from the electron transport chain at PSI. This reaction results in the production of bipyridyl radicals that readily react with dioxygen thereby producing superoxide. Paraquat tolerance in a plant has been associated with the scavenging capacity for oxyradicals (Lannelli, M. A. et al. (1999) *J Exp Botany*, Vol. 50, No. 333, pp. 523-532). Paraquat resistant plants have been reported to have higher tolerance to other oxidative stresses as well.

"Paraquat stress" is defined as stress exerted on the plants by subjecting them to paraquat concentrations ranging from 0.03 to 0.3 µM.

Many adverse environmental conditions such as drought, salt stress, and use of herbicide promote the overproduction of reactive oxygen species (ROS) in plant cells. ROS such as singlet oxygen, superoxide radicals, hydrogen peroxide ($H_2O_2$), and hydroxyl radicals are believed to be the major factor responsible for rapid cellular damage due to their high reactivity with membrane lipids, proteins, and DNA (Mittler, R. (2002) *Trends Plant Sci* 7(9):405-410).

As used herein, the terms "cold stress", "chilling stress" and "low temperature stress" are used interchangeably, and is defined herein as stress due to a lower temperature such that a given plant species will be adversely affected. In specific conditions, "cold stress" can mean chilling of seeds or plants below 15° C. The stress can be applied at different stages of plant development. Examples of stages at which the chilling stress can be applied include, but are not limited to, seed germination and the grain filling stage.

Low temperature often affects plant growth and crop productivity, causing significant crop losses. Plants differ in their tolerance to chilling (0-15° C.) and freezing (<0° C.) temperatures.

Plant species vary in their capacity to tolerate low temperatures. Chilling-sensitive plant species, including many agronomically important species, can be injured by cold, above-freezing temperatures (Salaita, L. et al. (2005) *J Exp Botany*, 56(418):2059-2069; Penfield, S. et al. (2005) *Current Biology*, 15:1998-2006; Meng, P-H. et al. (2008) *Molecular Plant* 1(1):145-154).

Plant seeds vary considerably in their ability to germinate under cold conditions. Plants that tolerate cold during germination are characterized by their ability to remain viable or recover quickly from low temperature conditions.

The terms "percentage germination" and "percentage seedling emergence" are used interchangeably herein, and refer to the percentage of seeds that germinate, when compared to the total number of seeds being tested.

"Germination" as used herein refers to the emergence of the radicle.

The term "radicle" as used herein refers to the embryonic root of the plant, and is terminal part of embryonic axis. It grows downward in the soil, and is the first part of a seedling to emerge from the seed during the process of germination.

The range of stress and stress response depends on the different plants which are used for the invention, i.e., it varies for example between a plant such as wheat and a plant such as *Arabidopsis*.

Osmosis is defined as the movement of water from low solute concentration to high solute concentration up a concentration gradient.

"Osmotic pressure" of a solution as defined herein is defined as the pressure exerted by the solute in the system. A solution with higher concentration of solutes would have higher osmotic pressure. All solutes exhibit osmotic pressure. Osmotic pressure increases as concentration of the solute increases.

The osmotic pressure exerted by 250 mM NaCl (sodium chloride) is 1.23 MPa (megapascals) (Werner, J. E. et al. (1995) *Physiologia Plantarum* 93: 659-666).

As used herein, the term "osmotic stress" refers to any stress which is associated with or induced by elevated concentrations of osmolytes and which result in a perturbation in the osmotic potential of the intracellular or extracellular environment of a cell. The term "osmotic stress" as used herein refers to stress exerted when the osmotic potential of the extracellular environment of the cell, tissue, seed, organ or whole plant is increased and the water potential is lowered and a substance that blocks water absorption (osmolyte) is persistently applied to the cell, tissue, seed, organ or whole plant.

With respect to the osmotic stress assay, the term "quad" as used herein refers to four components that impart osmotic stress. A "quad assay" or "quad media", as used herein, would therefore comprise four components that impart osmotic stress, e.g., sodium chloride, sorbitol, mannitol and PEG.

An increase in the osmotic pressure of the media solution would result in increase in osmotic potential. Examples of conditions that induce osmotic stress include, but are not limited to, salinity, drought, heat, chilling and freezing.

In one embodiment of the invention the osmotic pressure of the media for subjecting the plants to osmotic stress is from 0.4-1.23 MPa. In other embodiments of the invention, the osmotic pressure of the media for subjecting the plants to osmotic stress is 0.4 MPa, 0.5 MPa, 0.6 MPa, 0.7 MPa, 0.8 MPa, 0.9 MPa, 1 MPa, 1.1 MPa, 1.2 MPa or 1.23 MPa. In other embodiments of the invention, the osmotic pressure of the media for subjecting the plants to osmotic stress is at least 0.4 MPa, 0.5 MPa, 0.6 MPa, 0.7 MPa, 0.8 MPa, 0.9 MPa, 1 MPa, 1.1 MPa, 1.2 MPa or 1.23 MPa. In another embodiment of the invention, the osmotic pressure of the media for subjecting the plants to osmotic stress is 1.23 MPa The terms "solute" and "osmolytes" are used interchangeably herein and refer to substances that lower the water potential. Examples of such substances include, but are not limited to, ionic osmolytes and nonionic osmolytes.

Ionic solutes can be water soluble inorganic solutes such as sodium chloride (NaCl). Examples of water soluble inorganic solutes include, but are not limited to, NaCl, KCl (potassium chloride), LiCl (lithium chloride), CsCl (cesium chloride), RbCl (Rubidium chloride) and CaCl2 (calcium chloride), sodium sulfate, magnesium sulfate, calcium sulfate, sodium chloride, magnesium chloride, calcium chloride, potassium chloride, etc., salts of agricultural fertilizers and salts associated with alkaline or acid soil conditions (Werner J. E. et al. (1995) *Physiologia Plantarum* 93: 659-666; U.S. Pat. No. 7,253,338).

Examples of non-ionic osmolytes include, but are not limited to, sugars, sugar alcohols, and high molecular weight polymeric osmolytes.

Any sugar alcohol that is mostly metabolically inert can be used as an osmolyte for the methods described in the current invention. Examples of sugar alcohols that can be used as an osmolyte for the methods described in the current invention include, but are not limited to, mannitol, sorbitol, xylitol, lactitol and maltitol. Combination of two or more sugar alcohols may also be used.

Examples of other sugars that can be used as an osmolyte for the methods described in the current invention include, but are not limited to, melibiose and sucrose.

"High-molecular weight polymeric solutes" as used herein refer to polymeric solutes that largely do not permeate into the plant cells. Examples of high-molecular weight polymeric solutes that can be used for lowering the water potential, include, but are not limited to, polyethylene glycol (PEG), polypropylene glycols and dextran (U.S. Pat. No. 5,464,769A; Money N. P., *Plant Physiol.* (1989) 91:766-769; Lagerwerff, J. V. et al. (1961) *Science* 133:1486-1487; Heyser, J. E. et al. (1981) *Plant Physiol.* 68:1454-1459). Polyethylene glycol (PEG) is a polymer produced in a range of molecular weights. PEG of molecular weight 6000 or above largely cannot enter the pores of plant cells (Verslues, P. E. et al. (2006) *Plant Journal* 45:523-539; Carpita, N. et al., (1979) *Science* 205:1144-1147; Oertli, J. J. (1985) *J. Plant Physiol.* 121:295-300).

PEG of higher molecular weight (>=3000) can be used for the methods described in the current invention. In an embodiment, PEG having a molecular weight between 3000 and 35000 can be used for the methods disclosed in the current invention. In one embodiment, PEG 4000, PEG 6000, PEG 8000 can be used for the methods described in the current invention. In one embodiment, PEG of molecular weight higher than 8000 can be used for the methods described herein.

The terms "tolerant to osmotic stress", "resistant to osmotic stress" and "osmotically tolerant" are used interchangeably herein, and refer to a plant, that when exposed to an osmotic stress condition, shows less of an effect, or no effect, in response to the condition as compared to a corresponding control (or reference plant), wherein the control plant is exposed to the same osmotic stress condition as the test plant.

A plant identified using the methods disclosed in the current invention exhibits increased tolerance to osmotic stress when grown on a medium which contains a higher content of osmolytes compared to a medium the corresponding reference plant is capable of growing on.

"Nitrogen limiting conditions" refers to conditions where the amount of total available nitrogen (e.g., from nitrates, ammonia, or other known sources of nitrogen) is not sufficient to sustain optimal plant growth and development. One skilled in the art would recognize conditions where total available nitrogen is sufficient to sustain optimal plant growth and development. One skilled in the art would recognize what constitutes sufficient amounts of total available nitrogen, and what constitutes soils, media and fertilizer inputs for providing nitrogen to plants. Nitrogen limiting conditions will vary depending upon a number of factors, including but not limited to, the particular plant and environmental conditions.

Nitrogen is the most abundant and essential nutrient for plants and frequently limits plant growth and development (Crawford (1995) *Plant Cell* 7(7):859-868). Nitrate is the predominant form of soil nitrogen available to plants. After being taken up by plants, nitrate is reduced to ammonia for incorporation into amino acids. The pathway of nitrate assimilation has already been clearly determined. The first step committed in the nitrate assimilation in plants is the reduction of nitrate to nitrite by nitrate reductase (NR; EC 1.6.6.1) through catalyzing the transfer of two electrons from nicotinamide-adenine dinucleotide phosphate [NAD (P)H] to nitrite, which is further reduced in the chloroplast by reduced ferredoxin and nitrite reductase (NiR; EC 1.7.7.1). NR is the rate-limiting step in the nitrate assimilation pathway (Pilgrim et al., (1993) *Plant Mol. Biol.* 23:349-364; Du et al., (2008) *Plant Cell Environ.* 31:195-204). In *Arabidopsis*, two different genes NIA1 and NIA2 encoding NR have been identified many years ago.

A plant selected using the methods of the present invention can grow better, can have higher yields and/or can produce more seeds under stress conditions, as compared to a control plant. A plant selected using the methods disclosed in the current invention is capable of substantially normal growth under environmental conditions where the corresponding reference plant shows reduced growth, metabolism or viability, or increased male or female sterility.

"Root hydrotropism" as used herein refers to the response of plant roots to water availability by redirecting primary root growth towards a higher water potential or moisture. Water potential is determined by the moisture content as well as the salinity. Hydrotropic growth of roots is an important trait for plants to actively find water and to optimize their fitness under adverse conditions such as drought (Li, X. et al. (2008) *Plant Signaling & Behavior* 3:351-353; Galvan-Ampudia, C. S. et al. (2011) *Curr Opin Plant Biol* 14:296-302).

A plant exhibiting "altered root hydrotropism" exhibits altered root hydrotropism in response to water availability or osmolytes, when compared to a control plant that is subjected to the same conditions.

A plant exhibiting "hypo-hydrotropism" exhibits lower magnitude of response than a control plant, or requires enhanced magnitude of stimulus than the control plant to exhibit the same root hydrotropic phenotype as the control plant.

A plant exhibiting "hyper-hydrotropism" exhibits higher magnitude of response than a control plant, or requires lower magnitude of stimulus than the control plant to exhibit the same root hydrotropic phenotype as the control plant.

Abscisic acid (ABA), a plant hormone, is known to be involved in important plant physiological functions, such as acquisition of stress response and tolerance to drought and low temperature, as well as seed maturation, dormancy, germination etc. (M. Koornneef et al., *Plant Physiol. Bio-* chem. 36:83 (1998); J. Leung & J. Giraudat, *Annu. Rev. Plant. Physiol. Plant. Mol. Biol.* 49:199 (1998)). Plants subjected to environmental stresses such as drought and low temperature are thought to acquire the ability to adapt to environmental stresses due to the in vivo synthesis of ABA, which causes various changes within the plant cells. A number of genes have been identified that are induced by ABA. This suggests that ABA-induced tolerance to adverse environmental conditions is a complex multigenic event.

The terms "altered ABA response" and "altered ABA sensitivity" are used interchangeably herein, and, as used herein, by these terms it is meant that a plant or plant part exhibits an altered ABA induced response, when compared to a control plant, and includes both hypersensitivity and hyposensitivity to ABA.

"Hypersensitivity" or "enhanced response" of a plant to ABA means that the plant exhibits ABA induced phenotype at lower concentration of ABA than the control plant, or exhibits increased magnitude of response than the control plant when subjected to the same concentration of ABA as the control plant.

"Hyposensitivity" or "decreased response" of a plant to ABA means that the plant exhibits ABA induced phenotype at higher concentration of ABA than the control plant, or exhibits decreased magnitude of response than the control plant when subjected to the same concentration of ABA as the control plant.

Sensitivity to ABA can be assessed at various plant developmental stages. Examples include, but are not limited to, germination, cotyledon expansion, expansion of the first true leaf, or developmental arrest in the seedling stage. Moreover, the concentration of ABA at which sensitivity is observed varies in a species dependent manner. For example, transgenic *Arabidopsis thaliana* will demonstrate sensitivity at a lower concentration than observed in *Brassica* or soybean.

"Nitrogen stress tolerance" is a trait of a plant and refers to the ability of the plant to survive under nitrogen limiting conditions.

"Increased nitrogen stress tolerance" of a plant is measured relative to a reference or control plant, and means that the nitrogen stress tolerance of the plant is increased by any amount or measure when compared to the nitrogen stress tolerance of the reference or control plant.

A "nitrogen stress tolerant plant" is a plant that exhibits nitrogen stress tolerance. A nitrogen stress tolerant plant is preferably a plant that exhibits an increase in at least one agronomic characteristic relative to a control plant under nitrogen limiting conditions.

Activation tagging can be utilized to identify genes with the ability to affect a trait. This approach has been used in the model plant species *Arabidopsis thaliana* (Weigel et al., 2000 *Plant Physiol.* 122:1003-1013). Insertions of transcriptional enhancer elements can dominantly activate and/or elevate the expression of nearby endogenous genes. This method can be used to identify genes of interest for a particular trait, e.g., genes that when placed in an organism as a transgene can alter that trait.

*Arabidopsis* NIN-like protein 7 (NLP-7) is a transcription factor that is involved in regulation of nitrate assimilation in higher plants. The *Arabidopsis* genome encodes nine NLPs (NIN-like proteins (NLPs) characterized by the highly homologous RWP-RK domain that is predicted to be a DNA-binding and dimerization domain (Castaings et al. (2009) *Plant J.* 57:426-435). Another conserved domain shows strong homology to the PB1 domain, a protein-protein interaction domain enabling heterodimerization between PB1 domain-containing proteins (Schauser et al., (2005) *J Mol Evol* 60:229-237). Castings et al. have reported that *Arabidopsis thaliana* NIN-like protein 7 (NLP7) knockout mutants constitutively show several features of nitrogen-starved plants.

Nitrate is a major nitrogen source for land plants and also acts as a signaling molecule that induces changes in growth and gene expression. The NRT2.1 gene codes for a high-affinity nitrate transporter in *Arabidopsis thaliana*. Nazoa et al. (*Plant Mol. Biol.* 52: 689-703, 2003) have shown that the NRT2.1 gene codes for a major component of the inducible high-affinity transport system for nitrate, which is spatially and developmentally controlled at the transcriptional level. NRT2.1 expression has been shown to be induced by local nitrate supply and repressed by systemic feedback signals exerted by high N status, such as amino acids.

The terms "aminotriazole", "AT", and "3-amino-1,2,4-triazole" are used interchangeably herein. AT is a catalase inhibitor and is used to induce oxidative stress (May, M. J. and Leaver C. J. (1993) *Plant Physiol.* 103: 621-627).

Smith et al. have shown that inhibition of catalase by aminotriazole leads to leakage of hydrogen peroxide from the peroxisomes and to a stimulation of GSH synthesis.

The terms "Buthionine sulphoximine", "BSO", and "L-buthionine-[S,R]-sulfoximine" are used interchangeably herein. BSO is a specific inhibitor of γ-glutamylcysteine synthetase (γ-ECS). The pathway of glutathione synthesis is conserved in all organisms and involves two enzymes, γ-glutamylcysteine synthetase (γ-ECS) and glutathione synthetase (GSH-S) (May, M. J. and Leaver C. J. (1993) *Plant Physiol.* 103: 621-627).

The terms "glutathione", "GSH" and "reduced glutathione" are used interchangeably herein.

GSH is the most abundant non-protein thiol in cells, and its nucleophilic activity is exploited in several stress response pathways to detoxify active oxygen species, xenobiotics and certain heavy metals. It an important antioxidant in all aerobic organisms and plays a crucial role in the defense against activated oxygen species arising as by-products of metabolism. In plants, the potential for the production of activated oxygen species is greatly enhanced by a wide range of environmental stresses, and it is thought that the ensuing damage results from the accumulation of these species to levels exceeding the antioxidant capacities of the cell. GSH is likely to play an important role in stress tolerance and has been implicated in the adaptation of plants to environmental stresses such as drought, atmospheric pollution, and extremes of temperature; furthermore, its synthesis is induced in response to these stresses. GSH and its oxidized form, GSSG, form one of a series of redox couples that transfer reducing equivalents from NADPH to active oxygen species.

GSH is synthesized by a two-step process. The first step is catalyzed by γ-glutamylcysteine synthetase (Hell and Bergmann (1990) *Planta* 180:603-612) and results in the production of γ-glutamylcysteine; the second step is catalyzed by GSH synthetase, produces GSH through the addition of Gly.

In an embodiment of the invention, the plant identified and selected by the methods and compositions disclosed, are tolerant to at least one kind of abiotic stress, or to at least 2, 3, 4, 5, 6, 7, 8, 9, or at least 10 kinds of abiotic stresses.

The "cotyledon" is a terminally differentiated structure that functions in the accumulation of storage reserves that are consumed by the germinating seedling after seed dormancy ends.

The term "percentage greenness" or "% greenness" refers herein to the percentage of seedlings that have totally green leaves, wherein the percentage is calculated with respect to the total number of seedlings being tested. "Percentage greenness" as referred to herein is scored as the percentage of seedlings with green leaves compared to seedlings with yellow, brown or purple leaves. "Percentage greenness" can be scored at 1-leaf or 2-leaf stage for seedlings of a monocot plant, wherein the first and second leaves are true leaves. "Percentage greenness" as used herein, can be scored at 3- or 4-leaf stage for seedlings of a dicot plant, wherein two of the leaves are cotyledonary leaves, and the third and fourth leaves are true leaves. To calculate % greenness in the seedlings of a dicot plant, any seedling with any yellow or brown streaks on any of the four leaves is not considered green. To calculate % greenness in the seedlings of a monocot plant, any seedling with any yellow or brown streaks on any of the first or second leaves is not considered green. In one embodiment of the current invention, "percentage greenness" is calculated when all the seedlings are subjected to osmotic stress.

"True leaves" as used herein refer to the non-cotyledonary leaves of the plant or the seedling.

The term "percentage leaf emergence" or "% leaf emergence" refers herein to the percentage of seedlings that had fully expanded 1-, 2- or 3-true leaves, wherein the percentage is calculated with respect to the total number of seedlings being tested. "Percentage leaf emergence" can be scored as the appearance of fully expanded first two true leaves for the seedlings of a dicot plant. "Percentage leaf emergence" can be scored as the appearance of fully expanded first 1- or 2-true leaves for the seedlings of a monocot plant. In one embodiment of the current invention, the "percentage leaf emergence" is calculated when all the seedlings are subjected to osmotic stress.

The methods according to the invention as set out below can be applied to any plant. The methods and compositions described herein can be used to screen and select monocot or dicot plants with increase tolerance to osmotic stress.

The methods described herein may encompass, but are not limited to, any of the plants selected from the group consisting of: *Arabidopsis*, tobacco, maize, soybean, sunflower, sorghum, canola, wheat, alfalfa, cotton, rice, barley, millet, sugar cane and switchgrass.

The present invention encompasses any plants selected by using the methods and compositions described in the current invention, and which exhibit an increase in tolerance to osmotic stress. An increase in tolerance to osmotic stress refers to the capability of the osmotically tolerant plant to grow under stress conditions which inhibit the growth of the control non-stress tolerant plants by at least 75%. Typically, the growth rate of stress tolerant plants of the invention will be inhibited by less than 50%, 40%, 30%, 20%, 10%, or 5%, or will have a growth rate which is not significantly inhibited by growth conditions which inhibit the growth of the parental, non-stress tolerant plants by at least 75%.

The current invention provides methods and compositions to screen, identify, select plants that are tolerant or resistant to a stress condition. This plant can be a transgenic plant or a naturally occurring plant variety.

In one embodiment, the method described in the current invention is used for screening for osmotically tolerant plants in a high-throughput fashion. In one embodiment, the method described in the current invention is used for screening more than 20 plants at one time. In one embodiment, the method described in the current invention is used for screening more than 50 plants at one time. In one embodiment, the method described in the current invention is used for screening more than 100 plants at one time.

Embodiments

One embodiment of this invention is a method of selecting seeds from at least one transgenic plant line with increased osmotic stress tolerance, wherein the method comprising the steps of: (a) obtaining seeds from at least one transgenic plant line comprising at least one heterologous polynucleotide sequence; (b) subjecting the seeds to osmotic stress by placing them on media comprising at least two osmolytes; and (c) selecting seeds that show an increased percentage seedling emergence when compared to seeds from a control plant, wherein the control plant does not comprise the at least one heterologous polynucleotide sequence, and wherein the seeds from the control plant are subjected to the same osmotic stress as the seeds from the at least one transgenic plant to be tested.

In one embodiment, the method described in the current invention is used for screening for osmotically tolerant plants in a high-throughput fashion. In one embodiment, the method described in the current invention is used for screening more than 100 plants at one time.

In one embodiment, the method described in the current invention is used for screening at least 20 plants at one time. In one embodiment, the method described in the current invention is used for screening at least 50 plants at one time. In one embodiment, the method described in the current invention is used for screening at least 100 plants at one time. In one embodiment, the method described in the current invention is used for screening at least 200 plants at one time. In one embodiment, the method described in the current invention is used for screening at least 300 plants at one time. In one embodiment, the method described in the current invention is used for screening at least 400 plants at one time. In one embodiment, the method described in the current invention is used for screening at least 500 plants at one time.

In one embodiment, the at least one heterologous polynucleotide sequence is operably linked to a promoter. In one embodiment, the promoter is a tissue-specific promoter. In one embodiment, the promoter is an inducible promoter.

One embodiment of the present invention is the method of identifying at least one plant with increased osmotic stress tolerance, the method comprising the steps of: (a) obtaining a population of plants of a single species; (b) subjecting the seeds of the plants to osmotic stress by placing them on media comprising at least two osmolytes; (c) selecting seeds that show an increased percentage seedling emergence when compared to an average of the percentage seedling emergence of the seeds of step (b); and (d) growing plants from the selected seeds of step (c).

In one embodiment, the emerged seedlings of step (c) of the methods described above are further screened for either percentage leaf emergence or percentage leaf greenness, or for both percentage leaf emergence and percentage leaf greenness.

In one embodiment, the media comprises two osmolytes. In one embodiment, the media comprises at least three osmolytes. In one embodiment, the media comprise three osmolytes. In one embodiment, the media comprises at least four osmolytes. In one embodiment, the media comprises four osmolytes.

In one embodiment, the osmotic pressure exerted by the at least two, the at least three, or the at least four solutes in the media is in the range of 0.4-1.23 MPa (megapascals).

In one embodiment, the osmolytes are selected from the group consisting of a water soluble inorganic osmolyte, a sugar alcohol osmolyte and a high molecular weight polymeric osmolyte.

In one embodiment, the water soluble inorganic osmolyte is sodium chloride, the sugar alcohol osmolyte is mannitol, sorbitol, or both mannitol and sorbitol, and the high molecular weight polymeric osmolyte is PEG (polyethylene glycol).

In one embodiment, the water soluble inorganic osmolyte is sodium chloride, the sugar alcohol osmolyte is mannitol, sorbitol or both mannitol and sorbitol, and the high molecular weight polymeric osmolyte is PEG (polyethylene glycol).

In one embodiment, the transgenic plant line used for the methods and compositions described in the current invention is a dicot. In one embodiment, the transgenic plant line used for the methods described in the current invention is a monocot.

In one embodiment, the plant species used for the methods and compositions described in the current invention is a dicot species. In one embodiment, the plant species used for the methods described in the current invention is a monocot species.

In one embodiment, the methods and compositions described in the current invention are used for selecting *Arabidopsis* plants with increased osmotic resistance. In one embodiment, the methods and compositions described in the current invention are used for selecting small seed plants such as tobacco, with increased osmotic resistance. In one embodiment, the methods and compositions described in the current invention are used for selecting crop plants with increased osmotic resistance. In one embodiment, the methods and compositions described in the current invention are used for selecting economically important crop plants with increased osmotic resistance.

In another embodiment, the invention includes plants with increased osmotic stress tolerance, identified and selected using the methods and compositions disclosed herein. The current invention also encompasses plant cells, tissues, plants, seeds, progeny plants and subsequent generations.

One embodiment of the current invention is a method of selecting seeds or plants from at least one transgenic plant line with increased tolerance to abiotic stress, the method comprising the steps of: (a) obtaining seeds or plants from at least one transgenic plant line comprising at least one heterologous polynucleotide sequence; (b) subjecting the seeds or plants to at least one stress selected from the group consisting of osmotic stress, paraquat stress, triple stress, low temperature stress, nitrogen stress, drought stress, AT-BSO and high light stress, and high light and low nitrogen stress; and (c) selecting seeds or plants that show an increased percentage seedling emergence or plant tolerance when compared to control seeds or control plants from a control plant line, wherein the control plant line does not comprise the at least one heterologous polynucleotide sequence, and wherein the control seeds or control plants from the control plant line are subjected to the same stress as the seeds or plants from the at least one transgenic plant line to be tested.

One embodiment of the current invention is a method of selecting a transgenic plant line with increased tolerance to abiotic stress, the method comprising the steps of: (a) obtaining at least one transgenic plant line comprising at least one heterologous polynucleotide sequence; (b) subjecting the plant line to abiotic stress; and (c) selecting a plant line that shows at least one phenotype selected from the group consisting of: increased tolerance to triple stress, altered root hydrotropism characteristics, increased percentage germination under cold conditions, increased paraquat tolerance, altered ABA response, increased tolerance to osmotic stress, increased biomass under cold conditions at grain-filling stage, increased nitrogen stress tolerance, increased tolerance to AT-BSO and high light stress, and increased tolerance to high light and low nitrogen stress, when compared to a control plant, wherein the control plant does not comprise the at least one heterologous polynucleotide sequence, and wherein the control plant is subjected to the same stress as the transgenic plant to be tested.

One embodiment of the current invention is a method for identifying at least one plant with increased tolerance to abiotic stress, the method comprising the steps of: (a) obtaining a population of plants of a single species; (b) subjecting the plants to abiotic stress; (c) selecting a plant that shows at least one phenotype selected from the group consisting of increased tolerance to triple stress, altered root hydrotropism characteristics, increased percentage germination under cold conditions, increased paraquat tolerance, altered ABA response, increased tolerance to osmotic stress, increased tolerance to AT-BSO and high light stress, and increased tolerance to high light and low nitrogen stress, when compared to an average of the phenotype exhibited by the plants of step (b).

One embodiment is the plants obtained by the method of any of the above embodiments, wherein the plants exhibit increased resistance to abiotic stress. The abiotic stress can be selected from a group consisting of osmotic stress, paraquat stress, triple stress, low temperature stress, drought stress, increased tolerance to AT-BSO and high light stress, and increased tolerance to high light and low nitrogen stress. In one embodiment, the plants show at least one phenotype selected from the group consisting of increased tolerance to triple stress, altered root hydrotropism characteristics, increased percentage germination under cold conditions, increased paraquat tolerance, altered ABA response, increased tolerance to osmotic stress, increased tolerance to AT-BSO and high light stress, and increased tolerance to high light and low nitrogen stress.

One embodiment of the current invention is a method of selecting a transgenic plant with an altered response to nitrogen stress, the method comprising the steps of: (a) obtaining an activation-tagged population of plants of a single species; (b) selecting a plant from step (a) that shows at least one phenotype selected from the group consisting of: suppression of an nlp7 knock-out mutant phenotype, suppression of negative regulation of an NRT2.1 promoter by high nitrogen, suppression of an nia1nia2 mutant phenotype, and suppression of an antimyb early senescence phenotype, when compared to a control plant, wherein the control plant does not comprise the activation tag. The activation tag may comprise four multimerized enhancer elements derived from the Cauliflower Mosaic Virus 35S promoter. The species of step (a) may be *Arabidopsis*. The phenotype of step (b) may be selected from the group consisting of: suppression of an *Arabidopsis* nlp7 knock-out mutant phenotype, suppression of negative regulation of an *Arabidopsis* NRT2.1 promoter by high nitrogen, suppression of an *Arabidopsis* nia1nia2 mutant phenotype, and suppression of an *Arabidopsis* antimyb early senescence phenotype. The method may further comprise isolation of the polynucleotide sequence that is activation-tagged. The method may further comprise transformation of a plant with the isolated polynucleotide sequence into the appropriate background to confirm the phenotype.

One embodiment of the current invention is a method of identifying a polynucleotide sequence involved in nitrogen stress, the method comprising the steps of: (a) obtaining at least one transgenic plant comprising a promoter functional in a plant cell operably linked to an isolated polynucleotide sequence; (b) selecting a plant from step (a) that shows at least one phenotype selected from the group consisting of: suppression of an nlp7 knock-out mutant phenotype, suppression of negative regulation of an NRT2.1 promoter by high nitrogen, suppression of an nia1nia2 mutant phenotype, and suppression of an antimyb early senescence phenotype, when compared to a control plant, wherein the control plant does not comprise the at least one heterologous polynucleotide sequence. The species of step (a) may be *Arabidopsis*. The phenotype of step (b) may be selected from the group consisting of: suppression of an *Arabidopsis* nlp7 knock-out mutant phenotype, suppression of negative regulation of an *Arabidopsis* NRT2.1 promoter by high nitrogen, suppression of an *Arabidopsis* nia1nia2 mutant phenotype, and suppression of an *Arabidopsis* antimyb early senescence phenotype. The promoter of step (a) may be a constitutive, tissue-specific, or inducible promoter or a combination of any of these. The promoter may be a Cauliflower Mosaic Virus 35S promoter.

In one embodiment, the invention encompasses the plants obtained by the method of any of the above embodiments wherein the plants show increased growth rate under non-stressed conditions. The increased growth rate may be an increase in root growth rate. The increased root growth rate may be measured in the presence or absence of ABA.

In one embodiment, any of the assays described herein can be done in a high throughput manner. For example, any of the assays described herein can be used for screening at least 20, 50, 100, 200, 300, 400, 500 or 1000 plants at one time.

In one embodiment, one or more than one of the assays described herein can be done to identify stress tolerant plants, and stress tolerant genes. The assays can be done simultaneously, or sequentially.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

EXAMPLES

The present invention is further illustrated in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Osmotic Stress Assay

To establish a systematic screen to identify novel osmotic stress-tolerant mutants, a screen was standardized for osmotic stress tolerance using a combination of osmoticum. A combination of osmolytes in the media, such as water soluble inorganic salts, sugar alcohols and high molecular weight non-penetrating osmolytes was used to select for osmotically-tolerant plant lines. Screening of transgenic plant lines was done on media with combination of osmolytes to allow the identification of genes involved in general osmotic stress tolerance. Osmolytes include, but are not limited to, the following: sodium chloride (NaCl), sorbitol, mannitol and polyethylene glycol (PEG).

To develop a screen for osmotic stress assay, seeds from 48 *Arabidopsis* transgenic lines were procured to test for their response to osmotic stress.

The osmotic stress agents used in this assay were the following: NaCl (sodium chloride); sorbitol; mannitol; and polyethylene lycol (PEG). By providing these agents in the media, we aimed to mimic the multiple stress conditions in the in vitro environment thereby giving the plant the opportunity to respond to four stress agents.

Methods and Materials:

The standardization of growth conditions and generation of kill curves for various osmotic stress agents individually was done before the development of quad stress assay conditions. Data generated from the kill curve experiments showed that the lethal concentrations for NaCl was 150 mM, sorbitol and mannitol was 500 mM, and PEG could only be used at 10% concentration (higher concentrations precipitated in the media). As there were four stress agents being used together, a quarter of each together in a solution would denote 100% stress or an osmotic pressure of 1.23 MPa. Therefore the following concentrations of each component were used in "100% quad media".

| Stress agents | Concentrations |
| --- | --- |
| NaCl | 62.5 mM |
| Sorbitol | 125 mM |
| Mannitol | 125 mM |
| PEG | 10% |

Assay Conditions: Seeds were surface sterilized and stratified for 48 hrs. About 100 seeds were inoculated in one plate and cultured in a growth chamber programmed for 16 h of light at 22° C. temperature and 50% relative humidity. Germination was scored as the emergence of radicle.

Assay Plan: A 6-day assay and an extended 10-day assay were done to test the seeds from the 48 transgenic *Arabidopsis* lines for osmotic stress tolerance.

Day 0—Surface sterilized seeds of different drought leads and stratify.
Day 2—Inoculated onto quad media.
Day 4—Counted for germination (48 hrs).
Day 5—Counted for germination (72 hrs)/Take pictures or Scan plates from 48 hrs to 96 hrs.
Day 6—Counted for germination (96 hrs).
For the extended 10-day assay, germination was scored from 48 hrs to 96 hrs. On day 7, 8, 9 and 10, the emerged seedlings were checked for greenness and four leaf stage.

Preparation of Media

Germination medium (GM or 0% quad media) for 1 liter:

| | |
| --- | --- |
| MS salt | 4.3 g |
| Sucrose | 10 g |
| 1000x Vitamin mix | 1 ml |

-continued

| MES (pH 5.7 with KOH) | 10 ml |
|---|---|
| Phytagel (0.3%) | 3 g |

To this the quad agents (the four osmolytes) were added by individually weighing the specific amounts in grams for their respective concentrations. Quad media preparation chart for all concentrations of osmolytes is given in Table 1.

TABLE 1

| | 10% | 20% | 30% | 40% | 50% | 60% | 70% | 80% | 90% | 100% |
|---|---|---|---|---|---|---|---|---|---|---|
| NaCl | 0.36 | 0.731 | 1.09 | 1.46 | 1.82 | 2.19 | 2.55 | 2.9 | 3.29 | 3.656 |
| Mannitol | 2.27 | 4.55 | 6.83 | 9.1 | 11.38 | 13.66 | 15.93 | 18.2 | 20.49 | 22.77 |
| Sorbitol | 2.27 | 4.55 | 6.83 | 9.1 | 11.38 | 13.66 | 15.93 | 18.2 | 20.49 | 22.77 |
| PEG | 10 | 20 | 30 | 40 | 50 | 60 | 70 | 80 | 90 | 100 |

Sterilization of Seeds

Approximately 100 μl of *Arabidopsis* Columbia wild type seeds (col wt) and the T2 seeds of the 48 lines to be tested were taken in 1.75 ml microfuge tubes and sterilized in ethanol for 1 min 30 sec followed by one wash with sterile water. Then they were subjected to bleach treatment (4% bleach with Tween 20) for 2 min 30 sec. This was followed by 4 to 5 washes in sterile water. Seeds were stratified at 4° C. for 48 hrs before inoculation.

Inoculation of Seeds

Stratified seeds were plated onto a single plate of each quad stress concentration as given in Table 1. Plates were cultured in the chambers set at 16 h of light at 22° C. temperature and 50% relative humidity. Germination was scored as the emergence of radicle over a period of 48 to 96 hrs. Seeds were counted manually using a magnifying lens. Plates were scanned at 800 dpi using Epson scanner 10,000 XL and photographed. In case of the extended assay, leaf greenness (manual) and true leaf emergence, i.e., 4-Leaf stage (manual scoring) were also scored over a period of 10 days to account for the growth rate and health of the germinated seedlings.

The data was analyzed as percentage germination to the total number of seeds that were inoculated. Analyzed data was represented in the form of bar graphs and sigmoid curves by plotting quad concentrations against percent germination.

Figure 2:
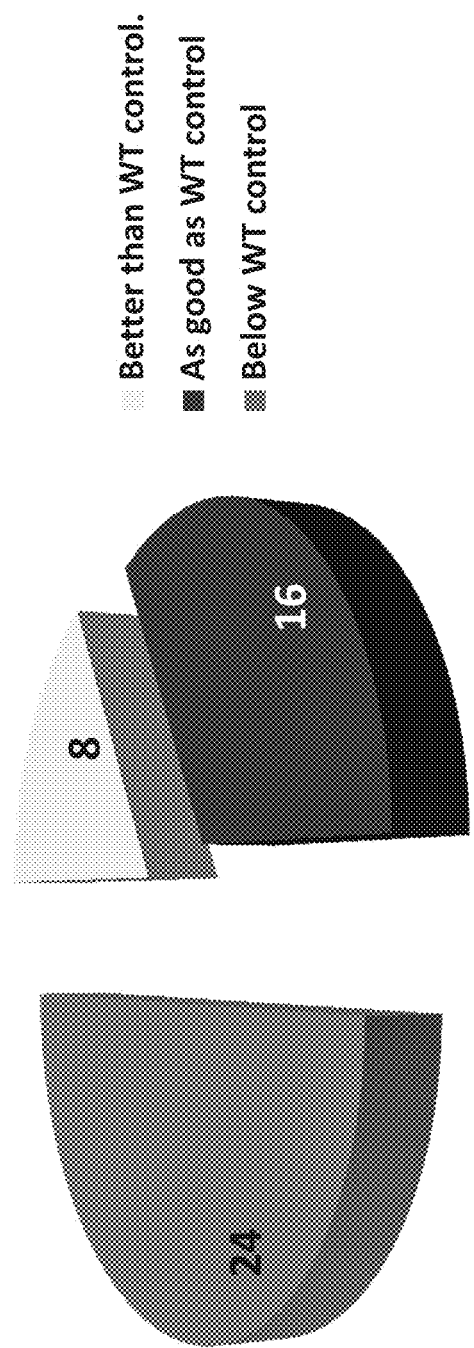
FIG. 2 is a graph showing the distribution of 48 lines in the following categories: "better than", "as good as", and "worse than" controls in the osmotic stress quad assay.

Observations and Results:

The germination curve (FIG. 1) for the wild type seeds had a sigmoid pattern with high rate of germination at lower concentrations, followed by a slow decline and a sharp drop at 60% quad concentration. Concentrations beyond 60% were lethal for germination of wild type seeds. Therefore for a line to qualify as a better performer than control it had to show a better germination at 60% quad and above. All the 48 lines were screened at 6 different concentrations: 0%, 20%, 40%, 60%, 80% and 100% quad along with wild type controls. The results were based on that control in each batch tested. Data for germination count of all 48 lines and their graphs at 48 hr, 72 hr and 96 hr were documented, and Tables 2-4 show the data for the 48 lines. FIG. 2 shows the distribution of 48 lines in the categories; better than, as good as, and worse than the wild-type controls. Tables 2-4 list of all 48 lines and their status compared to controls.

TABLE 2

| Sl. No. | Observation |
|---|---|
| 18 | Better than WT control. |
| 25 | Better than WT control. |
| 28 | Better than WT control. |
| 56 | Better than WT control. |
| 58 | Better than WT control. |

TABLE 2-continued

| Sl. No. | Observation |
|---|---|
| 61 | Better than WT control. |
| 64 | Better than WT control. |
| 74 | Better than WT control. |

TABLE 3

| Sl. No. | Observation |
|---|---|
| 10 | Below WT control |
| 17 | Below WT control |
| 20 | Below WT control |
| 33 | Below WT control |
| 38 | Much Below WT control. |
| 39 | Below WT control |
| 40 | Below WT control |
| 42 | Below WT control |
| 43 | Below WT control |
| 44 | Below WT control |
| 47 | Much Below WT control. |
| 76 | Below WT control |
| 68 | Below WT control |
| 66 | Below WT control (High variation) |
| 84 | As good as WT control |
| 80 | As good as WT control |

TABLE 4

| Sl. No. | Observation |
|---|---|
| 1 | As good as WT control |
| 11 | As good as WT control |
| 12 | As good as WT control |
| 14 | As good as WT control |
| 16 | As good as WT control (slightly better) |
| 26 | As good as WT control (slightly better) |
| 27 | As good as WT control |
| 30 | As good as WT control |
| 34 | As good as WT control |
| 37 | As good as WT control |
| 50 | As good as WT control |
| 54 | As good as WT control |
| 55 | As good as WT control (slightly better) |
| 60 | As good as WT control |
| 67 | As good as WT control |
| 71 | As good as WT control |
| 59 | As good as WT control |
| 65 | As good as WT control |
| 81 | As good as WT control |
| 82 | As good as WT control |
| 79 | As good as WT (WT had issues) |

TABLE 4-continued

| SI. No. | Observation |
|---|---|
| 90 | As good as WT (WT had issues) |
| 98 | As good as WT (WT had issues) |
| 70 | Below WT control |

Figure 3A:
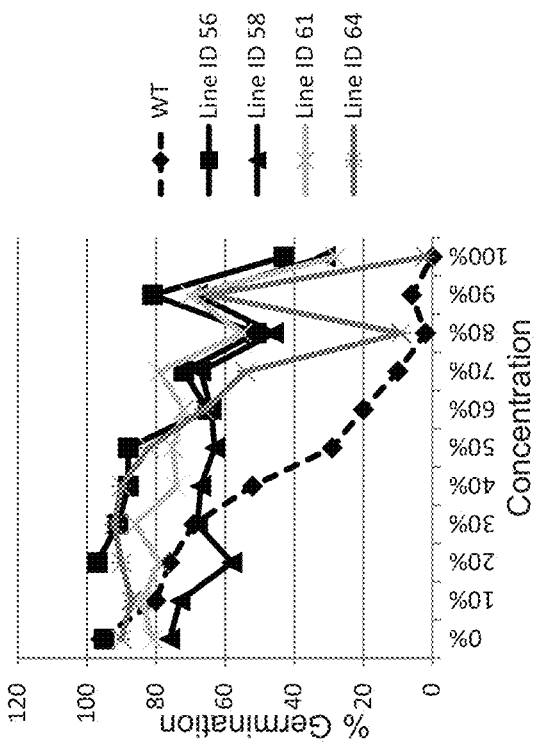
FIG. 3A and FIG. 3B present graphs showing germination curves at 48 hours for the selected eight lines, done in two batches, in the osmotic stress assay.
Figure 3B:
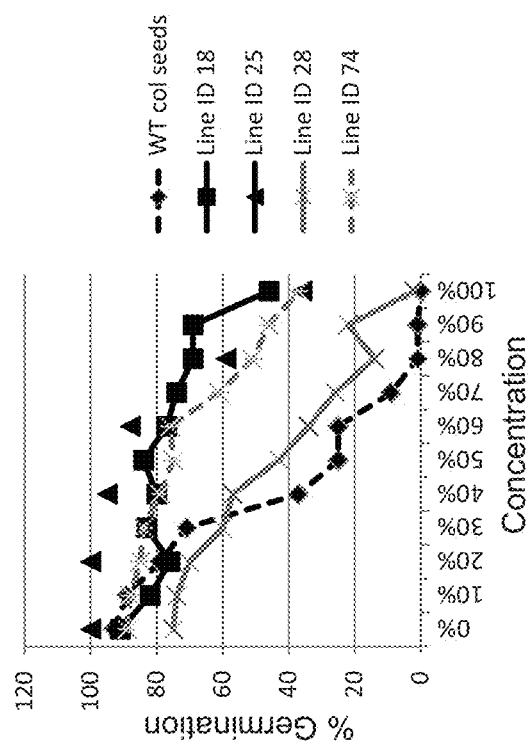

The best 8 lines were selected and germination experiment repeated at all 10 concentrations (10%, 20%, 30%, 40%, 50%, 60%, 70%, 80%, 90% and 100% quad) for germination. Table 5 shows the list of 8 lines with internal ID numbers selected for the germination assay with all 10 quad concentrations and the extended assay, on the basis of the initial screen. Table 6, Table 7 and FIG. 3A-FIG. 3B show the data generated for 48 hrs germination for all 8 lines done in both batches along with the respective WT controls.

TABLE 5

| SI. No. | Line ID |
|---|---|
| 1 | Line ID 18 |
| 2 | Line ID 25 |
| 3 | Line ID 28 |
| 4 | Line ID 74 |
| 5 | Line ID 56 |
| 6 | Line ID 58 |
| 7 | Line ID 61 |
| 8 | Line ID 64 |

TABLE 6

Percentage Germination Data for Line ID Nos. 18, 25, 28 and 74 in the 10-Day Assay

| Quad Concentration | WT | 18 | 25 | 28 | 74 |
|---|---|---|---|---|---|
| 0% | 93 | 91 | 100 | 75 | 89 |
| 10% | 89 | 82 | | 74 | 88 |
| 20% | 79 | 76 | 100 | 70 | 85 |
| 30% | 71 | 83 | | 60 | 84 |
| 40% | 37 | 80 | 95 | 57 | 79 |
| 50% | 25 | 84 | | 43 | 75 |
| 60% | 25 | 77 | 88 | 34 | 76 |
| 70% | 9 | 74 | | 26 | 61 |
| 80% | 1 | 69 | 59 | 14 | 51 |
| 90% | 1 | 69 | | 22 | 46 |
| 100% | 0 | 46 | 36 | 2 | 37 |

TABLE 7

Percentage Germination Data for Line ID Nos. 56, 58, 61 and 64 in the10-Day Assay

| Quad Concentration | WT | 56 | 58 | 61 | 64 |
|---|---|---|---|---|---|
| 0% | 96 | 95 | 76 | 81 | 90 |
| 10% | 80 | | 73 | 84 | 87 |
| 20% | 76 | 97 | 58 | 79 | 90 |
| 30% | 69 | 91 | 68 | 86 | 92 |
| 40% | 52 | 88 | 67 | 74 | 90 |
| 50% | 29 | 88 | 63 | 75 | 82 |
| 60% | 20 | 65 | 64 | 72 | 66 |
| 70% | 10 | 72 | 67 | 79 | 54 |
| 80% | 2 | 51 | 46 | 55 | 9 |
| 90% | 6 | 81 | 68 | 70 | 65 |
| 100% | 0 | 43 | 31 | 28 | 2 |

Figure 4A:
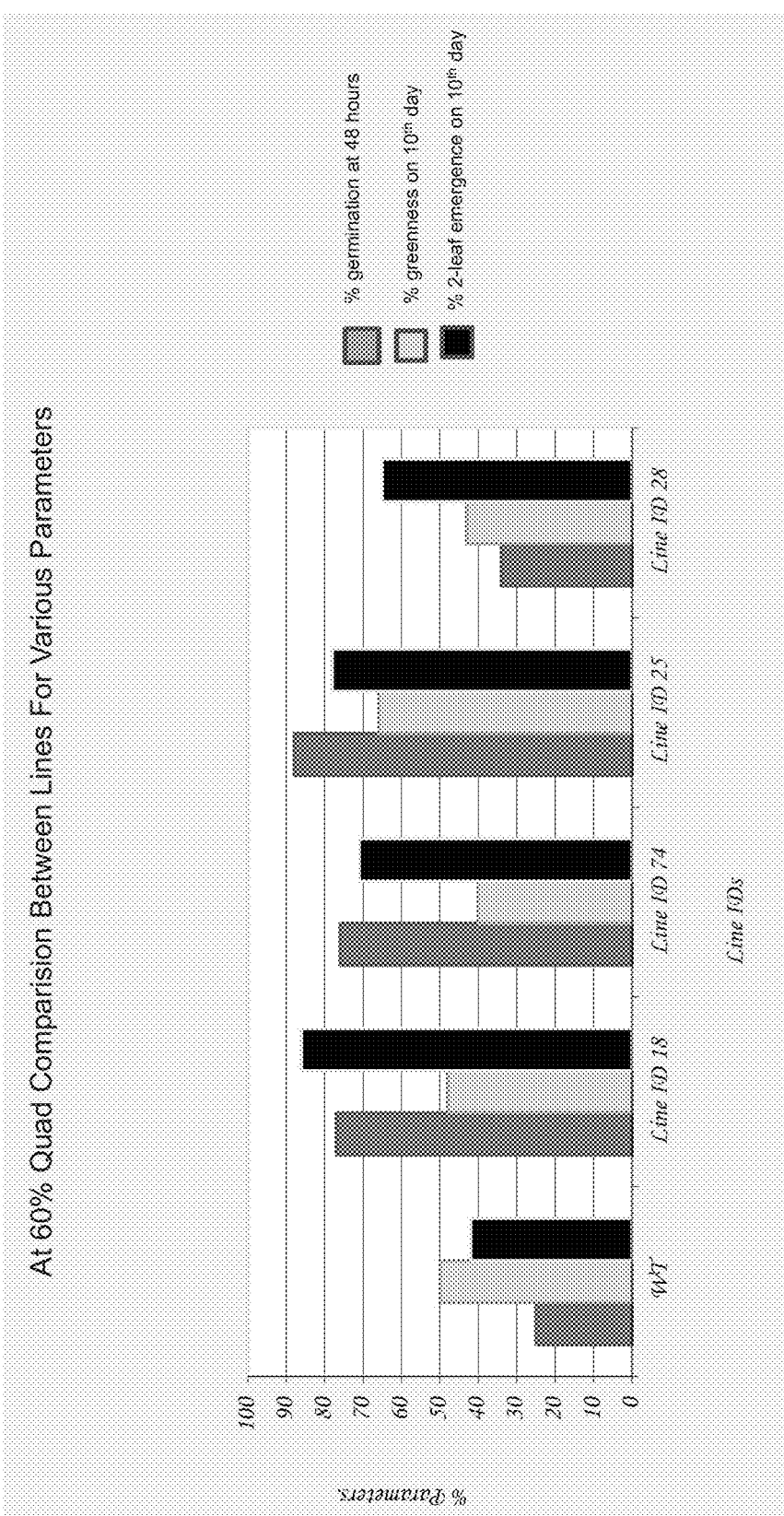
FIG. 4A is a graph showing the comparison of various scored parameters of the selected line ID Nos. 18, 74, 25 and 28 at 60% quad concentration in the osmotic stress assay.
Figure 4B:
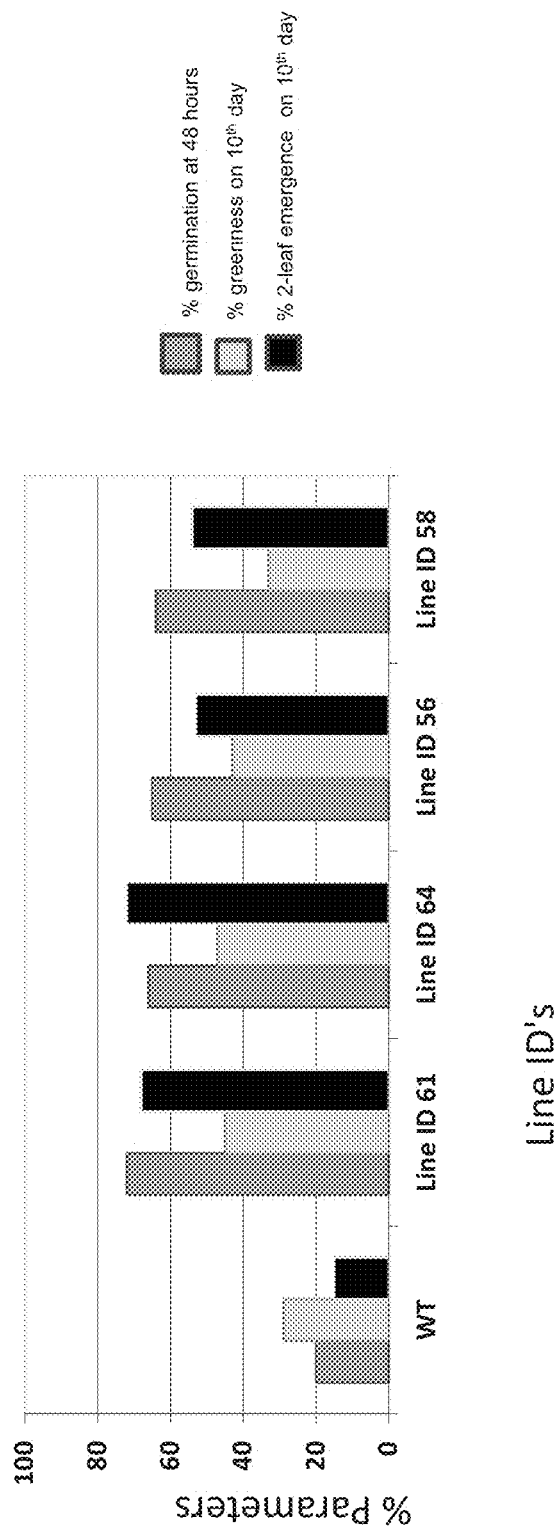
FIG. 4B is a graph showing the comparison of various scored parameters of the selected line ID Nos. 61, 64, 56 and 58 at 60% quad concentration in the osmotic stress assay.
Figure 5A:
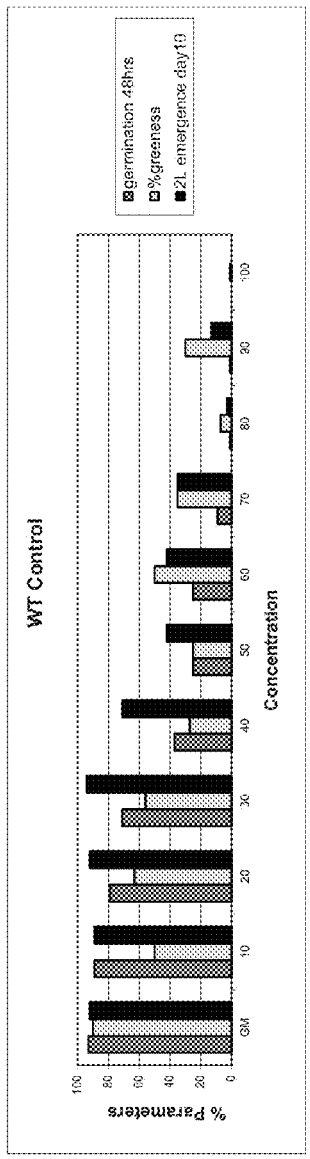
FIG. 5A-FIG. 5E present a series of graphs showing the comparison of the wild-type control with Line ID Nos. 18, 25, 28 and 74 on day 10 for all three parameters: percentage germination, percentage greenness and percentage leaf emergence.
Figure 5B:
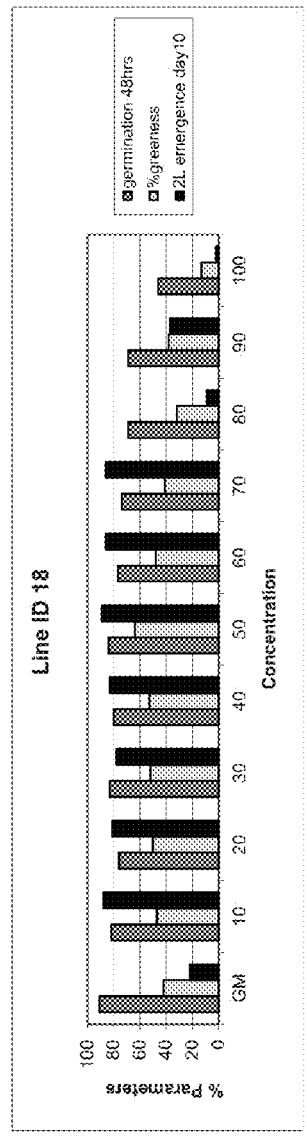
Figure 5C:
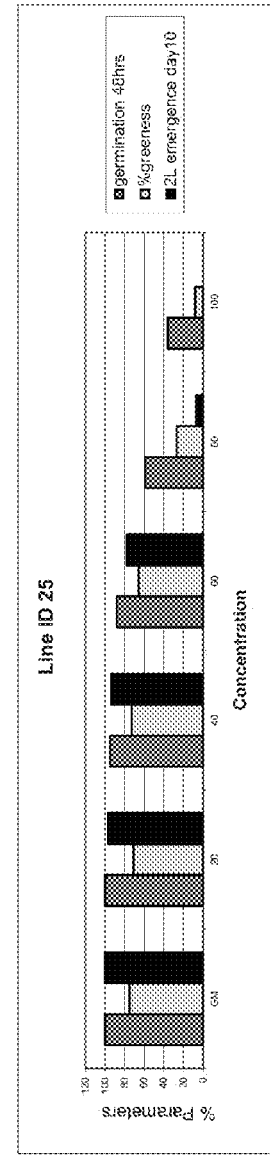
Figure 5D:
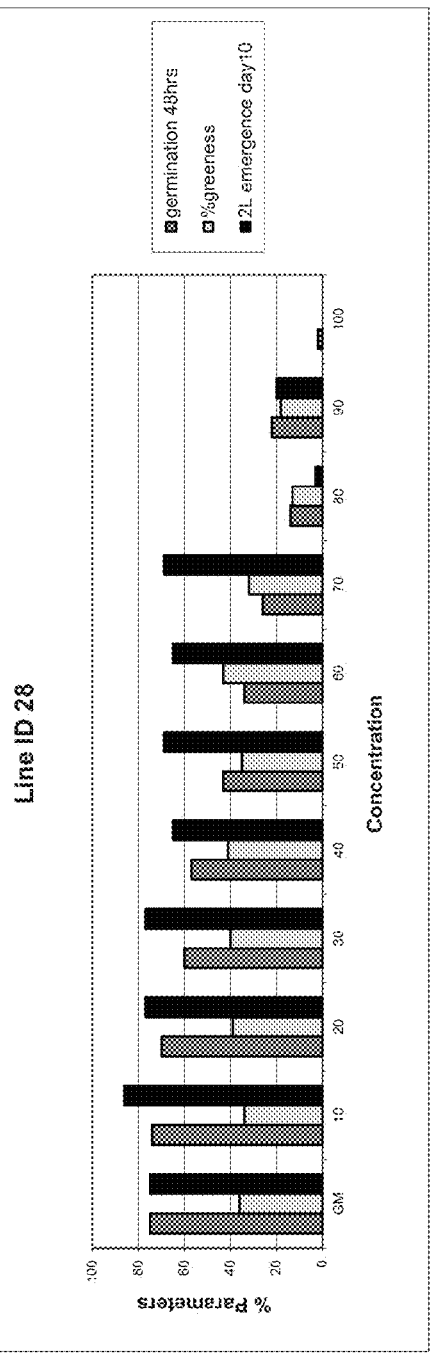
Figure 5E:
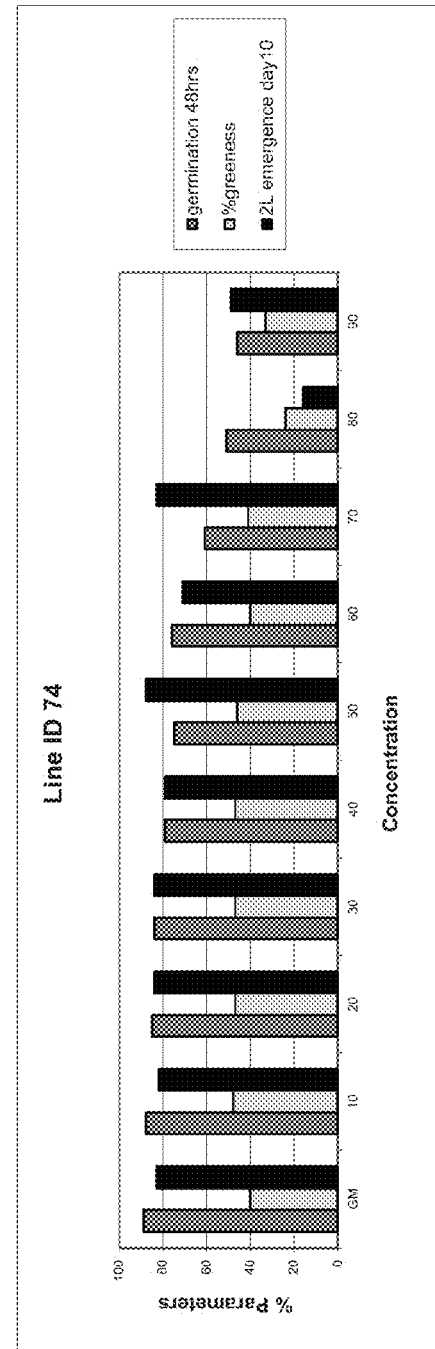
Figures 6A, 6B:
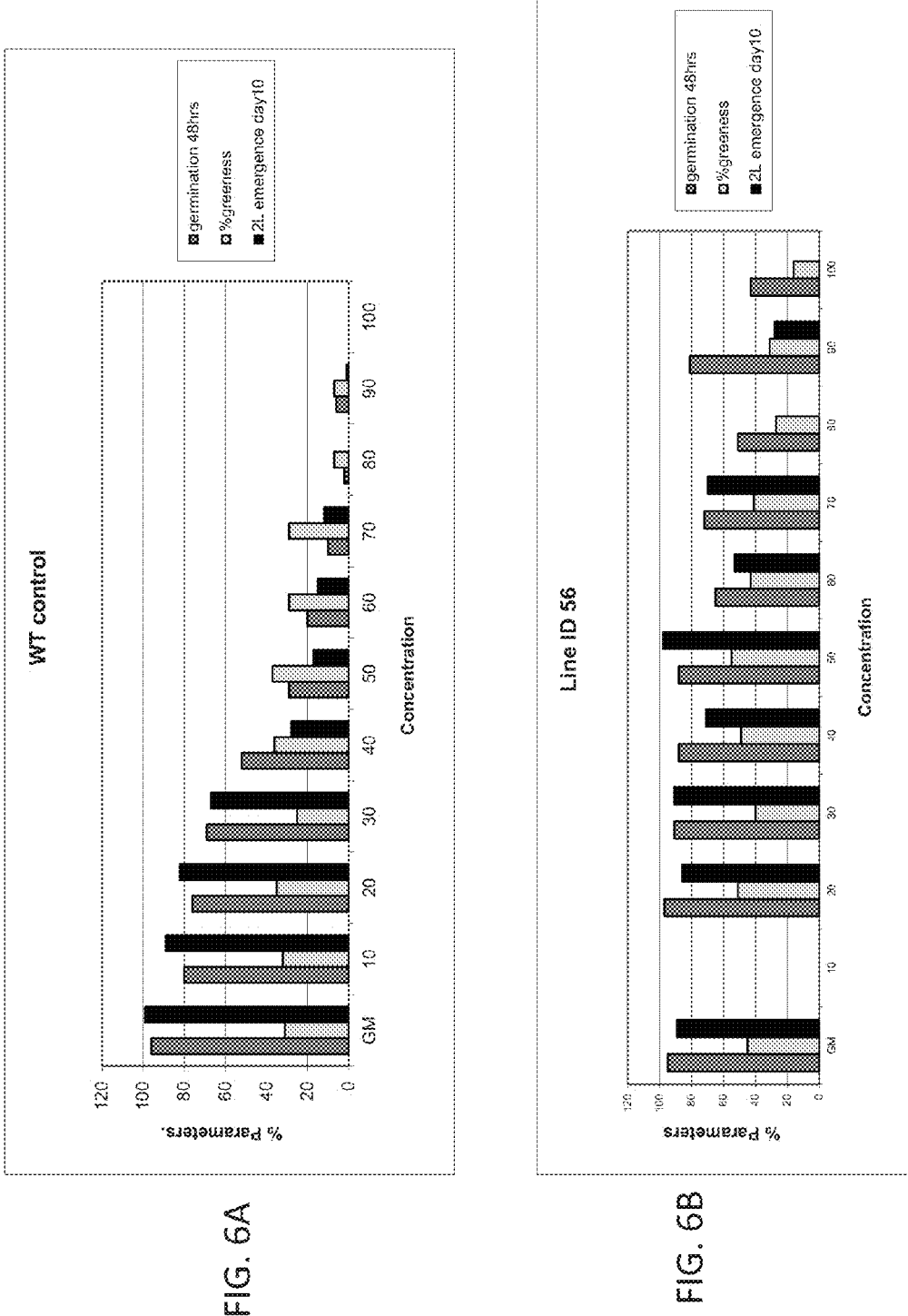
FIG. 6A-FIG. 6E present a series of graphs showing the comparison of the wild-type control with Lines ID nos. 56, 58, 61 and 64 on day 10 for all three parameters: percentage germination, percentage greenness and percentage leaf emergence.
Figures 6C, 6D:
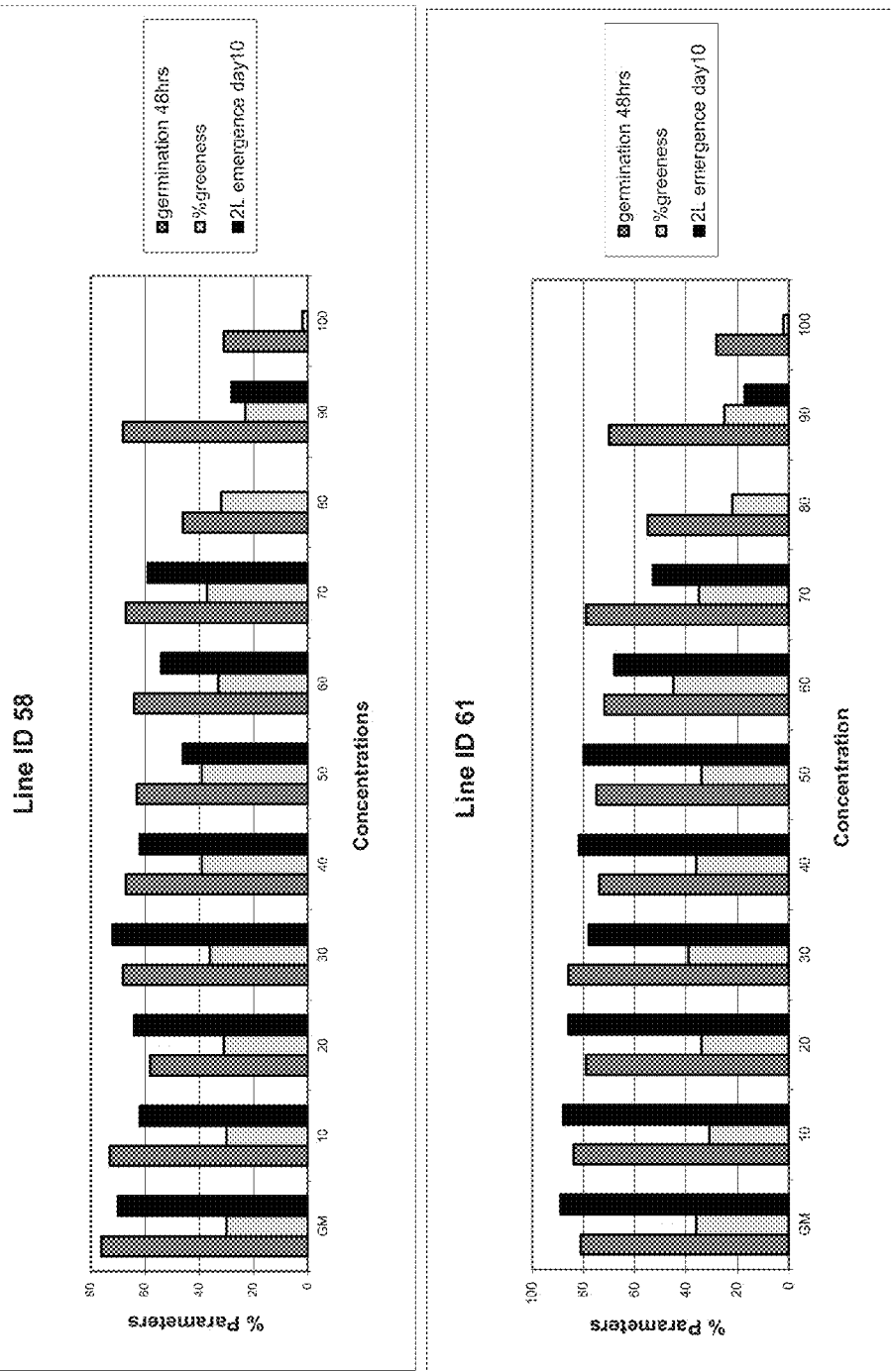
Figure 6E:
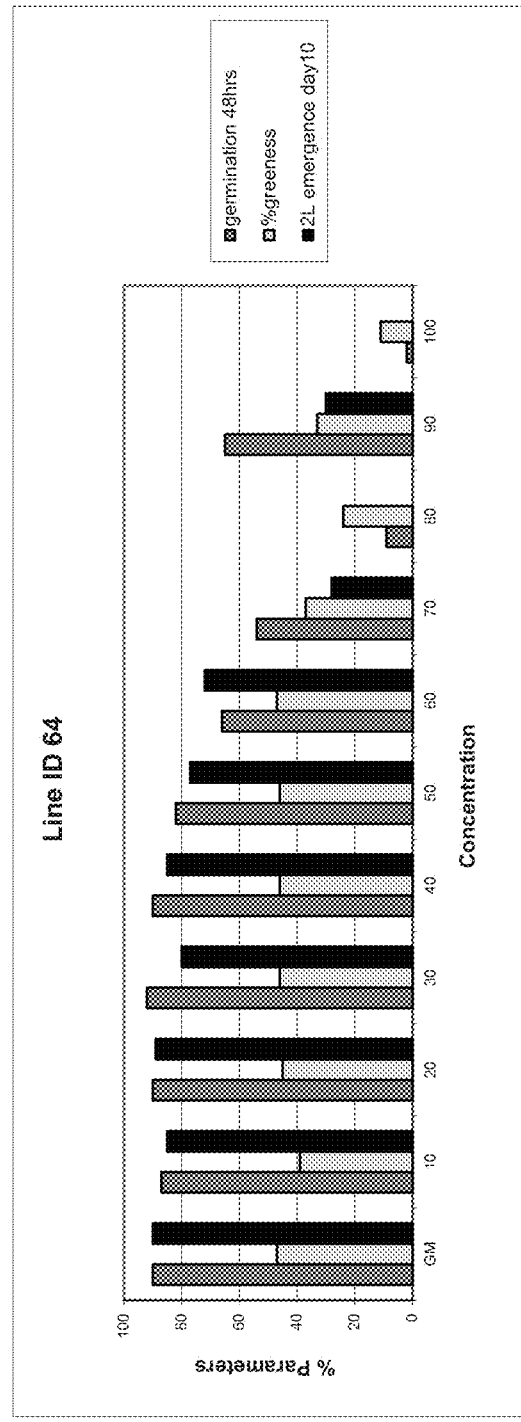

These 8 lines (Line ID Nos. 18, 25, 28, 74, 56, 58, 61 and 64) were scored for percentage greenness and percentage leaf emergence in an extended 10 day assay as well. They were initially scored at only 60% quad, for germination at 48 hours, and for percentage greenness and percentage leaf emergence in an extended 10 day assay. The results are shown in FIG. 4A and FIG. 4B for the 8 selected lines at 60% quad, tested for all 3 parameters.

Percentage Greenness and Percentage Leaf Emergence:

Percentage greenness was scored as the percentage of seedlings with green leaves (cotyledonary or true leaves) compared to yellow, brown or purple leaves. Greenness was scored manually and if there was any yellow or brown streaks on any of the 4 leaves, it was not considered green. Greenness was counted for seedlings with total green leaves only.

The leaf emergence was scored as the appearance of fully expanded leaves 1 and 2, after the two cotyledonary leaves had fully expanded. So percentage leaf emergence is the number of seedlings with 2 true leaves or 4 leaves in total (2 cotyledonary and 2 true leaves).

FIG. 5A-FIG. 5E show the comparison between the selected lines of batch 1 and wild type for all 3 parameters on day 10. FIG. 6A-FIG. 6E show the comparison between selected lines of batch 2 and wild type for all 3 parameters on day 10.

Line ID 25, Line ID 61 and Line ID 64 were selected as the best 3 lines based on the criteria that they scored well above the wild-type (WT) control from 60% quad onwards considering germination and growth.

Figure 7:
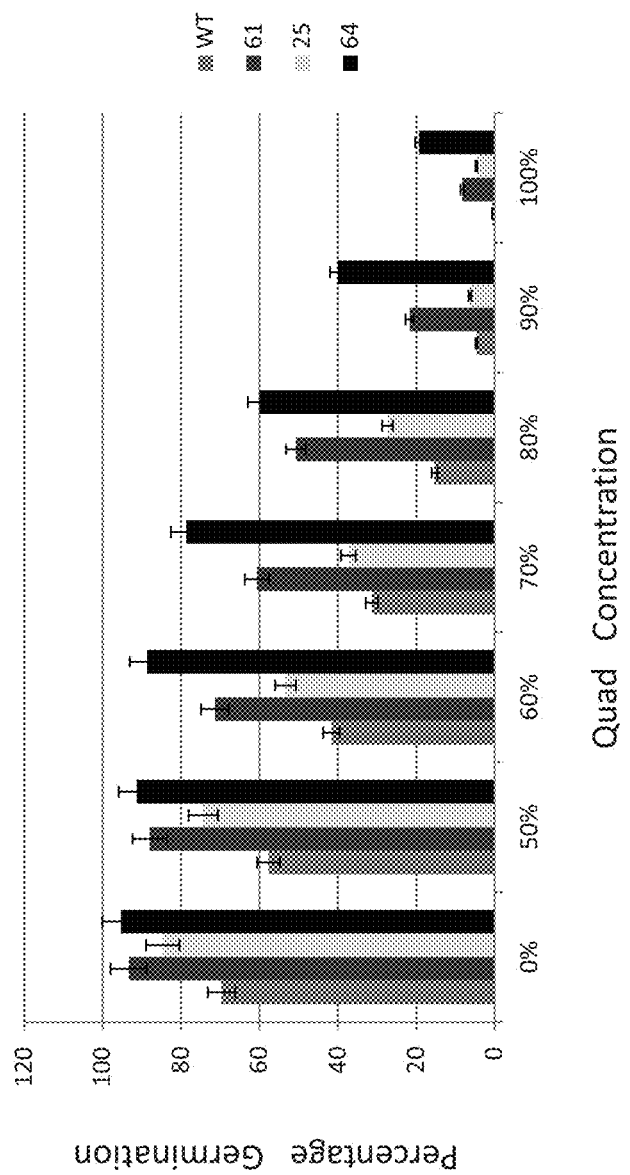
FIG. 7 shows a graph with the percentage germination data for three lines, Line ID 25, 61 and 64, along with standard deviations.
Figure 8:
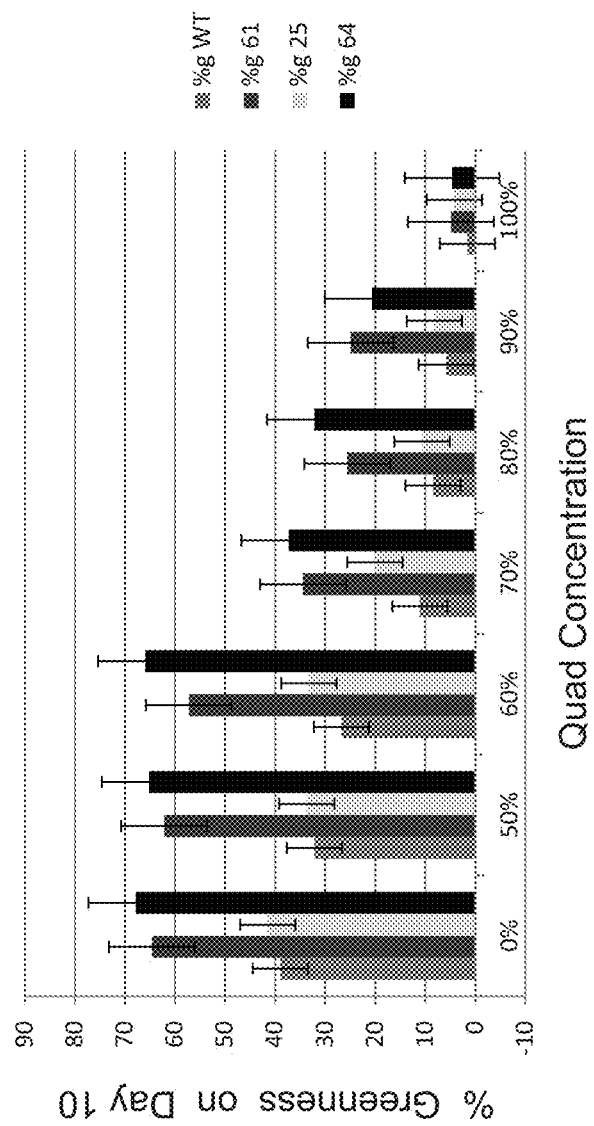
FIG. 8 shows a graph with the percentage greenness taken on day 10 for Line ID Nos. 61, 25 and 64 along with standard deviations.
Figure 9:
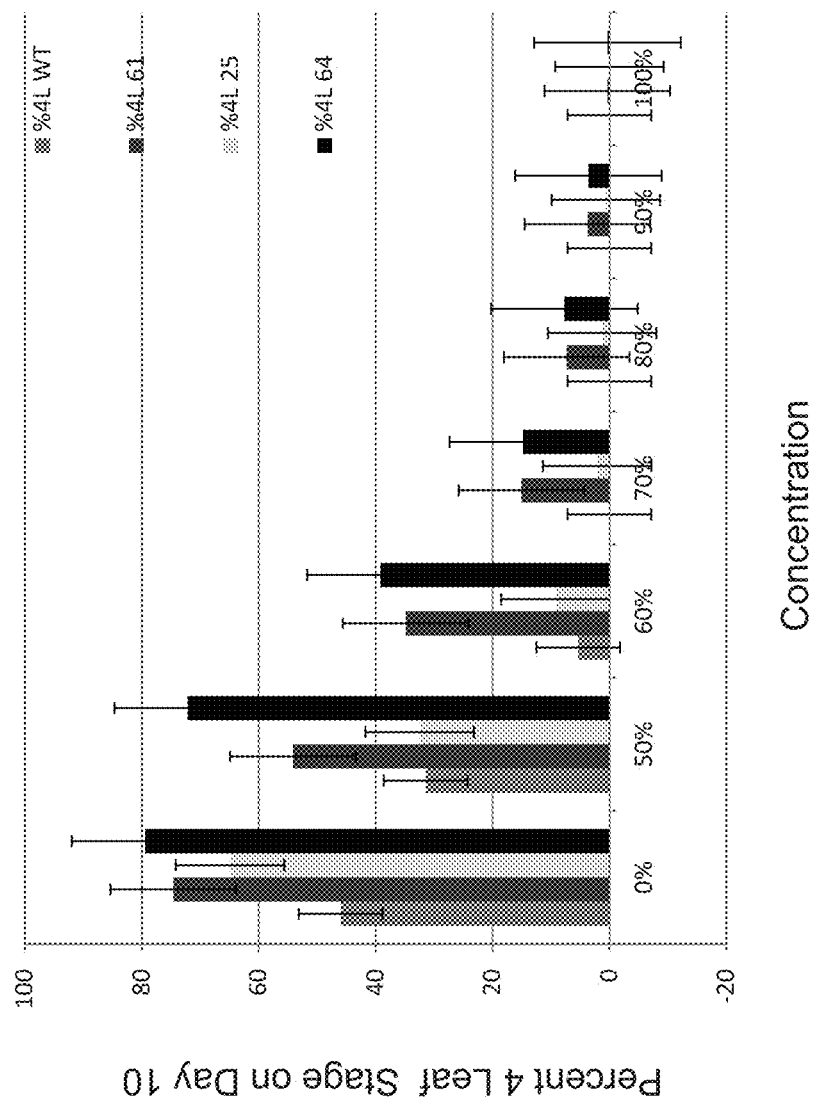
FIG. 9 shows a graph with the percentage for 4-leaf stage counts taken on day 10 for Line ID Nos. 61, 25 and 64 along with standard deviations.

Percentage germination at 48 hours, percentage leaf emergence and percentage greenness assays in 10-day assays were repeated for these 3 lines in triplicates. This final assay was performed at 0%, 50% to 100% concentrations of quad (FIG. 7, FIG. 8 and FIG. 9).

Example 2A

Triple Stress Assay

A systematic screen to identify mutants tolerant to a novel combination of three abiotic stresses is presented. Specifically, plants are grown in conditions of simultaneous drought stress, heat stress and high light stress. Mutants with positive growth and/or positive decay parameters can then be identified.

Materials:
*Arabidopsis* mutant and/or control lines.
Methods:
Phase 1 Screen: Seeds are soaked in water and incubated at 4° C. for 3 days in the dark. Cold shocked seeds are planted in controlled density and spacing on soil. Specifically, 9 plants in a 3×3 grid are grown per 5.5 inch square pot with 8 pots per flat. For phase 1 screens, each pot represents a different test line.

For 14 days, plants are grown under non-stressed conditions involving: (a) Soil: Metromix 360; (b) Fertilizer: Osmocote and Peter's; (c) Light Regime: 16 hours light/8 hours dark; (d) Light Intensity: 150 µE; (e) Temperature Regime: 22° C. day/20° C. night; and (f) Humidity: 50% Relative Humidity. On the last day of non-stressed growth, flats are brought to 100% soil water capacity and imaged and analyzed to get total green area pixel count, e.g., using a LemnaTec Scanalyzer.

The flats are then transferred to "triple stress" conditions consisting of: (a) no additional watering, (b) Light Regime: 16 hours light/8 hours dark; (c) Light Intensity: 350 µE (d) Temperature Regime: 22° C. day with a 32° C. pulse for 4 hours in the middle of the day/20° C. night; and (f) Humidity: 50% Relative Humidity. In these conditions, flats are imaged daily for 14 days.

From the LemnaTec data, comparisons are made between each single mutant line compared to the average of the other seven within the same flat. P-values are determined for growth area, growth slope and maximum day area, decay area and decay slope. Lines with a positive deviation and P-value of <0.05 for one or more of the parameters are considered an outlier.

Phase 2 Screen: Lines identified as outliers in phase 1 are then screened a second time. The soil, fertilizer, watering, L/D, and temperature regimes are identical to phase 1. However, one flat consists of 4 pots of a single mutant line and 4 pots of a wild-type control. Thus 36 mutant plants are directly compared to 36 wild type plants. P-values are determined for growth area, growth slope and maximum day area, decay area and decay slope. Lines with a P-value of <0.05 for one or more of the parameters are considered a true positive mutant and are advanced.

Phase 3 Screen: From positive phase 2 mutants, candidate genes likely to be responsible for the phenotype are identified. Individual genes are then tested within a transgenic construct to validate ability to recapitulate the positive triple stress phenotype. Transgenic and non-transgenic T2 seeds of *Arabidopsis* plants transformed with a construct of the candidate gene cDNA sequence driven by the CaMV 35S promoter (or other regulatory element) are separated and then screened as in phase 2.

Example 2B

Triple Stress Assay Data

Lines were assayed for the triple stress assay essentially as described in Example 2A. FIG. 10 shows an example of a phase 1 flat where line "D" is a positive growth outlier.

Comparison ("Comp") values of "+" indicate that a mutant ("MT") line had a positive growth value as compared to an average of the other seven lines in the same flat. The p-value is also with respect to the difference between each mutant line and the other seven. In FIG. 10, the mutant line "D" was positive for growth area and max day area with p-values of less than $10^{-3}$ for each parameter and is thus considered a significantly positive outlier.

Phase 1 outliers were assayed using the phase 2 planting arrangement described in Example 2A. FIG. 11A shows an example of an outlier that was positive for the decay area and decay slope parameters with p-values of 0.04 and 0.02 respectively. Comparison ("Comp") values of "+" indicate that a mutant line had a positive deviation value as compared to wild-type. The p-value is with respect to the difference between the mutant line and wild-type (FIG. 11A-FIG. 11B).

Candidate genes from a true phase 2 outlier were identified and tested as single transgenic constructs for their ability recapitulate the original phenotype. FIG. 11B shows an example of two candidate genes from a single phase 1/phase 2 growth mutant line. In this case, one gene ("D1511") had no significant effects in the triple stress assay whereas the other gene ("D1830") validated for growth area and growth slope with p-values of 0.001 and 0.003 respectively (FIG. 11B).

Example 2C

Statistical Methods for Use in the Triple Stress Assay

The captured leaf areas of each flat are first averaged among replicated plants to determine the mean and standard deviations for the activation-tagged and wild-type plants. In adjusting for biological and systematic error, these estimates obtained from the observed data are used in normalization. Error is estimated by fitting noise functions across replicates and days. Data is normalized using the error calculated weighted based on the green pixels counts from the first day from the days available. There are 15 days of measurements for each plant. These days are divided into growth interval and decay interval. The division of the intervals is based on the day at which the largest proportion of plants reached its maximum growth area before withering. Two different methods are used in analyzing each interval. Data obtained for the growth interval are analyzed by determining the difference in the rate at which the green pixel count increased, as well as the difference of between two specific exponential functions fitted to the observed data. Data obtained for the decay interval are also analyzed by determining the difference in the rate at which the green leaf area changed color, as well as the difference of the decay functions fitted to the observed data. A mixture model with autoregressive correlation across time is fitted. It determines the rate at which the green pixels area increased or decreased. Exponential and decay functions are fitted for the second method of analysis. The area under each function is used to determine if there is a significant difference between wild-type plants and the activation-tagged plants. Finally, the difference between the max green pixels counts of the two groups of plants are also compared using a simple t-test.

Example 3A

Cold Germination Assay

A systematic screen to identify novel cold germination-tolerant mutants is presented.

Materials:

Seeds of *Arabidopsis* test lines, resistant and susceptible control lines that are stored no longer than one year are used in the assay to prevent use of seeds with compromised germinability and large variations in germination rates. Freshly harvested seeds are dried at 37° C. for 7 days to assure complete dry down and uniform germination rates. Seeds are passed through a stack of testing sieves of size number 70 (212 μm) on top and 60 (250 μm) at bottom and only seeds of sieve 60 size are used in the assay.

Methods:

Phase 1 Screen: Seeds are soaked in water and incubated at 4° C. for 3 days in the dark. Cold shocked seeds are placed on 0.5×MS, 1% phytagel plates. Eight plates each with a different test line, one plate of the resistant control line and one plate of the susceptible control line are stacked. The stack of plates is wrapped twice in aluminum foil to prevent the seeds from receiving any light. A batch of 12 stacks containing 96 test, 12 resistant and 12 susceptible lines plates is incubated at 6° C. for 4 days in the dark. The batch is transferred to a 4° C. fridge and one stack is pulled out at a time for measurement. One batch is measured in about 4 hours. The total number of seeds and the number of germinated seeds is counted, and the percent of germination at each plate is calculated. Radicle emergence is used as germination indicator. The plates are placed unwrapped at room temperature for one day and the number of germinated seeds is counted to assure seeds are able to germinate at normal temperature and lower seed numbers for the screen are not due to bad seed quality. Lines showing above 70% of germination are considered normal.

Phase 1 Outliers Selection: The Fischer Test is used to calculate a p-value for the difference in germination percent of each T2 line against the average of the 12 susceptible controls in the batch. Minimum significance values for an outlier call are a p-value of 10E-05 and below, and a difference of 5% and two standard deviations and above between the percent of germination of the test line and the average percent of germination of the 96 test lines in the batch.

Phase 2 Screen: Five replicates of the outlier test line and the susceptible control line are cold shocked, plated, grouped in intercalated stacks and wrapped twice in aluminum foil. Stacks are incubated and measured as above. Test lines that show an increase in average percent of germination of 5% and above compared to the susceptible control, and p-values of 0.05 and below at Student's t-tests are selected for candidate gene identification and phase 3 screens.

Phase 3 Screen: Transgenic seeds carrying the candidate gene driven by the CaMV 35S promoter are tested to validate the ability to recapitulate the original phenotype. Transgenic seeds carrying a non-coding sequence driven by the 35S promoter are used as susceptible controls. Test lines that show an increase in average percent of germination compared to the susceptible control with p-values of 0.05 and below at Student's t-tests are considered validated.

Example 3B

Cold Germination Assay Data

Lines were assayed for the cold germination assay essentially as described in the previous Example. Table 8 shows phase 1 screen results for one batch of 96 test lines. Lines number 1 to 6 passed the phase 1 outlier selection criteria. Table 9 shows phase 2 results for the outliers selected on Table 8. All lines passed the phase 2 selection criteria. Table 10 shows results for two lines that passed the phase 3 screen.

The experiment shown in Table 8 had the following values: 96 Tests Average Germination Percent=3.8; 96 Tests Standard Deviation=5.3; and Germination percent at Two Standard Deviations=14.3.

TABLE 8

| N | Total Seed No. | Germinated Seed No. | Germination Percent | P-value Relative to Control Line Average | Test vs. 96 Average Germination Percent Difference |
|---|---|---|---|---|---|
| 1 | 60 | 14 | 23.3 | 1.4E-09 | 19.6 |
| 2 | 91 | 21 | 23.1 | 1.5E-12 | 19.3 |
| 3 | 49 | 11 | 22.4 | 6.2E-08 | 18.7 |
| 4 | 86 | 16 | 18.6 | 2.6E-09 | 14.8 |
| 5 | 57 | 10 | 17.5 | 1.4E-06 | 13.8 |
| 6 | 87 | 14 | 16.1 | 7.5E-08 | 12.3 |
| 7 | 80 | 11 | 13.8 | 3.9E-06 | 10.0 |
| 8 | 73 | 10 | 13.7 | 9.3E-06 | 9.9 |
| 9 | 51 | 6 | 11.8 | 0.0007 | 8.0 |
| 10 | 50 | 4 | 8.0 | 0.02 | 4.2 |
| 11 | 76 | 6 | 7.9 | 0.004 | 4.1 |
| 12 | 66 | 5 | 7.6 | 0.01 | 3.8 |
| 13 | 70 | 5 | 7.1 | 0.01 | 3.4 |
| 14 | 56 | 4 | 7.1 | 0.02 | 3.4 |
| 15 | 86 | 6 | 7.0 | 0.01 | 3.2 |
| 16 | 91 | 6 | 6.6 | 0.01 | 2.8 |
| 17 | 91 | 6 | 6.6 | 0.01 | 2.8 |
| 18 | 63 | 4 | 6.3 | 0.03 | 2.6 |
| 19 | 95 | 6 | 6.3 | 0.01 | 2.6 |
| 20 | 64 | 4 | 6.3 | 0.03 | 2.5 |
| 21 | 84 | 5 | 6.0 | 0.02 | 2.2 |
| 22 | 86 | 5 | 5.8 | 0.03 | 2.1 |
| 23 | 69 | 4 | 5.8 | 0.04 | 2.0 |
| 24 | 56 | 3 | 5.4 | 0.08 | 1.6 |
| 25 | 95 | 5 | 5.3 | 0.03 | 1.5 |
| 26 | 80 | 4 | 5.0 | 0.06 | 1.2 |
| 27 | 60 | 3 | 5.0 | 0.10 | 1.2 |
| 28 | 70 | 3 | 4.3 | 0.13 | 0.5 |
| 29 | 73 | 3 | 4.1 | 0.14 | 0.4 |
| 30 | 102 | 4 | 3.9 | 0.11 | 0.2 |
| 31 | 52 | 2 | 3.8 | 0.23 | 0.1 |
| 32 | 52 | 2 | 3.8 | 0.23 | 0.1 |
| 33 | 80 | 3 | 3.8 | 0.17 | 0.0 |
| 34 | 82 | 3 | 3.7 | 0.18 | -0.1 |
| 35 | 87 | 3 | 3.4 | 0.20 | -0.3 |
| 36 | 68 | 2 | 2.9 | 0.33 | -0.8 |
| 37 | 71 | 2 | 2.8 | 0.34 | -0.9 |
| 38 | 73 | 2 | 2.7 | 0.35 | -1.0 |
| 39 | 74 | 2 | 2.7 | 0.36 | -1.1 |
| 40 | 78 | 2 | 2.6 | 0.38 | -1.2 |
| 41 | 78 | 2 | 2.6 | 0.38 | -1.2 |
| 42 | 82 | 2 | 2.4 | 0.64 | -1.3 |
| 43 | 87 | 2 | 2.3 | 0.65 | -1.5 |
| 44 | 90 | 2 | 2.2 | 0.65 | -1.5 |
| 45 | 97 | 2 | 2.1 | 0.67 | -1.7 |
| 46 | 98 | 2 | 2.0 | 0.67 | -1.7 |
| 47 | 102 | 2 | 2.0 | 0.68 | -1.8 |
| 48 | 52 | 1 | 1.9 | 0.58 | -1.8 |
| 49 | 53 | 1 | 1.9 | 0.59 | -1.9 |
| 50 | 57 | 1 | 1.8 | 0.61 | -2.0 |
| 51 | 64 | 1 | 1.6 | 1 | -2.2 |
| 52 | 68 | 1 | 1.5 | 1 | -2.3 |
| 53 | 69 | 1 | 1.4 | 1 | -2.3 |
| 54 | 73 | 1 | 1.4 | 1 | -2.4 |
| 55 | 74 | 1 | 1.4 | 1 | -2.4 |
| 56 | 74 | 1 | 1.4 | 1 | -2.4 |
| 57 | 77 | 1 | 1.3 | 1 | -2.5 |
| 58 | 78 | 1 | 1.3 | 1 | -2.5 |
| 59 | 78 | 1 | 1.3 | 1 | -2.5 |
| 60 | 82 | 1 | 1.2 | 1 | -2.5 |
| 61 | 91 | 1 | 1.1 | 1 | -2.7 |
| 62 | 93 | 1 | 1.1 | 1 | -2.7 |
| 63 | 93 | 1 | 1.1 | 1 | -2.7 |
| 64 | 93 | 1 | 1.1 | 1 | -2.7 |
| 65 | 116 | 1 | 0.9 | 1 | -2.9 |
| 66 | 123 | 1 | 0.8 | 1 | -2.9 |
| 67 | 108 | 0 | 0.0 | 0.38 | -3.8 |
| 68 | 110 | 0 | 0.0 | 0.38 | -3.8 |
| 69 | 87 | 0 | 0.0 | 0.62 | -3.8 |
| 70 | 80 | 0 | 0.0 | 0.62 | -3.8 |
| 71 | 67 | 0 | 0.0 | 0.61 | -3.8 |
| 72 | 85 | 0 | 0.0 | 0.62 | -3.8 |
| 73 | 75 | 0 | 0.0 | 0.62 | -3.8 |
| 74 | 77 | 0 | 0.0 | 0.62 | -3.8 |
| 75 | 70 | 0 | 0.0 | 0.61 | -3.8 |
| 76 | 88 | 0 | 0.0 | 0.63 | -3.8 |
| 77 | 86 | 0 | 0.0 | 0.62 | -3.8 |
| 78 | 56 | 0 | 0.0 | 1 | -3.8 |
| 79 | 58 | 0 | 0.0 | 1 | -3.8 |
| 80 | 66 | 0 | 0.0 | 0.61 | -3.8 |
| 81 | 96 | 0 | 0.0 | 0.38 | -3.8 |
| 82 | 51 | 0 | 0.0 | 1 | -3.8 |
| 83 | 79 | 0 | 0.0 | 0.62 | -3.8 |
| 84 | 65 | 0 | 0.0 | 0.62 | -3.8 |
| 85 | 74 | 0 | 0.0 | 0.62 | -3.8 |
| 86 | 80 | 0 | 0.0 | 0.62 | -3.8 |
| 87 | 71 | 0 | 0.0 | 0.61 | -3.8 |
| 88 | 81 | 0 | 0.0 | 0.62 | -3.8 |
| 89 | 86 | 0 | 0.0 | 0.62 | -3.8 |
| 90 | 75 | 0 | 0.0 | 0.62 | -3.8 |
| 91 | 60 | 0 | 0.0 | 1 | -3.8 |
| 92 | 105 | 0 | 0.0 | 0.38 | -3.8 |
| 93 | 58 | 0 | 0.0 | 1 | -3.8 |

TABLE 8-continued

| N | Total Seed No. | Germinated Seed No. | Germination Percent | P-value Relative to Control Line Average | Test vs. 96 Average Germination Percent Difference |
|---|---|---|---|---|---|
| 94 | 79 | 0 | 0.0 | 0.62 | −3.8 |
| 95 | 56 | 0 | 0.0 | 1 | −3.8 |
| 96 | 44 | 0 | 0.0 | 1 | −3.8 |

TABLE 9

| | Test Line | | Susceptible Control | | | Test vs. Control |
|---|---|---|---|---|---|---|
| N | Average Germination Percent | Standard Deviation | Average Germination Percent | Standard Deviation | T-TTEST | Germination Percent Difference |
| 1 | 26.8 | 3.7 | 3.9 | 1.4 | 4E−05 | 22.9 |
| 2 | 19.8 | 7.4 | 4.0 | 1.9 | 0.007 | 15.8 |
| 3 | 20.9 | 4.4 | 2.5 | 3.4 | 0.0001 | 18.4 |
| 4 | 21.3 | 4.7 | 2.1 | 2.3 | 0.0002 | 19.2 |
| 5 | 10.4 | 4.2 | 0.3 | 0.7 | 0.005 | 10.0 |
| 6 | 9.8 | 5.4 | 0.4 | 0.9 | 0.02 | 9.3 |

TABLE 10

| | Test Line | | Control Line | | | Test vs. Control | |
|---|---|---|---|---|---|---|---|
| N | Average Germination Percent | Standard Deviation | Average Germination Percent | Standard Deviation | T-TTEST | Germination Percent Difference | Fold Difference |
| 1 | 3.27 | 0.72 | 1.12 | 0.75 | 0.002 | 2.152 | 2.93 |
| 2 | 4.11 | 1.02 | 1.34 | 1.41 | 0.01 | 2.770 | 3.07 |

Example 3C

Chilling Stress at Grain-Fill Cross-Validation Assay

A systematic screen to identify mutants tolerant to chilling stress at grain fill is presented.
Materials and Methods:
Arabidopsis transgenic plants are transformed with a vector carrying the candidate gene cDNA sequence driven by the CaMV 35S promoter and a fluorescent marker. T2 seeds of sieve 60 size (250 μm) are separated into transgenic and non-transgenic pools by fluorescence presence and absence using COPAS™ (Complex Object Parametric Analyzer and Sorter). Transgenic seeds are used as test lines. Non-transgenic lines are used as susceptible controls.

Test and control lines seeds are cold shocked and planted on soil in 100 pots of 2 inch square for each test or control line with excess seed per pot. Seedlings of similar sizes at one week post-germination are selected and excess seedlings are discarded. Plants are grown under non-stressed conditions of 22° C./16 h light and 20° C./8 h dark and inflorescence bolt lengths are monitored from day 30 after planting. Twenty plants per line showing bolts with lengths ranging from 1 to 2 inches are selected for the assay. Ten of the twenty plants are transferred to chilling stress conditions of 7° C./16 h light and 4° C./8 h dark. The remaining ten plants are transferred to control conditions of 22° C./light and 20° C./8 h dark.

After 7 days of incubation, three traits are measured: shoot fresh weight, total branch length and silique number. The shoot of each plant is clipped at the shoot/root junction and the shoot fresh weight is immediately measured. The primary bolt is clipped and primary and secondary branch lengths are immediately measured and summed to calculate the total branch length. The number of plump siliques elongated above petals height is counted. Test lines under stress conditions that show increase relative to the susceptible control in at least one of the three traits measurements with Student's t-test p-value of 0.05 and below are considered as significant positive leads.

Example 3D

Data from Chilling Stress at Grain-Fill Cross-Validation Assay

Lines were assayed as described above. Table 11 shows total branch length (TBL), silique number (SN) and shoot fresh weight (SFW) results for four test lines.

TABLE 11

| N | TBL_Comp | TBL_p | SN_Comp | SN_p | SFW_Comp | SFW_p | CSGF Results |
|---|---|---|---|---|---|---|---|
| 1 | + | 0.22 | + | 0.68 | + | 0.35 | No effect |
| 2 | − | 0.90 | − | 0.83 | − | 0.23 | No effect |
| 3 | + | 0.61 | + | 0.21 | + | 0.52 | No effect |
| 4 | + | 0.05 | + | 0.09 | + | 0.89 | Positive TBL |

Comparison ("Comp") values of "+" or "−" indicate that a test line had a positive or negative trait value as compared to the control line. The p-value is with respect to the difference between the test and control lines.

In Table 11 test line number 4 was positive for total branch length with t-test p-value of 0.05 and was thus considered a significantly positive lead.

Example 4

ABA Response Assay

ABA is involved in a variety of plant development and stress responses. Under drought stress conditions the endogenous level of ABA increases and leads to stomatal closure to prevent transpirational water loss. For ABA mutant screens, inhibition of seed germination by exogenous ABA has been the assay of choice. However, because most of the screens were based on single seed phenotyping, not many mutants with ABA hypersensitivity have been identified through seed germination screen. A quantitative seed germination screen should allow us to capture subtle phenotypes and identify new ABA sensitivity mutants. Screening of transgenic plant lines was done on medium supplemented with low concentration of ABA.
Methods and Materials:
The optimal assay condition was determined by testing multiple Arabidopsis lines at various ABA concentrations. Data generated from these experiments showed that wild-type and most of transgenic seeds displayed consistent germination profiles with 0.6 μM ABA. We also identified a mutant line which is hypersensitive to ABA under this concentration. Therefore 0.6 μM ABA was used for phase 1 mutant screen.

Assay Conditions:

Seeds were surface sterilized and stratified for 96 hrs. About 100 seeds were inoculated in one plate and stratified for 96 hrs, then cultured in a growth chamber programmed for 16 h of light at 22° C. temperature and 50% relative humidity. Germination was scored as the emergence of radicle.

Assay Plan:

A 7-day protocol was carried out to test 96 transgenic *Arabidopsis* lines for ABA sensitivity.

Day 0—Surface sterilized seeds, inoculate seeds onto ABA media, stratified at 4° C. for 4 days.
Day 4—Transfer plates to growth chamber
Day 5—Counted for total seeds on each plate
Day 6—Counted for germination (48 hrs)
Day 7—Counted for germination (72hrs)

Preparation of Media:

| 0.3 µM ABA medium for 1 liter: | |
|---|---|
| MS salt | 2.15 g |
| MES | 0.5 g |
| Adjust pH to 5.7 with KOH | |
| Agar (0.8%) | 8 g |

Autoclave and cool down to 60° C., then add 6 µl of 100 mM ABA into 1 liter medium.

Sterilization of Seeds:

Approximately 50 µl of *Arabidopsis* T2 seeds of the 96 lines to be tested were taken in 1.75 ml microfuge tubes, sterilized in ethanol for 1 min 30 sec, dried in hood.

Inoculation of Seeds:

~100 sterilized seeds for each line were plated onto a single plate. Seeds were stratified at 4° C. for 96 hrs. Plates were then cultured in the chambers set at 16 h of light at 22° C. temperature and 50% relative humidity.

Observations and Results:

Germination was scored as the emergence of radicle over a period of 3 days. Seeds were counted manually using a magnifying lens. The data was analyzed as percentage germination to the total number of seeds that were inoculated. The germination curves are plotted. Like wild-type, most of the transgenic lines have >90% of germination rate at Day 3. Therefore for a line to qualify as outlier, it had to show a significantly lower germination rate (<75%) at Day 3. Usually the cutoff value (75% germination rate) is at least four SD away from the average value of the 96 lines. Data for germination count of all lines and their graphs at 48 hrs, 72 hrs were documented. Table 12 shows the data for one batch (96 lines). The germination of line H3 was inhibited more by ABA than that of other 95 lines so that it was called as an outlier from the screen. Line H3 was identified as a mutant line.

TABLE 12

| Lines | Total Seed # | D 2 Germination # | D 3 Germination # | D 2% | D 3% |
|---|---|---|---|---|---|
| A1 | 71 | 70 | 70 | 98.6 | 98.6 |
| A2 | 104 | 102 | 102 | 98.1 | 98.1 |
| A3 | 84 | 82 | 83 | 97.6 | 98.8 |
| A4 | 89 | 89 | 89 | 100.0 | 100.0 |
| A5 | 69 | 69 | 69 | 100.0 | 100.0 |
| A6 | 80 | 80 | 80 | 100.0 | 100.0 |
| A7 | 98 | 97 | 98 | 99.0 | 100.0 |
| A8 | 89 | 89 | 89 | 100.0 | 100.0 |
| A9 | 101 | 99 | 99 | 98.0 | 98.0 |
| A10 | 97 | 96 | 97 | 99.0 | 100.0 |
| A11 | 90 | 90 | 90 | 100.0 | 100.0 |
| A12 | 69 | 68 | 68 | 98.6 | 98.6 |
| B1 | 118 | 115 | 117 | 97.5 | 99.2 |
| B2 | 67 | 66 | 66 | 98.5 | 98.5 |
| B3 | 73 | 73 | 73 | 100.0 | 100.0 |
| B4 | 73 | 72 | 72 | 98.6 | 98.6 |
| B5 | 71 | 68 | 69 | 95.8 | 97.2 |
| B6 | 101 | 100 | 100 | 99.0 | 99.0 |
| B7 | 63 | 63 | 63 | 100.0 | 100.0 |
| B8 | 117 | 114 | 116 | 97.4 | 99.1 |
| B9 | 76 | 75 | 75 | 98.7 | 98.7 |
| B10 | 84 | 78 | 79 | 92.9 | 94.0 |
| B11 | 66 | 63 | 64 | 95.5 | 97.0 |
| B12 | 60 | 60 | 60 | 100.0 | 100.0 |
| C1 | 72 | 68 | 68 | 94.4 | 94.4 |
| C2 | 58 | 58 | 58 | 100.0 | 100.0 |
| C3 | 81 | 80 | 81 | 98.8 | 100.0 |
| C4 | 62 | 62 | 62 | 100.0 | 100.0 |
| C5 | 59 | 58 | 58 | 98.3 | 98.3 |
| C6 | 82 | 80 | 80 | 97.6 | 97.6 |
| C7 | 112 | 107 | 108 | 95.5 | 96.4 |
| C8 | 64 | 63 | 63 | 98.4 | 98.4 |
| C9 | 115 | 111 | 112 | 96.5 | 97.4 |
| C10 | 73 | 70 | 70 | 95.9 | 95.9 |
| C11 | 81 | 80 | 80 | 98.8 | 98.8 |
| C12 | 62 | 62 | 62 | 100.0 | 100.0 |
| D1 | 105 | 105 | 105 | 100.0 | 100.0 |
| D2 | 75 | 75 | 75 | 100.0 | 100.0 |
| D3 | 81 | 79 | 79 | 97.5 | 97.5 |
| D4 | 75 | 74 | 74 | 98.7 | 98.7 |
| D5 | 56 | 56 | 56 | 100.0 | 100.0 |
| D6 | 89 | 85 | 87 | 95.5 | 97.8 |
| D7 | 123 | 107 | 112 | 87.0 | 91.1 |
| D8 | 84 | 80 | 82 | 95.2 | 97.6 |
| D9 | 71 | 69 | 70 | 97.2 | 98.6 |
| D10 | 94 | 90 | 90 | 95.7 | 95.7 |
| D11 | 117 | 116 | 117 | 99.1 | 100.0 |
| D12 | 70 | 69 | 69 | 98.6 | 98.6 |
| E1 | 59 | 59 | 59 | 100.0 | 100.0 |
| E2 | 62 | 62 | 62 | 100.0 | 100.0 |
| E3 | 67 | 67 | 67 | 100.0 | 100.0 |
| E4 | 92 | 88 | 90 | 95.7 | 97.8 |
| E5 | 57 | 57 | 57 | 100.0 | 100.0 |
| E6 | 94 | 91 | 93 | 96.8 | 98.9 |
| E7 | 151 | 131 | 134 | 86.8 | 88.7 |
| E8 | 95 | 90 | 92 | 94.7 | 96.8 |
| E9 | 71 | 59 | 70 | 83.1 | 98.6 |
| E10 | 76 | 75 | 75 | 98.7 | 98.7 |
| E11 | 137 | 127 | 133 | 92.7 | 97.1 |
| E12 | 152 | 130 | 132 | 85.5 | 86.8 |
| F1 | 100 | 97 | 97 | 97.0 | 97.0 |
| F2 | 75 | 75 | 75 | 100.0 | 100.0 |
| F3 | 92 | 90 | 90 | 97.8 | 97.8 |
| F4 | 76 | 75 | 75 | 98.7 | 98.7 |
| F5 | 70 | 70 | 70 | 100.0 | 100.0 |
| F6 | 78 | 75 | 76 | 96.2 | 97.4 |
| F7 | 139 | 129 | 131 | 92.8 | 94.2 |
| F8 | 87 | 86 | 87 | 98.9 | 100.0 |
| F9 | 83 | 80 | 81 | 96.4 | 97.6 |
| F10 | 70 | 69 | 69 | 98.6 | 98.6 |
| F11 | 103 | 99 | 100 | 96.1 | 97.1 |
| F12 | 84 | 80 | 81 | 95.2 | 96.4 |
| G1 | 88 | 88 | 88 | 100.0 | 100.0 |
| G2 | 101 | 99 | 99 | 98.0 | 98.0 |
| G3 | 70 | 70 | 70 | 100.0 | 100.0 |
| G4 | 87 | 85 | 85 | 97.7 | 97.7 |
| G5 | 69 | 69 | 69 | 100.0 | 100.0 |
| G6 | 77 | 76 | 76 | 98.7 | 98.7 |
| G7 | 77 | 75 | 77 | 97.4 | 100.0 |
| G8 | 94 | 90 | 91 | 95.7 | 96.8 |
| G9 | 70 | 69 | 69 | 98.6 | 98.6 |
| G10 | 70 | 70 | 70 | 100.0 | 100.0 |
| G11 | 81 | 80 | 80 | 98.8 | 98.8 |
| G12 | 57 | 57 | 57 | 100.0 | 100.0 |
| H1 | 67 | 65 | 66 | 97.0 | 98.5 |

TABLE 12-continued

| Lines | Total Seed # | D 2 Germination # | D 3 Germination # | D 2% | D 3% |
|---|---|---|---|---|---|
| H2 | 79 | 78 | 78 | 98.7 | 98.7 |
| H3 | 145 | 90 | 96 | 62.1 | 66.2 |
| H4 | 74 | 74 | 74 | 100.0 | 100.0 |
| H5 | 113 | 110 | 112 | 97.3 | 99.1 |
| H6 | 67 | 65 | 65 | 97.0 | 97.0 |
| H7 | 82 | 82 | 82 | 100.0 | 100.0 |
| H8 | 68 | 68 | 68 | 100.0 | 100.0 |
| H9 | 92 | 90 | 92 | 97.8 | 100.0 |
| H10 | 92 | 90 | 91 | 97.8 | 98.9 |
| H11 | 71 | 71 | 71 | 100.0 | 100.0 |
| H12 | 84 | 82 | 83 | 97.6 | 98.8 |

TABLE 13

Percentage Germination Data for Line H3 with Standard Deviation

| Days | 0 | 2 | 3 |
|---|---|---|---|
| Average | 0 | 97.2 | 98.1 |
| H3 | 0 | 62 | 66 |
| Stddev | 0 | 4.8 | 3.9 |

Figure 12B:
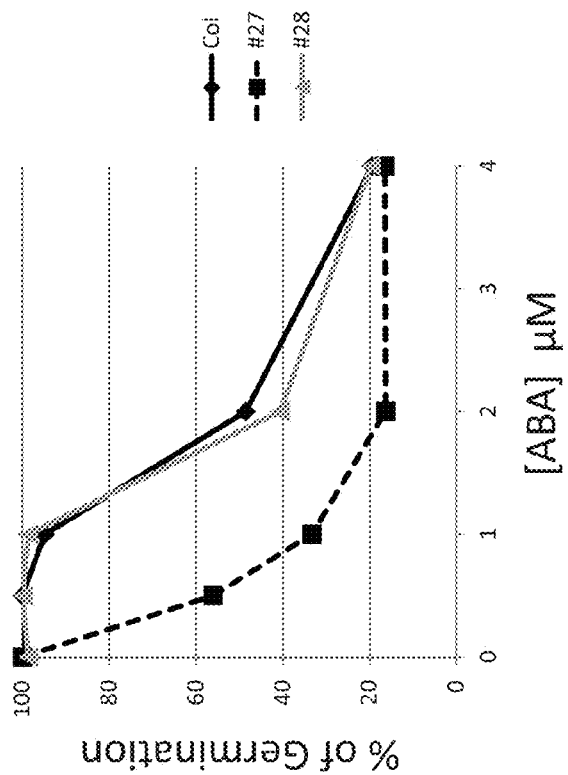
FIG. 12A and FIG. 12B present graphs for seed germination on 0.6 µM ABA. Line #27 was identified as an ABA-Hypersensitive line.
Figure 12A:
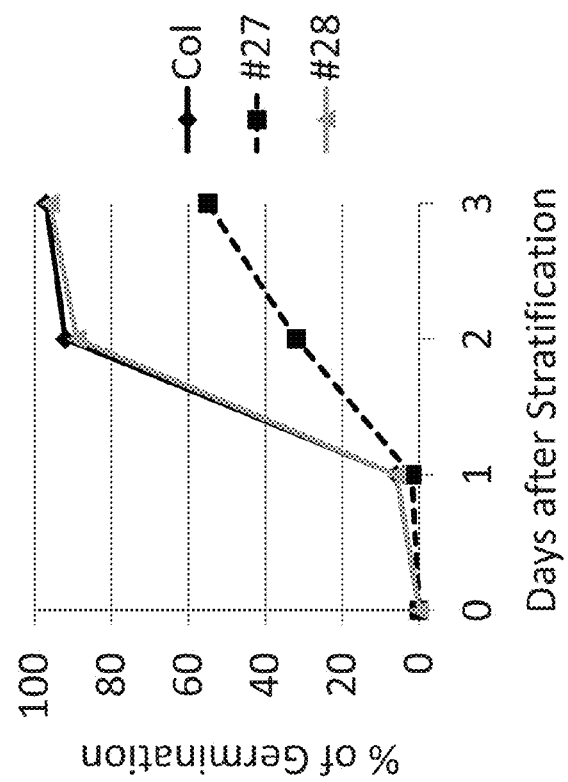

FIG. 12A and FIG. 12B present graphs for seed germination on 0.6 µM ABA. Line #27 was identified as an ABA-Hypersensitive line.

Figure 13:
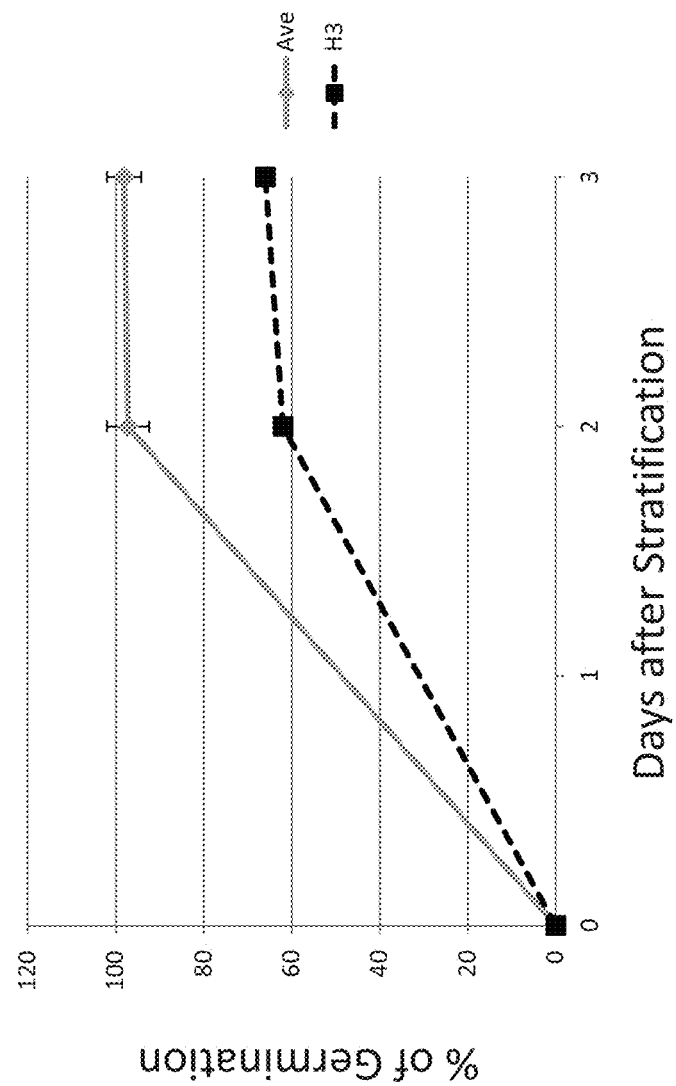
FIG. 13 shows the STDDEV for 96 Lines (Plate #015). An ABA hypersensitive line (H3) is shown.

FIG. 13 shows the STDDEV for 96 Lines (Plate #015). An ABA hypersensitive line (H3) is shown.

Example 5

Paraquat Tolerance Assay

Most types of abiotic stresses such as drought, salinity, flooding, heat and cold stresses disrupt the metabolic balance of cells, resulting in enhanced production of reactive oxygen species (ROS). Critical for plant survival and productivity is the ability of plants to perceive and respond to ROS. The goal of the paraquat screen is to isolate mutant lines that exhibit enhanced growth in the presence of oxidative stress.

In light-exposed plants, paraquat accepts electrons from photosystem I and transfers them to molecular oxygen. In this manner, destructive reactive oxygen species are produced. A range of paraquat concentrations were tested in *Arabidopsis*. Paraquat at 0.01-0.1 µM resulted in a dose-dependent growth inhibition and leaf bleach. Compared to wild-type plants, mutant plants have larger size and less-bleached leaves under these conditions. A quantitative assay based on leaf area and color (similar to low N plate analysis) can be easily integrated into this screen.

Methods and Materials:

The dose effect of paraquat on *Arabidopsis* growth was determined. Data generated from the testing experiments indicated: 1) 0.03 µM of paraquat greatly inhibited *Arabidopsis* growth; 2) after 7-day-growth at this concentration, plants will recover once transferred to regular MS medium. Therefore this concentration was used for paraquat resistance assay. We also found that ecotype Tsu showed enhanced resistance to paraquat. Tsu can serve as a positive control for this assay.

Assay Conditions:

Seeds were surface sterilized and stratified for 96 hrs. 18 seeds for each tested line and Col-0 were inoculated in one plate, then cultured in a growth chamber programmed for 16 h of light at 22° C. temperature, 150 µE light intensity and 50% relative humidity. Growth phenotype was scored based on leaf size and color at 7-day-after inoculation.

Assay Plan:

A 10-day protocol was carried out to test 96 transgenic *Arabidopsis* lines for ABA sensitivity.

Day 0—Surface sterilized seeds; stratified at 4° C. for 4 days.

Day 4—Inoculated onto paraquat plates and cultured plates in growth chamber.

Day 11—Checked for growth and scanned the plates.

Preparation of Media:

| Paraquat medium for 1 liter: | |
|---|---|
| MS salt | 2.15 g |
| MES | 0.5 g |
| Adjust pH to 5.7 with KOH | |
| Agar (0.8%) | 8 g |

Autoclave and cool down to 60° C., then add 300 µl of 100 µM paraquat into 1 liter medium.

Sterilization of Seeds:

Approximately 10 µl of *Arabidopsis* T2 and Col-0 were taken in 1.75 ml microfuge tubes, sterilized in 50% bleach with 0.1% tween20 for 10 min, followed by five washes with sterile water. Seeds were stratified at 4° C. for 4 days before inoculation.

Inoculation of Seeds:

Seeds were inoculated on a square paraquat plate. 18 seeds of test lines and 18 seeds of Col-0 were evenly put on the plate side by side. Plates were then cultured in the chambers set at 16 h of light at 22° C. temperature, 150 µE light intensity and 50% relative humidity.

Observations and Results:

The growth of *Arabidopsis* plants is strongly inhibited by paraquat. The effect of paraquat can be detected at the concentration 0.01 µM. At concentration of 0.03 µM, cotyledons of Col-0 plants failed to expand and turned brow-yellowish. Root growth and true leaf initiation were arrested, and plants died one-week-after germination. We have tested 77 transgenic lines at this condition. Each line was directly compared with Col-0 grown side by side on the same plate. Five transgenic lines were identified as paraquat-resistant lines. These lines have bigger size and greener cotyledons compared with Col-0.

Example 6

Root Hydrotropism Assay

Figure 14:
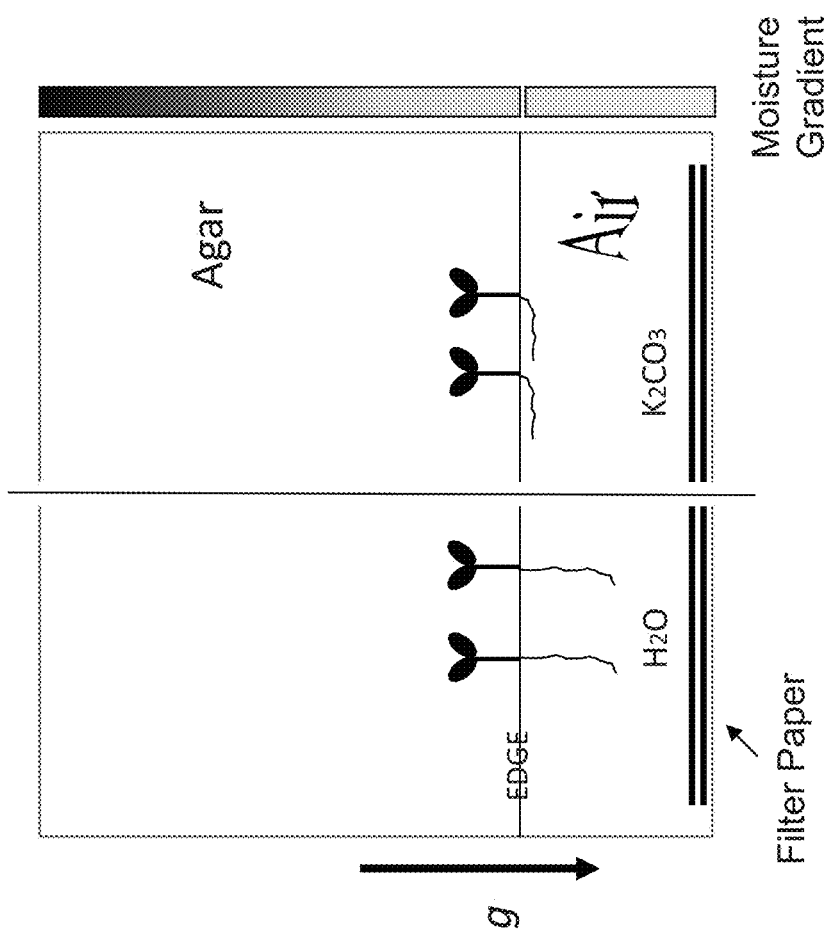
FIG. 14 shows the schematic representation for the dish-based root hydrotropism assay.
Figure 15B:
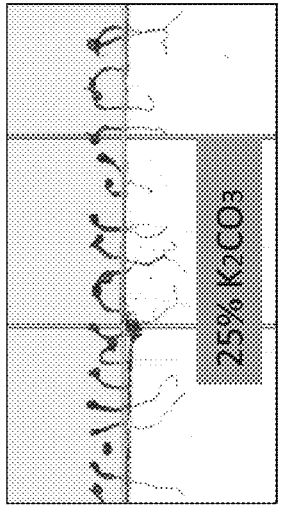
FIG. 15A-FIG. 15F show root growth responses to moisture gradients.
Figure 15D:
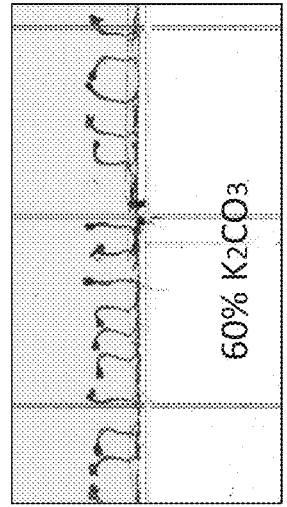
Figure 15F:
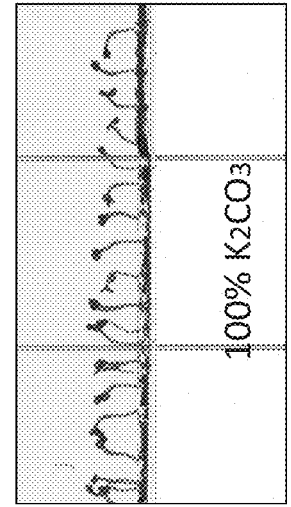
Figure 15A:
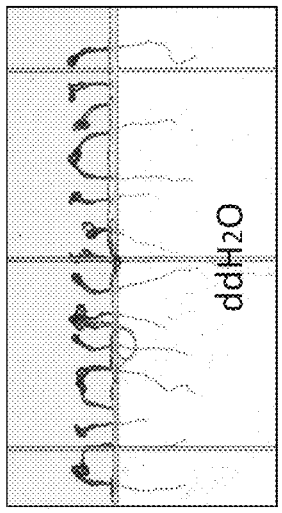
Figure 15C:
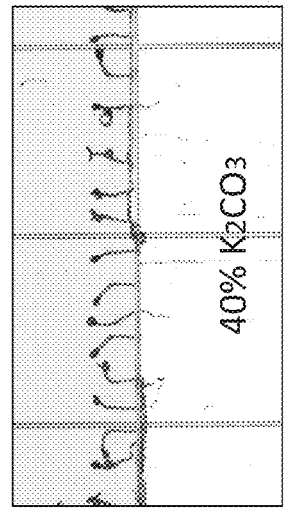
Figure 15E:
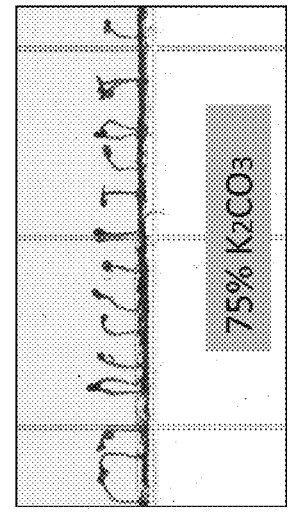

Root hydrotropism (RH) in nature is thought to be important for chasing water. Hydrotropism is rarely studied and poorly understood, and only few mutants with decreased hydrotropic response have been isolated. Forward genetic analysis of hydrotropism in *Arabidopsis* could help us to identify the key genes involved in sensing and responding to moisture gradients. Understanding hydrotropism in roots could lead to methods for improving crop WUE. A screen system was created by established a moisture gradient inside a vertically oriented Petri dish (FIG. 14). Various humidity gradients were created around the roots with different concentrations of $K_2CO_3$. For RH mutant screens, root growth response to different moisture gradients was tested. Roots of wild type generally showed a positive curvature to avoid the air space with low moisture when the concentration of $K_2CO_3$ reaches to 40% (FIG. 15C). Based on these results, we implemented a screen to isolate mutants with either enhanced or decreased root hydrotropic response.

Figure 16:
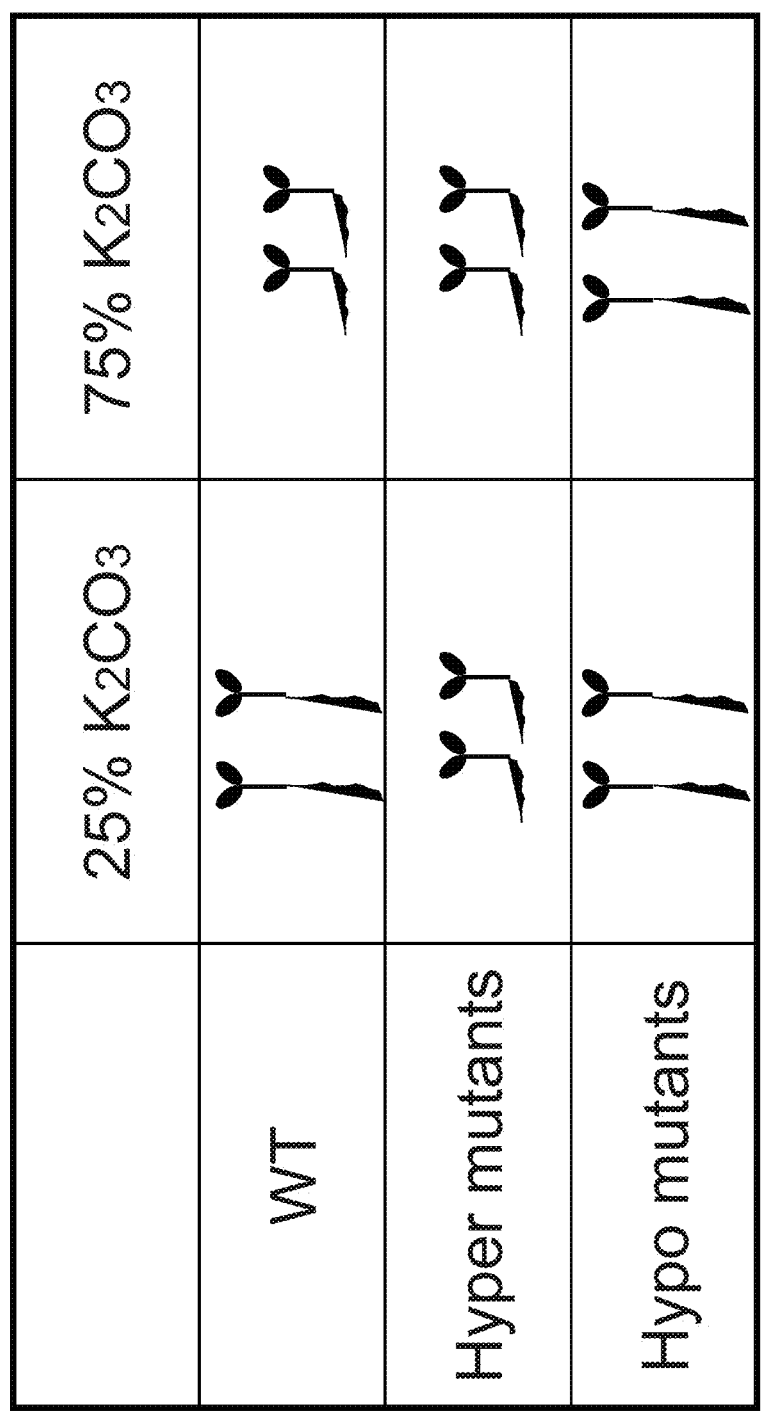
FIG. 16 shows the root hydrotropism screen.

Methods and Materials:

The optimal assay condition was determined by testing wild type *Arabidopsis* plants at various $K_2CO_3$ concentrations. 75% and 25% of K2CO3 concentration were chosen for hypo-hydrotropism and hyper-hydrotropism mutants, respectively (FIG. 16).

Assay Conditions:

Seeds were surface sterilized and stratified for 96 hrs. About 20 seeds were inoculated in one plate, cultured vertically in a growth chamber programmed for 16 h of light at 22° C. temperature and 50% relative humidity. Root elongation pattern was recorded after 7 day growth.

Assay Plan:

An 11-day protocol was carried out to test 96 transgenic *Arabidopsis* lines for ABA sensitivity.

Day 0—Surface sterilized seeds; stratified at 4° C. for 4-7 days.

Day 4—Cut the bottom part of agar medium and inoculated 20 seeds on the cutting edge. Put two filter paper soaked with $K_2CO_3$ solution at the bottom of the plates. Culture the plates in a growth chamber.

Day 11—Check root elongation and scanned the plates.

Preparation of Media:

| ½ × MS medium for 1 liter: | |
| --- | --- |
| MS salt | 2.15 g |
| MES | 0.5 g |
| Adjust pH to 5.7 with KOH | |
| Agar (0.8%) | 8 g |

Sterilization of Seeds:

Approximately 10 μl of *Arabidopsis* T2 and Col-0 were taken in 1.75 ml microfuge tubes, sterilized in 50% bleach with 0.1% tween20 for 10 min, followed by five washes with sterile water. Seeds were stratified at 4° C. for 4 days before inoculation.

Plate Setup:

Square Petri dishes were used for making the plates. Once medium solidified, cut and remove the bottom part of agar (~2 cM). To establish the moisture gradient, two pieces of filter paper soaked with $K_2CO_3$ solution were put at the bottom of the plate.

Inoculation of Seeds:

~30 sterilized seeds for each line were planted on the cutting edge of the agar medium. Plates were then cultured vertically in the chambers set at 16 h of light at 22° C. temperature and 50% relative humidity.

Observations and Results:

Root elongation pattern was checked after 7 day growth in chamber. Plates were scanned and outliers were identified. When wt roots were exposed to a moisture gradient established in a closed Petri dish by 75% of $K_2O_3$, they bent upward toward the agar, although they elongated downward in a high humidity plates. Using this system, we isolated hydrotropism mutants whose roots displayed altered hydrotropic responses (FIG. 17A-FIG. 17D).

Example 7A

Growth Rate Assay

Plants can be measured for growth rate under stressed or non-stressed conditions. Growth under non-stressed conditions may involve the following: (a) Soil: Metromix 360; (b) Fertilizer: Osmocote and Peter's; (c) Light Regime: 16 hours light/8 hours dark; (d) Light Intensity: 150 μE; (e) Temperature Regime: 22° C. day/20° C. night; and (f) Humidity: 50% Relative Humidity.

Flats are configured with 8 square pots each. Each pot (or cell) is sown to produce 9 wild-type or 9 mutant seedlings in a 3×3 array. Digital images of the plants are taken on a predetermined schedule, e.g., see Table 14. Leaf area is measured in terms of the number of green pixels obtained using the LemnaTec imaging system.

TABLE 14

| Day of Experiment | Treatment | Time Period |
| --- | --- | --- |
| Day 1 | Cold Shock | 2 days |
| Day 3 | Plant Seeds | 4 days |
| Day 7 | Basta Spray 1 | 2 days |
| Day 9 | Basta Spray 2 | 2 days |
| Day 11 | Thin Seedlings | 3 days |
| Day 14-Day 27 | Lemna Tec Measurement | Daily |

From the *Lemna* Tec data, comparisons are made between mutant and wild-type plants and P-values are determined for growth area, growth slope and maximum day area.

Example 7B

Growth Rate Assay Data

Results from a growth rate assay for a mutant line are shown in Table 15.

TABLE 15

| MT | gro_comp | gro_area_p | slope_gro_comp | gro_slope_p | max_comp | max_p |
| --- | --- | --- | --- | --- | --- | --- |
| MT | + | 0.018889996 | + | 0.016462855 | + | 0.092408867 |

Comparison ("Comp") values of "+" indicate that a mutant ("MT") line had a positive growth value as compared to wild-type. The p-value is with respect to the difference between the mutant line and wild-type.

In Table 15, the mutant line was positive for growth area and growth slope with p-values of 0.019 and 0.016, respectively, and is thus considered a significantly positive lead.

Example 8A

AT-BSO/High Light Tolerance Assay

Most types of abiotic stresses such as drought, salinity, flooding, heat and cold stresses disrupt the metabolic balance of cells, resulting in enhanced production of reactive oxygen species (ROS). Critical for plant survival and productivity is the ability of plants to perceive and respond to ROS. The goal of the 3-amino-1,2,4-triazole (AT)-buthionine S, R-sulfoximine (BSO)/high light screen is to isolate mutant lines that exhibit reduced damage in the presence of oxidative stress.

For this assay AT, BSO and high light are used to cause a photobleaching phenotype caused by ROS stress. The addition of AT to plants increases both $H_2O_2$ (a ROS) as well as glutathione levels which work to decrease $H_2O_2$ levels. In order to assure a stress from $H_2O_2$ BSO is added which is an inhibitor of glutathione. In this assay the low levels of AT-BSO by themselves would not cause photobleaching under normal growing conditions. Therefore, *Arabidopsis* seedlings are incubated on plates containing AT-BSO under normal growth conditions for 7 days then transferred to a high light environment. Evaluation of photobleaching is carried out by eye after 4 days of growth in high light.

Methods and Materials:

*Arabidopsis* seeds are germinated and grown on 30 mL of ½ MS plates containing AT and BSO at a final concentration on 1 µM/mL and 0.2 mM/mL respectively. Plates are grown at normal conditions for 7 days and then transferred to high light conditions for 4 days. Plants which are not photobleached are then transferred to regular ½ MS plates for recovery before then being transferred to soil to grow to seed.

Assay Conditions:

Seeds are surface sterilized and stratified for 3 days. 25 seeds are inoculated per plate then cultured in a growth chamber programmed for 16 hours light at 22° C. temperature 150 µE light intensity and 50% relative humidity for 7 days. Plates are then transferred to very high light conditions (600 µE) for 4 days. Plants are then evaluated for photobleaching (yes/no) by eye.

The reduced photobleaching phenotype is scored visually. A plant exhibiting the "reduced photobleaching phenotype" has the majority of its leaf area as pale-green and/or dark-green with little or no yellow or white color, when grown under conditions in which wild-type plants (and non-responsive mutant plants) are "photobleached", i.e., they have the majority of their leaf area as pale-green, yellow and/or white with noticeable yellow or white color.

Assay Plan:

Day 0—Surface sterilize seeds and stratify at 4° C. for 3 day.
Day 3—Inoculate onto ½ MS agar containing AT and BSO and culture plates in growth chamber.
Day 10—Transfer plates to high light growth conditions
Day 15—Evaluate photobleaching.

Preparation of Media:

| AT-BSO medium for 1 liter: | |
| --- | --- |
| MS salt | 2.15 g |
| MES | 0.5 g |
| Adjust pH to 5.7 with KOH | |
| Agar (0.8%) | 8 g |
| AT(10 mM) | 50 µL |
| BSO(100 mM) | 1 mL |

Pour 30 mL per plate

Sterilization of Seeds:

Seeds are sterilized in 50% bleach/0.1% tween20 solution for 10 minutes, followed by 5 washes with sterile water. Seeds are stratified at 4° C. for 3 days prior to inoculation.

Inoculation of Seeds:

Seeds are inoculated on square AT-BSO plates. 25 seeds are inoculated per plate evenly spaced over entire plate.

Example 8B

AT-BSO/High Light Tolerance Assay Data

Figure 18:
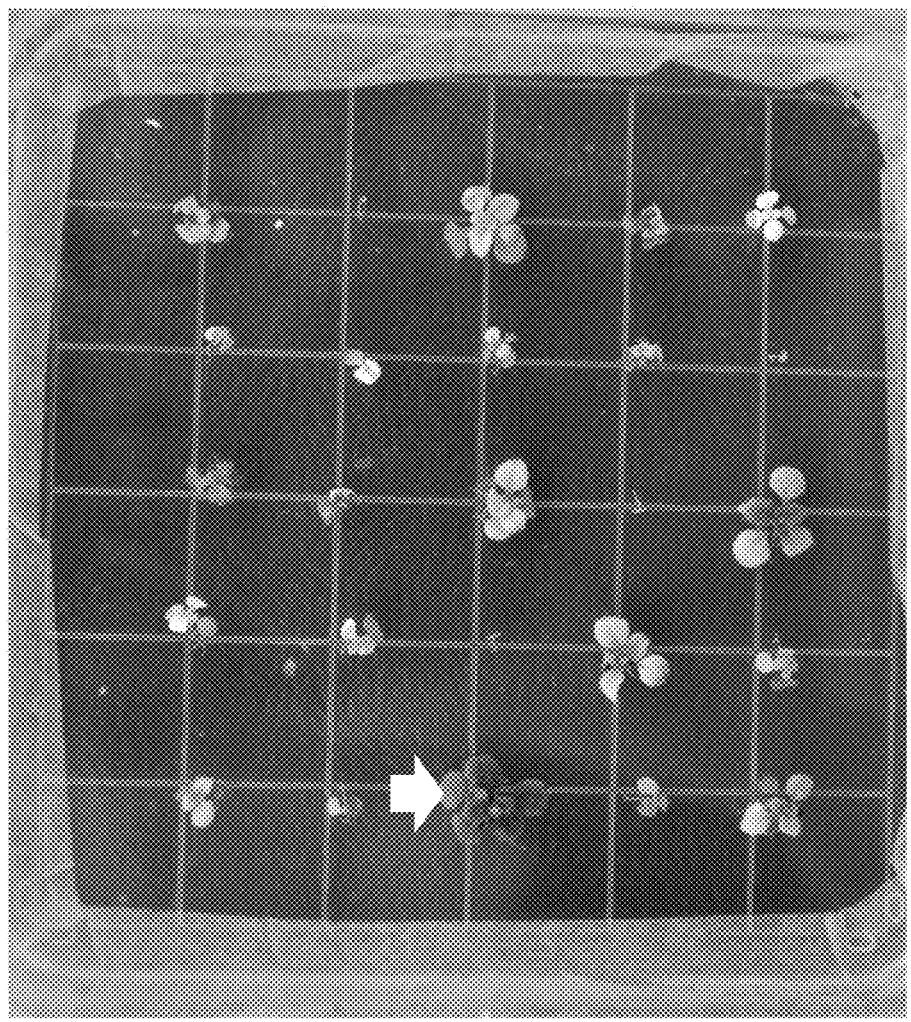
FIG. 18 shows the results of the AT-BSO high light screen. On the plate most of the plants are yellowish/white but there is one plant that is still green, i.e., what a positive outlier looks like. It is marked by a white arrow.
Figure 19:
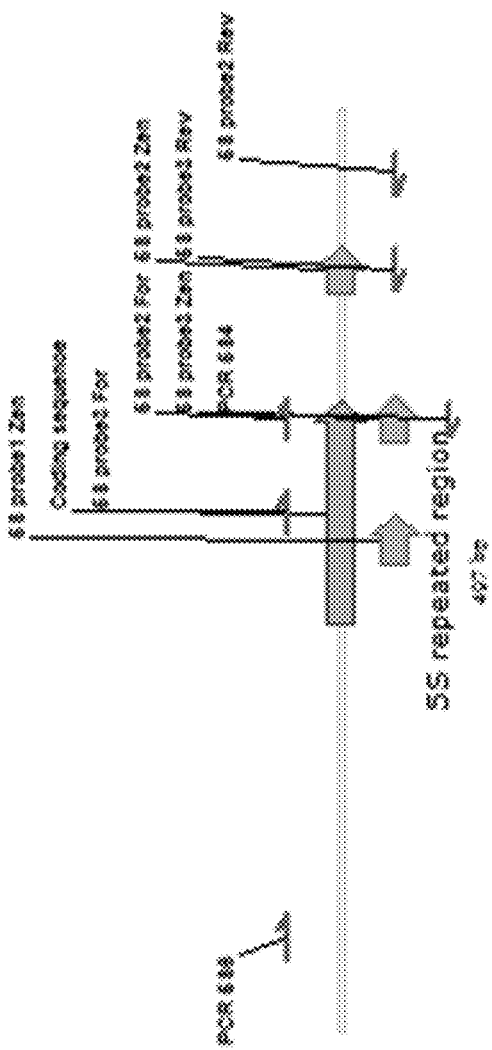
FIG. 19 shows the positions of the different probe and primer sequences in the 5S rRNA repeated region, used for the soil root mass assay.

Plants were screened in the AT-BSO/High Light Tolerance Assay as described above. An example of a plant showing the reduced photobleaching phenotype is presented in FIG. 18.

Example 9

Soil Root Mass Assay to Identify Genes with an Improved Total Root Mass When Grown in Soil This assay has been designed in order to study the growth of *Arabidopsis thaliana* roots in soil. Since the *Arabidopsis* root system is very fine and roots cannot be easily separated from the soil in which they grow, most of the root architecture analysis in *Arabidopsis* has to be done in plates. We have developed a method to indirectly measure the total amount of roots grown in soil by using a marker easily quantifiable. Although the description in this example refers to plants grown in non-stressed conditions, the same assay can be used to measure the response of root growth to abiotic stresses such as drought and low nitrogen.

Transgenic seeds from individual T2 lines from our 35S activation tagged population were identified using the COPAS™ *Arabidopsis* seed sorting instrument (Melamed-Bessudo, C. et al. *Plant J.* (2005) 43: 458-466).

16 individual T2 lines were screened in each flat containing 128 cells. Three T2 transgenic seeds were planted in each cell filled with Metromix 360. After one week of growth, the seedlings were thinned to leave only one seedling per cell. Plants were grown for one month at 22° C. light and 20° C. dark with 16 hours light, 8 hour dark and an average light intensity of ~180 µmol/m$^2$/s at 65% humidity. They were watered three times a week and fertilized.

Every flat had 8 cells containing Columbia wild type seeds used as controls. After one month of growth, flats were saturated with water and the healthiest 7 plants/line were selected. Shoots and any green tissue was removed at soil level and the soil from the 7 cells containing root tissue from a single line was pooled into a blender containing 100 ml of 2×DNA extraction buffer.

| | |
| --- | --- |
| 400 ml | 1M Tris pH 7.5 |
| 29.22 g | NaCl |
| 100 ml | 0.5M EDTA pH 8.0 |
| 50 ml | 20% SDS |
| ~450 ml | H$_2$O (final volume of 1.0 L) |

Soil mixture was blended for 2 minutes and the slurry was transferred to a 50 ml Falcon tube and centrifuged at 4,000 rpm for 10 minutes. The supernatant was collected and 250 µl were used for DNA extraction using the PowerSoil-htp kit and following the manufacturer protocol (MO BIO Laboratories, Inc.).

DNA was resuspended in 100 microliters and 1.0 µl was used as a substrate for a Quantitative Real Time PCR run using a primer pair designed using *Arabidopsis* 5S ribosomal DNA.

Primer Sequences:

Initial Primer & Probe Sequences:

```
5S4 (SEQ ID NO: 4):
CGTGATTTGGGCTATATTACGGACCC

5S6 (SEQ ID NO: 5):
GAGGGATGCAACACGAGGAC

Probe1 (SEQ ID NO: 6):
TCCCATCAGAACTCCGCAGTTAAGCGTT
```

4 replicates per sample were run on the Roche Light Cycler 480 instrument and the Absolute Quantification Analysis/2$^{nd}$ Derivative Maximum program within the supplied Roche software was used to quantify the amount of 5S rDNA amplified in each sample.

T2 lines with a DNA concentration 10% higher than either the Columbia WT control grown in the same flat or to the average of the whole experiment of flats sown the same day were designated as Phase 1 hits.

Phase 1 hits will be tested using the same assay conditions one more time and if they pass with the same criteria, they can be used for molecular identification of the DNA flanking the T-DNA insertion.

Example 10A

Suppressor Screening to Identify Genes that Suppress the nlp7 Mutant Phenotype

The *Arabidopsis thaliana* NIN-like protein 7 (NLP7) gene (At4g24020) was originally described by Castaings et al. (*Plant J.* (2009) 57:426-435) as a gene that modulates nitrate sensing and metabolism in *Arabidopsis*. *Arabidopsis* nlp7 knock-out mutants (nlp7 KO) constitutively show several features of nitrogen-starved plants. nlp7 KO mutants are impaired both in the transduction of the nitrate signal and in the assimilation of nitrate. We designed a screening that would allow us to identify genes that can suppress the nitrogen-starved phenotype displayed by the nlp7 KO mutant. Those genes were considered as candidate genes involved in nitrogen signal transduction and/or assimilation. Activation-Tagged Population Development in nlp7 Knockout Mutant Background:

An activation-tagged population in the nlp7 KO mutant background was created and used for screening.

The SALK_026134 line was requested from Salk Institute Genomic Analysis Laboratory (Alonso et. al. *Science* 1 Aug. 2003; 301 (5633): 653-657). This line contains a T-DNA insertion in the second exon of the At4g24020 gene. Genotyping of the seedlings to identify homozygote insertions was done with the following primer set. LBb1 is the priming site on the T-DNA insertion that SALK used in creating their mutant population.

```
Salk_026134 LP (SEQ ID NO: 1):
CAGTTTTTCTTTAGACCGCCAC

Salk_026134 RP (SEQ ID NO: 2):
AGCAGCTGAGAACACAACAGAG

LBb1 (SEQ ID NO: 3):
GCGTGGACCGCTTGCTGCAACT
```

PCR reactions for genotyping were done on crude single leaf DNA preps in 20 µl reactions.

| 2x PCR Mix | 10.0 ul |
|---|---|
| LP | 0.2 µl of a primer stock of 20 micro molar |
| RP | 0.2 µl of a primer stock of 20 micro molar |
| LBb1 | 0.1 µl of a primer stock of 20 micro molar |
| H2O | 8.5 µl |
| DNA | 1.0 µl |

PCR cycling conditions were:

| 94° C. | 5:00 mins |
|---|---|
| 94° C. | 0:30 mins |
| 62° C. | 0:30 mins |
| 72° C. | 1:30 mins |
| Go to step 2, 35 cycles | |
| 72° C. | 7:00 mins |
| 4° C. | ∞ |

Phenotypic analysis was performed on the homozygote nlp7 KO line, confirming a nitrogen starved phenotype, both at the root level (measured as root growth on plates containing 10 mM potassium Nitrate) and at the shoot level (growth of 3 week plants in Metromix, fertilized with Osmocote).

Figure 20B:
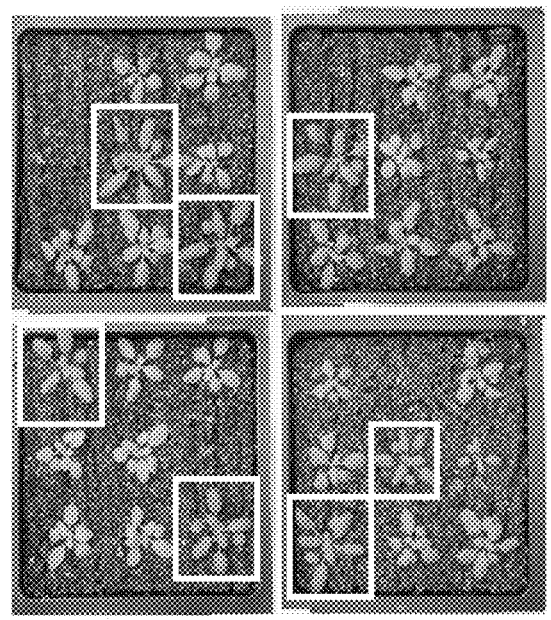
FIG. 20B shows that when grown on metromix and Osmocote mix, nlp7 mutants show a smaller and pale rosette when grown in soil, compared to the Columbia wild type rosettes grown in the same pot. The wt plants are shown enclosed by a white box.
Figure 20A:
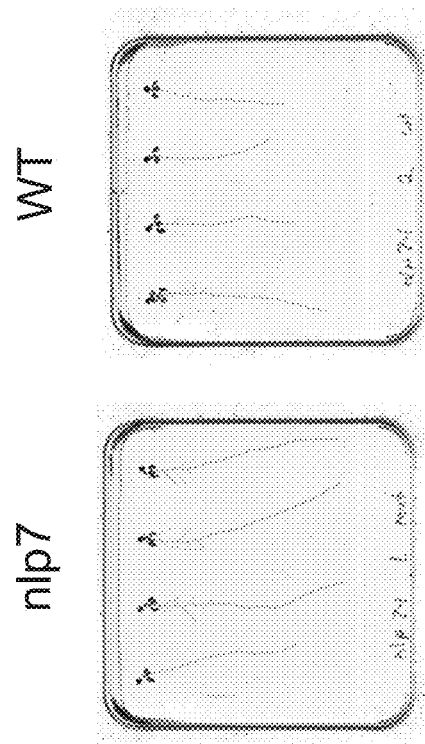
FIG. 20A shows 2 plates with nlp7 KO and wt plants on 10 mM nitrogen concentration, showing lower shoot/root ratio for the mutant line when compared to the wt plants.

FIG. 20A and FIG. 20B show the phenotypes observed. nlp7 KO mutant shows longer primary root than wild type seedlings at 10 days after germination (shoot/root ratio is lower in mutant; FIG. 20A). Also, nlp7 mutants show a smaller and pale rosette when grown in soil, compared to the Columbia wild type rosettes grown in the same pot (FIG. 20B).

A stock of the homozygote nlp7 mutant was created and used for *Agrobacterium* transformation with the binary plasmid pKR1006. This T-DNA based binary construct contains four multimerized enhancer elements derived from the Cauliflower Mosaic Virus 35S promoter, corresponding to sequences −341 to −64, as defined by Odell et al. (1985) *Nature* 313:810-812. It also contains a DS-RED fluorescent marker under the control of the SCP promoter. This marker can be used to select transformed seeds containing the T-DNA element and the 35S enhancer.

Insertions of the transcriptional enhancer elements can dominantly activate and/or elevate the expression of nearby endogenous genes. By making a large population with these enhancer elements randomly inserted throughout the genome, one can assess the ability of nearly every gene to modify the trait being assayed, in this case to suppress or enhance the rosette phenotype of the nlp7 mutants.

Example 10B

Screens to Identify Lines with nlp7 Suppression Phenotype

Transgenic T1 seeds from the nlp7 activation tagged population were identified using the COPAS™ *Arabidopsis* seed sorting instrument selecting for Red Fluorescent seeds.

16 T1 transgenic seeds per pot were planted in Metromix 360, fertilized with Osmocote and grown for 25 days at 22° C. light and 20° C. dark with 16 hours light, 8 hour dark and an average light intensity of ~180 µmol/m²/s.

Every flat, containing 8 pots, had 4 Columbia wild type seeds, used as controls. After 25 days of growth, seedlings were scored by eye for size and green color.

Plants with a visible increase in greenness or size, when compared to the average of the whole experiment of flats sown the same day and resembling the color and/or size of the Columbia wild type rosettes, were designated as Phase 1 hits. Phase 1 hits were kept, genotyped to confirm the nlp7 mutation, and T2 seeds from them were re-screened under the same assay conditions (Phase 2). During Phase 2, each flat contained 2 different T2 lines (4 pots each line for a total of 64 seedlings per line). When the Phase 2 lines showed a consistent difference in color or size from the mean of the whole experiment of flats sown the same day, the line was considered a validated nlp7 suppressor line.

The nlp7 suppressor lines were then used for molecular identification of the DNA flanking the T-DNA insertion.

Example 11A

ABA/Root Growth Assay

Plants being sessile have evolved a higher adaptability to overcome adverse environmental challenges. The phytohormone abscisic acid (ABA) is a key endogenous messenger in plants' responses to such stresses and therefore understanding ABA signaling is essential for improving plant performance especially under drought stress. Drought is a very complicated phenomenon involving several key regulators and in order to capture wide spectrum of such players a multi-assay approach is imperative. A root growth assay has been developed keeping this objective in mind.

In the ABA/Root assay, the sensitivity of root growth on media containing ABA post germination on MS media is used as the assay criterion. This enables us to potentially capture both hypersensitive and hyposensitive outliers/leads making it a powerful tool for screening of new genes and as a cross validation assay.

The ABA/Root assay is a two phase assay. Phase I includes growing seeds on plain germination/MS media vertically under 230 μMol light intensity. After 5 days of germination, seedlings are picked and transferred to media comprising of ABA. The position of the root tip at the time of transfer is marked. The seedlings are allowed to grow vertically for 7 days on media containing ABA with daily rotation of plates such that each plate received uniform light. On the seventh day, the plates are imaged and root phenotypes are analyzed. The overall schematic of the assay is presented in FIG. 21.

Example 11B

ABA/Root Growth Assay Standardization

Figure 22A:
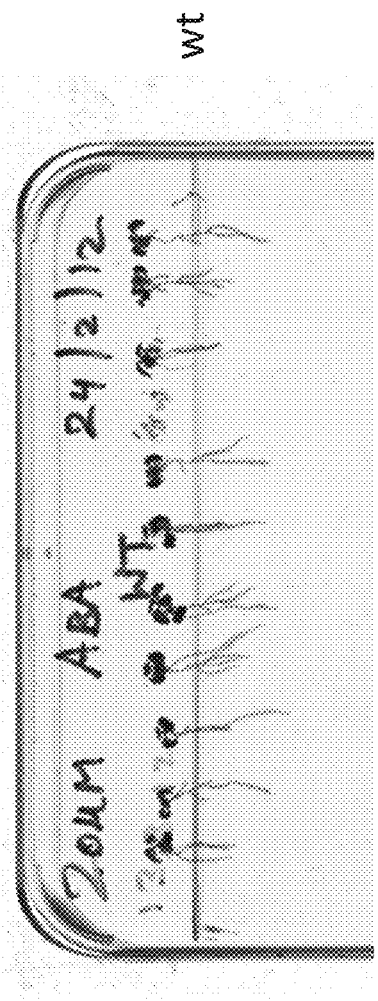
FIG. 22A-FIG. 22B show a comparison between wt and pDKC-ABA-R1 YFP positive line on MS supplemented with 20 µM ABA.
Figure 22B:
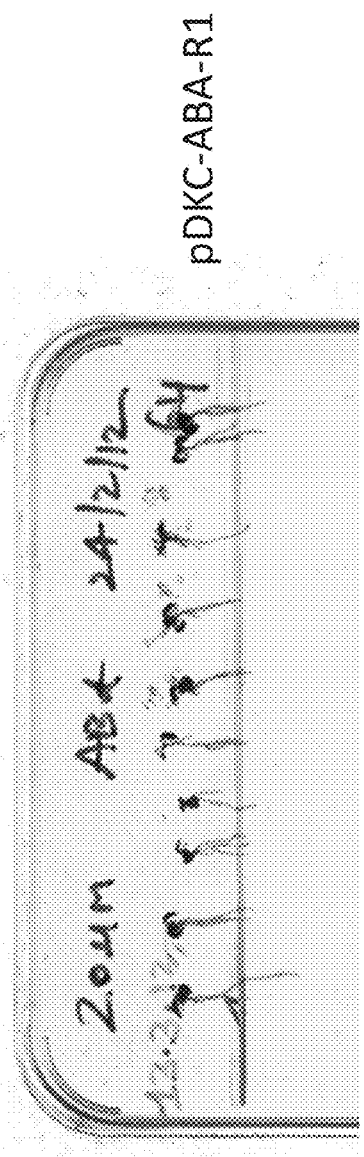

We performed over 6 standardization experiments in which we tested root sensitivity phenotype to 0, 2.5, 5, 10, 15, 17.5, 20, 25 and 30 μM ABA concentrations. We used WT seeds as negative controls whereas seeds from pDKC-ABA-R1 were used as positive controls. pDKC-ABA-R1 is a cDNA of an *Arabidopsis* gene cloned in pBCyellow background. This *Arabidopsis* gene is a validated lead both in drought tolerance and ABA hypersensitive assays. Representative results from the experiment are shown in FIG. 22A-FIG. 22B. Based on these standardization assays, 20 μM ABA was selected for further assays.

Example 11C

ABA/Root Growth Assay Conditions

In this assay, with an ABA hypersensitive outlier we expect to observe seedlings arrested at the point of transfer whereas for ABA hyposensitive outliers we expect the roots to continue to grow because of their inability to sense ABA in the media. For lines that are insensitive, we expect them to behave similar to WT.
Assay Conditions:

Seeds are surface sterilized first with 100% ethanol followed with bleach+Tween 20 solution followed by 4 washes of sterile water and stratified for 48 hrs. Two rows of around 30 stratified seeds each are sown on germination media and the plates are kept vertically in the growth chamber for 5 days. The growth chamber settings are 16 h of 230 μMol light at 22° C. temperature and 50% relative humidity. After 5 days, the seedlings are picked one by one and transferred to media containing 20 μM ABA. The seedlings are grown vertically for 7 days. After 7 days, root phenotypes are analyzed and recorded.

Example 12A

NRT2.1 Reporter Screen

The NRT2.1 gene codes for a high-affinity nitrate transporter in *Arabidopsis thaliana* (Nazoa et al. (2003) *Plant Mol. Biol.* 52: 689-703). The aim of this assay is to find genes that, when overexpressed, overcome the suppression of NRT2.1 by sufficient/excess available nitrogen and thus circumvent negative regulation of uptake system by high nitrogen.

A 1 kb promoter fragment of NRT2.1 gene was fused to YFP in a binary plasmid. A transgenic line containing this reporter construct (pNRT2.1::YFP) was isolated and propagated to be used for activation tagging. This line is referred to as "NRT2.1 WT," and all subsequent transformations were performed in this background. The basis of the screen is to select activation-tagged seedlings with YFP fluorescence that is higher than the "NRT2.1 WT" parent line, when grown on replete nitrogen (lx MS media).

Example 12B

NRT2.1 Reporter Screen Assay

The assay is done as given below: The NRT2.1 WT line is transformed with pKR1006 to generate the activation tagged T1 population. This T-DNA based binary construct contains four multimerized enhancer elements derived from the Cauliflower Mosaic Virus 35S promoter, corresponding to sequences −341 to −64, as defined by Odell et al. (1985) *Nature* 313:810-812. It also contains a DS-RED fluorescent marker under the control of the SCP promoter. This marker can be used to select transformed seeds containing the T-DNA element and the 35S enhancer.

The T1 population is screened for any outliers using Scanlyzer and YFPsight outliers, the strong expression outlier plantlets are transplanted and T2 seeds are collected. YFPsight program is a proprietary program that allows capturing of fluorescent pixel information and its quantification. The T2 outlier seedlings are screened under microscope and lines with strong YFP expression profile, seedlings are transplanted. The T2 aerial tissue is collected for T-DNA insertion analysis, and candidate genes are cloned. The candidate genes are transformed into Nrt2.1 background Ds-Red vector and T1 lines are screened for YFP-root expression levels for validation.
Media preparation (1 Liter):
4.4 g MS basal salt mixture (sigma M5519 or Phytotech M524 (preferred))
10 g Sucrose
10 g Noble agar (Sigma A-5431, check lot # to make sure less than 2 years from certification)
pH 5.7
Agarclave sterilization
When cooled to 55° C. add 0.5 ml Timentin.

For plating seeds, left to right spacing is determined from testing and optimization on Lemnatec. The spacing needs to match up with the YFPSight Program for analysis. YFPSight is setup to analyze 6 plants on a plate individually. It is very important that the roots grow down the plate and not across. This can generate false positives and result in the loss of outliers.

Imaging is done on Lemnatec 6 days after plating. Outliers are selected after image analysis using YFPSight. Outliers are selected through Minitab boxplot analysis. Outliers are placed back in growth chamber and transplanted to soil in another 6 days, after which seeds are harvested and T2 analysis is done. For T2 and validation lines: 36 seeds per line are plated, 6 per plate. The plates are manually viewed under the microscope. No image is taken. Plants are assessed for YFP expression in root and grouped into strong and weak as given below:

Strong expression: when almost full length of root is expressing and the expression is bright.

Weak expression: when part of root is expressing and is not as bright.

Plates with strong expressing plants are returned to growth chamber and transplanted after 6 days. Fresh and/or frozen tissue is harvested from these plants and sent for border/insert analysis.

Example 13A

Suppressor Screening to Identify Genes that Suppress the nia1nia2 Mutant Phenotype The *Arabidopsis thaliana* NIA1 and NIA2 genes (At1g77760 and At1g37130) are the genes that encode nitrate reductase (NR). An *Arabidopsis* nia1nia2 knock-out (KO) mutant has <1% of wild-type NR activity and show several features of nitrogen-starved plants (Wilkinson J Q et al. 1993 *Mol. Gen. Genet.* 239(1-2):289-297). We designed a screen that would allow us to identify genes that can suppress the nitrogen-starved phenotype displayed by the nia1nia2 mutant.

The nia1nia2 knockout mutant line was procured from the *Arabidopsis* Biological Resource Center, stock # CS2356. The primers for genotyping the knock-out line are given in SEQ ID NOs:14-17; SEQ ID NOs:14 and 15 for NIA1 and SEQ ID NOs:16 and 17 for NIA2 (Lozano-Juste, J. et al. 2010 *Plant Physiol.* 152:891-903).

FIG. 23 shows the phenotypes in the wt and the nia1nia2 *Arabidopsis* plants. Mutant plants were pale green, smaller in size with narrow leaves that curled under.

An activation-tagged population in the nia1nia2 KO mutant background was created and used for screening.

Example 13B

Assay to Identify Suppressors of the nia1nia2 Mutant Phenotype

Transgenic T1 seeds from the nia1nia2 activation tagged population can be identified using the COPAS™ *Arabidopsis* seed sorting instrument selecting for fluorescent seeds, using the DsRed filter.
Overview of the Assay:
COPAS sorting and planting schedule:
The planting is done on a date 6-14 days from COPAS sort; 12+ days correspond to highest germination rate.
The scoring is done on a date 3-4 weeks from planting date. Selected mutants are marked. The mutants are selected based on the following criteria: For selecting mutants that are a rescue of the nia1nia2 phenotype, mutants that show wider leaves, greener and bigger than nia1nia2 mutant plants are selected. Imaging is done using LemnaTec.
All pots with at least one selected mutant are combined into one flat and all the transgenic plants that do not show a rescue of the nia1nia2 phenotype are removed from these pots.

Nitrogen is added to the flat after phenotyping to produce a healthy seed set. Seeds are harvested for rescreening at T2 stage. After confirming segregation, tissue can be collected and DNA extracted for insert analysis. For validation of genes found from insert analysis, the genes can be transformed into nia1nia2 background to confirm the phenotype of the T1 generation.

Example 14A

Suppressor of Antimyb Screen (SAM): Generation of Activation-Tagged Population in Antimyb Background The antimyb *Arabidopsis* mutant line was generated by overexpression of an artificial microRNA targeting AtMYB48 (At3g46130) and AtMYB59 (At5g59780) in Col-0, resulting in an early senescence phenotype (FIG. 24A-FIG. 24B). This phenotype can be corrected by supplementing the mutant with nitrogen, suggesting that the antimyb mutant is deficient in either nitrogen assimilation or remobilization.

The SAM (Suppressor of antimyb screen) population was generated by transformation of Activation Tagging Vector pKR1006 into the antimyb mutant background. This T-DNA based binary construct contains four multimerized enhancer elements derived from the Cauliflower Mosaic Virus 35S promoter, corresponding to sequences −341 to −64, as defined by Odell et al. (1985) *Nature* 313:810-812. It also contains a DS-RED fluorescent marker under the control of the SCP promoter. This marker can be used to select transformed seeds containing the T-DNA element and the 35S enhancer.

After transformation of antimyb with pKR1006, individual transformants containing pKR1006 were identified on the basis of red fluorescence in the seed, using a COPAS seed sorter. These activation-tagged transformants are phenotyped as described in Example 14B.

Example 14B

Suppressor of Antimyb Screen: Screening of the Activation-Tagged Population

Individual transformants from the activation-tagged population in the antimyb background can be screened for suppression of the antimyb early senescence phenotype.
Growth conditions for phenotyping:
Normal growth chamber conditions (16 h of light at 22° C. temperature and 50% relative humidity)
Soil: metro mix 360 (mix 4 bags to normalize for bag-to-bag variation in nutrients)
Water: tap water
Growth cycle:
Cold shock seeds 2-4 days
Day 1: planting
Day 7: basta spray to remove any wild-type contaminants
Day 10: thin plants
Day 21-Day 35: phenotyping
SAM population T1 screen: Phenotyping is done to find positive plants ("putants" or putative candidates) that show late senescence compared to the rest of the plants in the same flat (batch); T2 seeds from all putants are saved.
SAM population T2 screen (1$^{st}$ round): Phenotyping is done for the putative candidate lines compared to the antimyb col-0 control plants.

Phenotyping is done as follows:
Positive lines are scored when lines show 3:1 segregation and late senescence; the seeds are saved for these lines.
Negative lines show early senescence (similar to antimyb col-0 control plants)
No segregation lines show late senescence but no 3:1 segregation; phenotyping is redone for "no segregation" lines.
For the SAM population T2 screen ($2^{nd}$ round for the positive lines):
Lines from round 1 are screened, and compared to 2 controls: antimyb Col-0 plants and wt Col-0 plants.
Phenotyping is done as follows:
Positive lines are scored when the lines show 3:1 segregation and late senescence (similar to wt Col-0 plants); tissue is collected and the inserts are identified.
Negative lines show early senescence (similar to antimyb Col-0 plants).
No segregating lines show late senescence but no 3:1 segregation.
Candidate identification:
Candidate identification for each positive line is done and the candidate genes are transformed into antimyb Col-0 and wt Col-0 plants.
For phenotyping lines in antimyb background in the 35S phenotyping, the non-transgenic siblings from the same line can be taken as control.
For Phenotyping: Positive lines (most of the plants) show late senescence; seeds are saved and tissue is collected.
Negative lines: where all the plants show early senescence (similar to control).
A small RNA northern assay is carried out to eliminate lines in which the antimyb artificial miRNA has been silenced due to cosuppression.

Example 15

High Light/Low Nitrogen Assay for *Arabidopsis*

A systematic screen to identify *Arabidopsis* mutants tolerant to high light stress and low nitrogen stress is presented.

Materials and Methods:
*Arabidopsis* transgenic plants are used as test lines. Non-transgenic lines are used as susceptible controls.
Nitrogen level: 1 mM $NH_4NO_3$
Soil: Sunshine mix #2/LB2 (Sun Gro Horticulture Canada Ltd.)
Composition of Nutrient Solution (NS):
Final concentration:
10 mM $KH_2PO_4$
2 mM $MgSO_4$
1 mM $CaCl_2$
0.1 mM Fe-EDTA
50 µM $H_3BO_3$
12 µM $MnSO_4$
1 µM $ZnCl_2$
1 µM $CuSO_4$
0.2 µM $Na_2MoO_4$
Growing Conditions for the Assay:
16 hr light at 22° C., 65% humidity
8 hr dark at 20° C., 65% humidity
Light intensity conditions for the assay:
Normal light: ~120 microeinstein
High light (2 regimes): ~350 or ~500 microeinstein
Water regime: water every 4 days; water with Nutrient Solution (NS) only for the first two weeks, water with 1 L of NS+N/flat every 4 days
The assay is done as per the regime given below:
Day 1: make flats: soak each flat with 3 L of NS+1 mM $NH_4NO_3$ and plant seeds; grow under normal light;
Day 10: thin plants to 1 plant/spot;
Day 12: switch to high light;
Day 15: water each flat with 1 L of NS+N/flat;
Day 17 start LemnaTec imaging;
Day 19: water each flat with 1 L of NS+N/flat;
Day 23: water each flat with 1 L of NS+N/flat;
Day 26: end LemnaTec imaging.
Each flat has 4 pots of mutants and 4 pots of control in a zig-zag pattern. Each pot has 9 plants. The flats are rotated everyday if possible.
Phenotyping is done visually looking for larger and/or greener mutant plants as compared to the control plants.

We claim:

1. A method of selecting seeds from at least one transgenic plant line with general osmotic stress tolerance, the method comprising the steps of:
   a. obtaining seeds from at least one transgenic plant line comprising at least one heterologous polynucleotide sequence;
   b. subjecting the seeds to osmotic stress by placing them on media comprising four osmolytes, wherein the four osmolytes are sodium chloride, mannitol, sorbitol and polyethylene glycol, and the osmotic pressure exerted by the four osmolytes in the media is in the range of 0.4-1.23 MPa; and
   c. selecting seeds that show an increased percentage seedling emergence when compared to seeds from a control plant, wherein the control plant does not comprise the at least one heterologous polynucleotide sequence, and wherein the seeds from the control plant are subjected to the same osmotic stress as in part (b).

2. The method of claim 1, wherein the emerged seedlings of step (c) are further screened for either percentage leaf emergence or percentage leaf greenness, or for both percentage leaf emergence and percentage leaf greenness.

3. A method for identifying at least one plant with general osmotic stress tolerance, the method comprising the steps of:
   a. obtaining a population of plants of a single species;
   b. subjecting seeds of the plants of part (a) to osmotic stress by placing them on media comprising four osmolytes, wherein the four osmolytes are sodium chloride, mannitol, sorbitol and polyethylene glycol, and the osmotic pressure exerted by the four osmolytes in the media is in the range of 0.4-1.23 MPa;
   c. selecting seeds of part (b) that show an increased percentage seedling emergence when compared to an average of the percentage seedling emergence of the seeds of step (b); and
   d. growing plants from the selected seeds of step (c).

4. The method of claim 3, wherein the emerged seedlings of step (c) are further screened for either percentage leaf emergence or percentage leaf greenness, or for both percentage leaf emergence and percentage leaf greenness.

5. The method of claim 1, wherein the at least one heterologous polynucleotide sequence is operably linked to a promoter.

6. The method of claim 5 wherein the promoter is a tissue-specific promoter.

7. The method claim 5 wherein the promoter is an inducible promoter.

8. The method of claim 1, wherein the step (a) of obtaining seeds from at least one transgenic plant line comprising at least one heterologous polynucleotide sequence is done for at least one hundred transgenic plant lines.

* * * * *